United States Patent
Duchon et al.

(10) Patent No.: US 7,320,325 B2
(45) Date of Patent: Jan. 22, 2008

(54) METHOD AND APPARATUS FOR CREATING INTRAUTERINE ADHESIONS

(75) Inventors: Douglas J. Duchon, Chanhassen, MN (US); James Presthus, Edina, MN (US)

(73) Assignee: Impres Medical, Inc., Edina, MN (US)

( * ) Notice: Subject to any disclaimer, the term of this patent is extended or adjusted under 35 U.S.C. 154(b) by 322 days.

(21) Appl. No.: 10/726,433

(22) Filed: Dec. 3, 2003

(65) Prior Publication Data
US 2004/0152977 A1 Aug. 5, 2004

Related U.S. Application Data

(63) Continuation of application No. 09/840,951, filed on Apr. 24, 2001, now Pat. No. 6,708,056.

(60) Provisional application No. 60/256,529, filed on Dec. 18, 2000, provisional application No. 60/199,736, filed on Apr. 25, 2000.

(51) Int. Cl.
*A61F 6/06* (2006.01)
(52) U.S. Cl. .................... 128/833; 128/839
(58) Field of Classification Search ............ 600/431, 600/433, 434, 435; 128/898, 830, 831, 832, 128/833, 834, 835, 836, 837, 838, 839, 840, 128/841; 514/381; 424/78.06, 423; 604/514, 604/515, 518
See application file for complete search history.

(56) References Cited

U.S. PATENT DOCUMENTS

| | | |
|---|---|---|
| 3,802,425 A * | 4/1974 | Moulding, Jr. ............ 128/839 |
| 4,846,818 A | 7/1989 | Keldahl et al. |
| 5,095,917 A * | 3/1992 | Vancaillie .................. 128/831 |
| 5,391,146 A | 2/1995 | That et al. |
| 5,551,443 A | 9/1996 | Sepetka et al. |
| 5,601,600 A | 2/1997 | Ton |
| 5,704,899 A | 1/1998 | Milo |
| 5,716,321 A | 2/1998 | Kerin et al. |
| 5,746,769 A | 5/1998 | Ton et al. |
| 5,807,239 A | 9/1998 | DiBernardo |
| 5,873,815 A | 2/1999 | Kerin et al. |
| 5,891,457 A * | 4/1999 | Neuwirth .................. 128/833 |
| 5,935,056 A | 8/1999 | Kerin et al. |
| 5,935,098 A | 8/1999 | Blaisdell et al. |
| 5,947,958 A | 9/1999 | Woodard et al. |

(Continued)

OTHER PUBLICATIONS

Okumura et al., "Experimental Study of a New Tracheal Prosthesis Made From Collagen-grafted Mesh", *Trans Am Soc Artif Intern Organs 1991*, Jul./Sep. 1991, pp. M317-M319, vol. 37, ASAIO Transactions, Toronto, California.

(Continued)

*Primary Examiner*—Michael A. Brown
(74) *Attorney, Agent, or Firm*—Inskeep IP Group, Inc.

(57) ABSTRACT

An apparatus and method of use or treatment are disclosed for creating intrauterine adhesions resulting in amenorrhea. In particular, the apparatus relates to an easily deployed intrauterine implant that readily and consistently reduces or eliminates abnormal intrauterine bleeding. In addition, the apparatus is also used as a uterine marker device for visualizing endometrial tissue thickness and potential changes. The method of the present invention serves as a supplement to or a replacement for conventional hysterectomy or ablation/resection procedures used to treat menorrhagia.

53 Claims, 49 Drawing Sheets

U.S. PATENT DOCUMENTS

| | | | |
|---|---|---|---|
| 6,026,331 A * | 2/2000 | Feldberg et al. | 607/102 |
| 6,071,283 A | 6/2000 | Nardella et al. | |
| 6,080,129 A | 6/2000 | Blaisdell | |
| 6,080,152 A | 6/2000 | Nardella et al. | |
| 6,090,997 A * | 7/2000 | Goldberg et al. | 424/78.06 |
| 6,136,333 A * | 10/2000 | Cohn et al. | 424/423 |
| 6,145,505 A | 11/2000 | Nikolchev et al. | |
| 6,165,492 A * | 12/2000 | Neuwirth | 128/833 |
| 6,176,240 B1 | 1/2001 | Nikolchev et al. | |
| 6,196,966 B1 | 3/2001 | Kerin et al. | |
| 6,211,217 B1 * | 4/2001 | Spinale et al. | 514/381 |
| 6,526,979 B1 | 3/2003 | Nikolchev et al. | |
| 6,634,361 B1 | 10/2003 | Nikolchev et al. | |
| 6,679,266 B2 | 1/2004 | Nikolchev et al. | |
| 6,684,884 B2 | 2/2004 | Nikolchev et al. | |
| 6,709,667 B1 | 3/2004 | Lowe et al. | |
| 2005/0171569 A1 * | 8/2005 | Girard et al. | 606/193 |
| 2006/0089658 A1 * | 4/2006 | Harrington | 606/119 |

OTHER PUBLICATIONS

Acta Europaea Fertilitatis, European Journal of Fertility and Sterility, vol. 19, No. 1, 1988, pp. 13-16, "*Cervical Isthmic Adhesions And The Endometrium: Hysteroscopic Study (Suggestion For An Endometrial Inhibiting Factor)*".

Iomedicine Express, vol. 31-No. 5-1979, pp. 121-122, "*Squamous Metaplasia Of The Endometrium—Endometrial Response To Intrauterine Presence Of Fibro Blast-Carrying Ivalon Sponge*".

Okumura, Norihito, *Experimental Study of a New Tracheal Prosthesis Made from Collagen-grafted Mesh*, Trans Am Soc Artif Intern Organs Jul. 1991, pp. M317-M319, vol. XXXVII, Toronto, Canada.

Polishuk, W.Z., *Endometrial Regeneration and Adhesion Formation*, South African Medical Journal, Mar. 1975, pp. 440-442, vol. 49.

Rabau, E. and David, A., *Intrauterine Adhesions: Etiology, Prevention, and Treatment*, Nov. 1963, pp. 626-629, vol. 22, No. 5.

Buttram, V.C. and Turati, G., *Uterine Synechiae: Variations in Severity and Some Conditions Which may be Conducive to Severe Adhesions*, Int. J. Fertil., 1977, pp. 98-103, vol. 22.

"Collagen and the Wound Healing Process," printed from website http://www.woundheal.com/pubs/woundPub09.htm, 13 pages, on Jun. 25, 2001.

"Pelvic Adhesions," printed from website http://matweb.hcuge.ch/matweb/El_Mowafi/Pelvic_adhesions.htm, 21 pages, on Mar. 10, 2001.

"Section 4-1: Review of Wound Management Materials—(Untitled Section)" printed from website http://www.smtl.co.uk/WMPRC/VFM-report/VFM-Chapter4-1.html, 17 pages, on Feb. 27, 2001.

"1.1.2 *Factors Involved in Cell Damage*," printed from website http://savba.savba.sk/logos/books/scientific/node7.html, 4 pages, on Feb. 9, 2001.

Asherman, J.G., *Amenorrhoea Traumatica (Atretica)*, Journal of Obstetrics and Gynaecology, pp. 23-30.

Jensen, P.A. and Stromme, W.B., *Amenorrhea Secondary to Puerperal Curettage (Asherman's Syndrome)*, Am. J. Obst. & Gynec., May 15, 1972, pp. 150-154, vol. 113, No. 2.

Jones, W.E., *Traumatic Intrauterine Adhesions: A Report of 8 Cases with Emphasis on Therapy*, Am. J. Obst. & Gynec., Jun. 1, 1964, pp. 304-313, vol. 89, No. 3.

Jewelewicz, R., Khalaf, S., Neuwirth, R.S. and Vande Wiele, R.L., *Obstetric Complications After Treatment of Intrauterine Synechiae (Asherman's Syndrome)*, Jun. 1976, pp. 701-705, vol. 47, No. 6.

"Asherman's Syndrome: A Consequence of Abortion," printed from website http://www.ewtn.com/library/PROLIFE/ASHERSYN.TXT, 3 pages, on Feb. 15, 2001.

Chapman, K. and Chapman, R., *Asherman's Syndrome: A Review of the Literature, and a Husband and Wife's 20-year World-Wide Experience*, Journal of the Royal Society of Medicine, Sep. 1990, pp. 577-580, vol. 83.

Dizerega, G.S., *The Cause and Prevention of Postsurgical Adhesions: A Contemporary Update*, Gynecologic Surgery and Adhesion Prevention, 1993, pp. 1-18, Wiley-Liss, Inc.

Tompkins, P., *Traumatic Intrauterine Synechiae: The Asherman Syndrome*, Am. J. Obst. & Gynec., Jun. 15, 1962, pp. 1599-1608, vol. 83, No. 12.

Netter, A., Musset, R., Lambert, A. and Salomon, Y., *Traumatic Uterine Synechiae: A Common Cause of Menstrual Insufficiency, Sterility, and Abortion*, Am. J. Obst. & Gynec., Feb. 1956, pp. 368-375, vol. 71, No. 2.

Sanfilippo, J.S., Fitzgerald, M.R., Badawy, S.Z.A., Nussbaum, M.L. and Yussman, M.A., *Asherman's Syndrome: A Comparison of Therapeutic Methods*, The Journal of Reproductive Medicine, Jun. 1982, pp. 328-330, vol. 27, No. 6.

Asherman, J.G., *Traumatic Intra-Uterine Adhesions*, Journal of Obstetrics and Gynaecology, pp. 892-903.

Polishuk, W.Z. and Sadovsky, E., *A Syndrome of Recurrent Intrauterine Adhesions*, Am. J. Obst. & Gynec., Sep. 15, 1975, pp. 151-158, vol. 123, No. 2.

Klein, S.M. and Garcia, C.R., *Asherman's Syndrome: A Critique and Current Review*, Fertility and Sterility, Sep. 1973, pp. 722-735, vol. 24, No. 9, The Williams & Wilkins Co., USA.

Lancet, M. and Mass, N., *Concomitant Hysteroscopy and Hysterography in Asherman's Syndrome*, Int. J. Fertil., 1981, pp. 267-272, vol. 26, No. 4, U.S. International Foundation for Studies in Reproduction, Inc.

"Asherman's Syndrome and Abortion: A Short Review," printed from website http://pages.map.com/lroberge/ashermn.htm, 3 pages, on Jun. 27, 2001.

"Ethicon Products," printed from website http://www.ethiconinc.com/wound_management/wound_con.htm, 1 page, on Jul. 7, 2001.

"How Often Does One Get the Chance to Reshape History?" printed from website http://www.perfixplug.com/herniapd.htm, 1 page, on Sep. 18, 2000.

"Atrium," printed from website http://www.atriummed.com/productsmenu.htm, 1 page, on Jul. 7, 2001.

Surgical Mesh,, printed from webite http://www.atriummed.com/mesh.htm, 2 pages, on Jul. 7, 2001.

"Hydromer," printed from website http://www.hydromer.com/products.htm, 2 pages, on Jul. 7, 2001.

"Worldwide Businesses: Davol Inc.," printed from website http://www.crbard.com/global/davol.html, 2 pages, on Jul. 7, 2001.

"Precision Screening and Filter Fabrics: Sefar Trademarks," printed from website http://www.sefar.com/scripts/db4web_c.exe/db/sefar/division_pages_f.d4w?lang=2&app=sefar_filtration&area=17, 1 page, on Jul. 7, 2001.

"Precision Screening and Filter Fabrics: Sefar Propyltex," printed from website http://www.sefar.com/scripts/db4web_c.exe/db/sefar/division_pages_f.d4w?lang=2&app=sefar_filtration&area=17, 1 page, on Jul. 7, 2001.

Middleton, J.C. and Tipton, A.J., *Synthetic Biodegradable Polymers as Medical Devices*, Medical Plastics and Biomaterials, Mar./Apr. 1998, pp. 31-39.

*Freeze-Dried Regenafil™: Handling Instructions*, Oct. 11, 2000, pp. 1-2, Regeneration Technologies, Inc., Alachua, FL.

*Engineered Collagen Matrix™*, 2000, pp. 1, Organogenesis, Inc., Canton, MA.

"Surgical Applications of Tissue Sealants," printed from website http://www.healthtech.com/conference/00fsc/, 9 pages, on Feb. 2, 2001.

*Regenafil™ Allograft Paste: The Use of Gelatin as an Effective Delivery System for Regenafil™ Allograft Paste*, Apr. 1999, pp. 1-5, Regeneration Technologies, Inc., Alachua, FL.

*In Vivo Determination of the Optimal Amount of DBM in a DBM/Carrier Composite Required to Optimize Bone Formation*, Apr. 1999, pp. 1-6, Regeneration Technologies, Inc., Alachua, FL.

"Surgical Hemostats," printed from website http://www.vasoseal.com/sh/shsurgical.html, 1 page, on Apr. 26, 2001.

"Collagen Biomaterials," printed from website http://www.vasoseal.com/cb/cbbiomaterials.html, 1 page, on Apr. 26, 2001.

"Recombinant Gelatin: Medical Uses of Gelatin," printed from website http://www.fibrogen.com/gelatin/, 1 page, on Apr. 26, 2001.

"Hemostatic Biomaterial Evaluation," printed from website http://www.upmc.edu/McGowan/BioBio/Project7.htm, 2 pages, on Feb. 27, 2001.

"Collagen Types," printed from website http://zygote.swarthmore.edu/cell6.html, 3 pages, on Apr. 26, 2001.

"Many Uses for Collagen," printed from website http://www.fibrogen.com/collagen/uses.html, 1 page, on Apr. 26, 2001.

"Recombinant Collagen Technology Platform," printed from website http://www.fibrogen.com/tissue/recombinant.html, 1 page, on Apr. 26, 2001.

"Why Recombinant Human Collagen?" printed from website http://www.fibrogen.com/collagen/, 1 page, on Apr. 26, 2001.

"Tissue Engineering," printed from website http://www.fibrogen.com/tissue/, 2 pages, on Apr. 26, 2001.

"What is Fibrosis?" printed from website http://www.fibrogen.com/fibrosis/, 2 pages, on Apr. 26, 2001.

"Collagen and Elastin," printed from website http://www.accessexcellence.com/AB/GG/collagen_Elastin.html, 1 page, on Apr. 26, 2001.

Ambrosio, L., De Santis, R. and Nicolais, L., *Advanced Composite Hydrogels for Implant and Tissue Engineering Applications*, pp. 1-6.

"Natural Matrix (Xenograft) OsteoGraf® N-Block," printed from website http://fp.ceramed.com/natural_matrix_xenograft.htm, 1 page, on Apr. 23, 2001.

"Contact Info," printed from website http://www.allosource.org/html/contact.html, 1 page, on Apr. 23, 2001.

"Accredited Bank List," printed from website http://www.aatb.org/aatbac.htm, 7 pages, on Apr. 10, 2001.

*Microwave Endometrial Ablation (MEA™)*, Microsulis Group, pp. 6.

*BEI Medical Systems: The New Choice for Menorrhagia*, pp. 4, BEI Medical Systems Company, Inc., Teterboro, NJ.

*GyneLase™ Improving the Quality of Life: A Breakthrough in Eliminating Menorrhagia, An Outpatient Procedure Using ELITT™*, pp. 6, ESC Medical Systems, Ltd.

"Novel Uterine Surgery Shows Promise," printed from website http://www.msnbc.com/news/425865.asp, 3 pages, on Nov. 9, 2000.

". . . The NovaSure™ Endometrial Ablation System," printed from website http://www.novacept.com/novasure.shtml, 1 page, on Jun. 25, 2000.

". . . Patient Information," printed from website http://www.novacept.com/patient.shtml, on Jun. 25, 2000.

". . . Physician Information," printed from website http://www.novacept.com/physician.shtml, on Jun. 25, 2000.

"Conceptus Receives FDA Approval to Commence Pivotal Trial of Stop Device," printed from website http://www.conceptus.com/IDEapproval.html, 2 pages, on Aug. 2, 2000.

"Company Profiles," printed from website http://www.stephens.com/research/conferences/companies.asp?cid=7, 2 pages, on Aug. 3, 2000.

"Uterine Balloon Therapy: Alternative to Hysterectomy", printed from website http://www.midlife-passages.com/pr01.htm, 2 pages, on Nov. 25, 2000.

". . . Novacept News: Novacept Bipolar Endometrial Ablation System," printed from website http://www.novacept.com/cooper.shtml, 3 pages, on Apr. 13, 2001.

"Endometrial Laser Intrauterine Thermotherapy Safe, Effective for Menorrhagia," printed from website http://www.urology.medscape.com/reuters/prof/2000/11/11.06/20001103drgd002.html, 2 pages, on Nov. 8, 2000.

"Hydro ThermAblation," printed from website http://www.corybros.co.uk/hta.htm, 2 pages, on Feb. 14, 2001.

"The Quinacrine Method of Non-surgical Female Sterilization," printed from website http://www.quinacrine.com/intro.html, 4 pages, on Jan. 26, 2001.

Zipper, J., Cole, L.P., Goldsmith, A., Wheeler, R. and Rivera, M., *Quinacrine Hydrochloride Pellets: Preliminary, Data on a Nonsurgical Method of Female Sterilization*, Int. J. Gynaecol. Obstet., 1980, pp. 275-279, vol. 18.

Zipper, J., Medel, M., Pastene, L. and Rivera, M., *Intrauterine Instillation of Chemical Cytotoxic Agents for Tubal Sterilization and Treatment of Functional Metrorrhagias*, International Journal of Fertility, Oct.-Dec. 1969, pp. 280-288, vol. 14, No. 4.

"Uterus: Normal Uterine Appearance and Dimensions," printed from website http://www.ohsu.edu/ps-DiagRadiol/kojima/uterus.htm, 2 pages, on Jul. 7, 2001.

*Pelvic Surgery: Adhesion Formation and Prevention*, Jan. 15, 1997, pp. 1-269, Springer.

*Sclerosing Agents*, UK Special Unit, pp. 1-3.

*Impres Medical Inc.: Company Profile Spring/Summer 2001*, 2001, pp. 2, Impres Medical Inc., Minneapolis, MN.

Diamond, M.P., Dizerega, G.S., Linsky, C.B. and Reid, R., *Gynecologic Surgery and Adhesion Prevention*, Mar. 1993, Wiley-Liss.

*Surgical Adhesives and Sealants: Current Technology and Applications*, Mar. 31, 1996, pp. 1-247, Technomic Pub. Co.

Schenker, J.G., *Etiology of and Therapeutic Approach to Synechia Uteri*, European Journal of Obstetrics & Gynecology and Reproductive Biology, 1996, pp. 109-113, 65, Elsevier Science Ireland, Ltd., Ireland.

Schenker, J.G. and Margalioth, E.J., *Intrauterine Adhesions: An Updated Appraisal*, Fertility and Sterility, May 1982, pp. 593-609, vol. 37, No. 5, The American Fertility Society, USA.

Schenker, J.G. and Yaffe, H., *Induction of Intrauterine Adhesions in Experimental Animals and in Women*, Israel J. Med. Sci., Feb. 1978, pp. 261-266, vol. 14, No. 2.

Schenker, J.G. and Polishuk, W.Z., *Induction of Intrauterine Adhesions in the Rabbit with Autogenous Fibroblast Implants*, Am. J. Obst. & Gynec., Mar. 15, 1973, pp. 789-794, vol. 115, No. 6.

Schenker, J.G. and Polishuk, W.Z., *The Effect of Tissue Adhesives on the Endometrium of the Rabbit*, Contraception, Feb. 1973, pp. 145-152, vol. 7, No. 2.

Schenker, J.G., Sacks, M.I., and Polishuk, W.Z., *Regeneration of Rabbit Endometrium Following Curettage*, Am. J. Obst. & Gynec., Dec. 1, 1971, pp. 970-978, vol. 111, No. 7.

Schenker, J.G., Nicosia, S.V., Polishuk, W.Z., and Garcia, C.R., *An In Vitro Fibroblast-Enriched Sponge Preparation For Induction of Intrauterine Adhesions*, Israel J. Med. Sci., Aug. 1975, pp. 849-850, vol. 11, No. 8.

* cited by examiner

METHOD AND APPARATUS FOR CREATING INTRAUTERINE ADHESIONS

CROSS REFERENCE TO RELATED APPLICATIONS

The present invention is a continuation of U.S. patent application Ser. No. 09/840,951, filed Apr. 24, 2001, now U.S. Pat. No. 6,708,056 which claims priority to U.S. Provisional Application Ser. No. 60/256,529, filed Dec. 18, 2000, and U.S. Provisional Application Ser. No. 60/199,736, filed Apr. 25, 2000, whose contents are fully incorporated herein by reference.

BACKGROUND OF THE INVENTION

Menstrual bleeding is a part of normal life for women. The onset of menstruation, termed menarche, usually occurs at the age of 12 or 13. The length of a woman's monthly cycle may be irregular during the first one to two years. Once the menstrual cycle stabilizes, a normal cycle may range from 20 to 40 days, with 28 days commonly being an average. Age, weight, athletic activity and alcohol consumption are several factors that affect menstrual cycles. For example, younger women (under the age of 21) and older women (over the age of 49) tend to have longer cycle times, generally averaging 31 days and over. Similarly, women who are very thin or athletic also have longer cycles. In contrast, women who consume alcohol on a regular basis tend to have shorter cycle times.

Nearly all women, at some time during their reproductive life, experience some type of menstrual disorder. These disorders range from mild to severe, often resulting in numerous lost work hours and the disruption of personal/family life each month. In general, physical symptoms such as bloating, breast tenderness, severe cramping (dysmenorrhea) and slight, temporary weight gain frequently occur during most menstrual cycles. In addition to physical symptoms, emotional hypersensitivity is also very common. Women report a wide range of emotional symptoms, including depression, anxiety, anger, tension and irritability. These symptoms are worse a week or so before a woman's menstrual period, generally resolving afterward.

Many women also suffer from a condition called menorrhagia (heavy bleeding). Menorrhagia is a clinical problem characterized by extremely heavy flow/bleeding and major discomfort characterized by blood loss exceeding 80 cc/month. It is estimated that 1 in 5 women between the ages of 35 and 50, or approximately 6.4 million women in the United States alone, are affected by menorrhagia. Fibroids, hormonal imbalance and certain drugs, such as anticoagulants and anti-inflammatory medications, are common causes of heavy bleeding.

Women diagnosed with menorrhagia or dysmenorrhea have limited treatment options available to them. Currently, other than hormone therapy and a few experimental pain management techniques, hysterectomy (removal of the uterus) and endometrial ablation/resection (destruction of the lining of the uterus) are the clinically accepted treatment modalities for menorrhagia. Both of these surgical procedures eliminate the possibility of childbearing. Further, hysterectomy requires up to a six week recovery time and a lifetime of hormone therapy when the ovaries are removed. Endometrial ablation has a low success rate at achieving amenorrhea (cessation of menstrual bleeding). As a result, many of the women affected by menorrhagia are driven to make lifestyle-altering decisions.

Over 600,000 hysterectomies are performed each year in the United States. It is estimated that 1 in 3 women in the U.S. have a hysterectomy before the age of 65. Menorrhagia is the most common reason why hysterectomies are performed. Several studies have estimated that menorrhagia is the cause of 30% (some studies as high as 50%) of the 600,000 annual hysterectomies, resulting in a basis of 180,000 to 300,000 procedures annually. Financially, these numbers translate into annual hospital costs that exceed $5 billion per year.

Based on these statistics, hysterectomy is a very common operation. In general, there are three types of hysterectomies: partial, total and radical. As shown in FIG. 1, a partial hysterectomy involves removal of the upper portion 10 of the uterus 12 (whereby the dotted lines in the figure indicated the area removed), leaving the cervix 14 and the base 16 of the uterus 12 intact. FIG. 2 illustrates a total hysterectomy whereby the entire uterus 12 and cervix 14 are removed. A radical hysterectomy, shown in FIG. 3, entails removal of the uterus 12, both Fallopian tubes 18, both ovaries 20, and the upper part of the vagina 22. Each of the above three procedures may be performed via an abdominal incision (abdominal hysterectomy) or through a vaginal incision (vaginal hysterectomy).

After the operation, the hospital stay is generally less than a week, depending on the type of hysterectomy and whether there are any complications. Since a hysterectomy is a major operation, discomfort and pain from the surgical incision are most pronounced during the first few days after surgery. Medication is available to minimize these symptoms. By the second or third day, most patients are up walking. Normal activity can usually be resumed in four to eight weeks and sexual activity can usually be resumed in six to eight weeks.

Since the 1800's, attempts using various treatments have been made to control uterine bleeding by means other than hysterectomy. Alternative methods include chemicals, steam, ionizing radiation, lasers, electrocautery, cryosurgery and others. The long-term risk for such procedures is quite high and may lead to other more serious complications such as mixed mesodermal tumors or uterine cancer.

Typical therapy or treatment options include drug therapy followed by dilation and curettage (D & C) and, as a last resort, hysterectomy. Drug therapy is generally the first treatment option employed to treat excessive bleeding. Birth control pills, progestin, danazol and gonadotropin-releasing hormone (GnRH) are a few examples of drug treatments prescribed to reduce bleeding. In general, birth control pills contain synthetic forms of estrogen and progesterone, which prevent ovulation and, thereby, reduce endometrial build-up or thickness. As a result, pill users normally have lighter or minimal menstrual bleeding. Progestin, another synthetic form of progesterone, balances the effects of estrogen normally produced by the body and, similar to the pill, reduces endometrial growth. Often, Danazol and other GnRH agents are prescribed to suppress estrogen production and ovulation. As a result, menstrual bleeding stops or is significantly reduced. However, side-effects of such treatments may include bloating, breast tenderness, increased risk of osteoporosis and high cholesterol.

D & C, frequently a second treatment option for excessive bleeding, is a very common, minor surgical procedure that is generally performed on an outpatient basis in a hospital. Usually, the patient is given a general anesthetic, although the procedure occasionally is performed using only a local anesthetic. The dilation step of the procedure involves dilating or stretching the cervix, which is the lower part of the uterus. Once the cervix is appropriately dilated, the curettage step can then be performed. During curettage, a curette (a spoon-shaped instrument) is inserted through the vagina, past the cervix and into the uterus. The curette is then used to scrape and/or collect tissue from the inside surfaces of the uterus.

Endometrial ablation has become more popular and has been offered as another alternative treatment to hysterectomy for patients suffering from menorrhagia. In 1996, 179,000 ablation procedures were performed, up from 49,000 in 1993. This technique is intended to permanently ablate all layers of the endometrium and allow the cavity to become lined with fibrous tissue.

In general, endometrial ablation is less costly and requires less recovery time for the patient. However, the procedure has received mixed results for controlling bleeding, depending on the technique used, and has a limited success rate of no greater than 20% when defined as complete cessation of bleeding. During one five-year study of 525 women with an average age of 42, endometrial ablation completely stopped uterine bleeding only 26% to 40% of the time. However, approximately 79% to 87% of the women were satisfied with the surgery. About 16% of the women required a repeat ablation to stop bleeding and 9% of the women ultimately opted for a hysterectomy. Research has also shown that the effectiveness of endometrial ablation may decline over years, with menstruation returning in about one-third of women.

It should be noted, however, that the goal of endometrial ablation was never to create amenorrhea (cessation of menstrual periods). This procedure was originally developed as a less invasive alternative to hysterectomy in order to return women with menorrhagia to a normal menstrual flow.

In either endometrial ablation or resection, an attempt is made to remove or destroy the entire lining of the uterus (the endometrium). Endometrial resection, first described in 1983 by De Cherney et al., involves the use of a resectoscope-cutting loop to perform endometrial ablation to remove the lining of the uterus. In contrast, ablation generally uses either vaporization, coagulation or some other thermal energy source to destroy the uterine lining.

Although ablation and resection procedures are often discussed as if they are the same, they differ significantly. For example, some physicians argue that resection is more difficult. However, when it is performed skillfully, resection has much better results (control of bleeding in up to 88% of patients) than roller ball ablation (40% to 55%) and newer ablation techniques (3% to 30%).

There are various methods by which an endometrial ablation procedure may be performed. These methods include roller ball electrocautery, cryo-cauterization, microwave, free circulating water, vaporization, balloon ablation and photodynamic therapy. In general, these procedures are performed in a hospital or surgery center, not in the physician's office, due to the need for anesthesia.

Referring to FIG. 4, conventional endometrial ablation, commonly referred to as "roller ball" ablation, uses a device 24 that looks like a tiny steamroller. This device 24 applies heat and, thereby, destroys endometrial tissue 26 (whereby the destroyed tissue is shown in the figure by a dotted line) as it rolls across the uterine wall 28. Endometrial ablation usually takes 15 to 45 minutes and the patient can go home the same day, although a general anesthetic is usually required.

Another type of ablation procedure is vaporization. This technique involves vaporizing uterine tissue using a thin powerful laser beam or high electric voltage. Visualization of the uterine cavity is made possible by filling the cavity with fluid. If any resection or cauterization is performed, a special substance, such as glycine, sorbitol or mannitol, is used so that the fluid does not conduct electricity. This prevents accidental burn injuries to the rest of the uterus. Because this procedure involves removing or destroying the endometrium using a simple, rapid technique, it is often referred to as "global" endometrial ablation.

The NovaSure System is one example of a global endometrial ablation device used to perform ablation via controlled vaporization of the endometrium. The patient is sedated using a local anesthesia with IV sedation and the cervix is dilated. A gold-plated mesh triangle is delivered via a slender tube and expanded into the uterus of the patient. The shape of the mesh is configured to generally resemble the profile of the uterine cavity. Prior to energizing the mesh, suction is applied to bring the uterine cavity into close contact with the mesh. After energy has been delivered to the endometrial lining via the mesh for one to two minutes, the mesh is retracted and the tube removed from the patient's body.

In 1994, Singer et al. reported preliminary experience with an ablation system incorporating an intrauterine balloon. As shown in FIG. 5, balloon ablation utilizes a balloon 30 at the tip 32 of a catheter tube 34 that is filled with fluid and inflated until it conforms to the walls of the uterus 28. A probe in the balloon (not shown) heats the fluid to destroy the endometrial lining. After eight minutes, the fluid is drained out and the balloon 30 is removed. Pregnancy is possible if some of the lining is maintained, but the risk to mother and child is considerable.

Photodynamic therapy is another type of ablation method. A light-sensitive agent (photofrin II) that contains a cell-killing substance is given intravenously and is absorbed by the endometrium. A light anesthetic is administered and the physician then inserts a small probe into the uterine cavity, through which laser light is transmitted for a few minutes. The light activates the photofrin II, which causes destruction of the endometrium. Early results show reduced bleeding without significant side effects.

Other ablation methods to treat menorrhagia, such as microwave and freezing (cryoablation) techniques, are currently being investigated. However, long-term studies using these treatments to determine their effectiveness at producing amenorrhea and any potential side effects are still needed.

Although ablation and resection procedures are less invasive than hysterectomies, there are various complications that may occur. Examples of possible complications include perforation of the uterus, injury to the intestine, hemorrhage or infection. Another concern associated with ablation treatment involves the risk of cancer. Since ablation does not remove the uterus, women still are at risk for developing endometrial cancer (although the risk is reduced; however, no clinical proof is currently available). Further, because endometrial ablation alters the wall of the uterus, early detection of cancerous changes may be difficult to identify.

Other potential side effects of ablation procedures are infections caused by ablation or similar procedures and intrauterine adhesions. Intrauterine adhesions or synechiae are described as scar tissue inside the uterine cavity. Termed Asherman's Syndrome, intrauterine adhesions 36, as shown in FIG. 6, are band-like formations that develop as a result of injury or trauma to the uterus 12 (due to, for example, over-vigorous curettage to the uterus 12) or can also happen simultaneously.

In 1894, Heinrich Fritsch was the first to describe amenorrhea resulting from traumatic obliteration of the uterine cavity following puerperal curettage. However, it was not until 1948, that knowledge about uterine adhesions was first disseminated in medical journals by Joseph G. Asherman, for whom the condition is named. In 1957, the 17$^{th}$ Congress of the Federation of French Speaking Societies of Gynecology and Obstetrics proposed the following classification of uterine synechiae:

Traumatic Synechiae connected with surgical or obstetrical evacuation of the uterus
  Spontaneous synechiae of tuberculosis origin
  Synechiae occurring after myomectomy
  Synechiae secondary to the attack of chemical or physical agents and likewise those resulting from atrophic changes In general, two types of traumatic synechiae are currently recognized. The first type is stenosis or obliteration of the cervical canal. The second type of traumatic synechiae is partial or complete obliteration of the uterine cavity by conglutination of the opposing walls.

Other terms, such as endometrial sclerosis, traumatic uterine atrophy, uterine artesia, uterine synechiae and adhesive endometriosis, have also been used to describe the phenomena of Asherman's Syndrome. The severity of adhesion is generally classified into one of the following three groups or classes: Class I represents adhesions occurring in less than one-third of the uterine cavity with both ostia (i.e. openings of the Fallopian tubes) visible; Class II represents adhesions occurring in one-third to one-half of the uterine cavity with one ostium visible; and Class III represents adhesions occurring in greater than one-half of the uterine cavity with no ostium visible.

Although Asherman's Syndrome has been studied extensively and numerous articles and papers have been written on the topic, uncertainty still exists as to the predominant causative factor(s) and biological mechanism(s). A general diagram illustrating the process of adhesion formation after trauma is illustrated in FIG. 7. It is believed that if the endometrium is severely damaged, it may be replaced by granulation tissue. When this happens, the opposing uterine walls adhere to one another and form scar tissue. In particular, adhesions form and transluminally bridge the anterior and posterior surfaces of the uterus. The adhesions or tissue that is formed between the walls comprises connective tissue that is, typically, avascular. Soon after, the tissue may be infiltrated by myometrial cells and, later, covered by endometrium.

Conventionally, intrauterine adhesions have been regarded as undesirable conditions (for example U.S. Pat. No. 6,211,217, issued to Spinale et al, U.S. Pat. No. 6,136,333, issued to Cohn et al. and U.S. Pat. No. 6,090,997, issued to Goldbert et al.). Indeed, in several known treatment methods for menorrhagia, it has been encouraged to avoid the creation of adhesions. Even in those circumstances where clinicians have experimented with adhesion formation, the results have not proved promising. For example, in the March 1977 edition of the Israel Journal of Medicine, an article by J. G. Schenker, entitled *Induction of Intrauterine Adhesions in Experimental Animals and Women*, described an experiment in which surgical sponges were implanted into the subcutaneous wall of the patient. The sponges remained in the subcutaneous wall until fibroblasts, or connective-tissue cells, were formed within the sponges. Next, the sponges were then removed and implanted into the uterus of the same patient.

Schenker observed that, after a period of time, adhesions were formed in the areas adjacent to the location of the implanted fibroblast bearing sponge. No adhesions were observed in areas that did not have contact with the fibroblast bearing sponge. These experiments were carried out in several animal models (for example, rabbit, rat and primates) and humans. Schenker concluded that it was possible to artificially create adhesions within the uterus, but that such a procedure was not practical.

In view of the above, there is a need for a minimally invasive device and method to treat abnormal intrauterine bleeding. In particular, it is desirable that the device have a high success rate at treating menorrhagia and have minimal to no side-effects or related complications. Such a device must also be biocompatible and non-toxic. In addition, the related treatment methods should reduce patient recovery times and hospital costs. Overall, the method of treatment should also improve the quality of life for patients.

BRIEF SUMMARY OF THE INVENTION

In general, the present invention contemplates an implantable device for treating excessive bleeding in a body cavity. The device comprises a biocompatible material that is deliverable into the body cavity. The biocompatible material contains an attribute that promotes tissue growth that results in adhesion formation within the body cavity. The attribute of the biocompatible material is defined by at least one of a mechanical component of the biocompatible material and a non-cultured biologic component of the biocompatible material.

The present invention also contemplates a method of creating adhesions in a body cavity. In general, the method comprises inserting an implantable device within the body cavity. The method also includes locating the implantable device at an optimal site within the body cavity, wherein the optimal site promotes effective adhesion formation to control bleeding.

The present invention further contemplates a pretreatment device for creating trauma to a tissue within a body cavity. The pretreatment device generally includes a stem section and a trauma-inducing section adjacent to the stem section. In another embodiment, the pretreatment device comprises a pretreatment fluid and a flexible tube housed within a catheter and used to insult the tissue with the pretreatment fluid.

The present invention also contemplates a method of contraception. In general, the method comprises inserting an implantable device within a uterus and locating the device at an optimal site within the uterus. The optimal site promotes adhesion formation and prevents conception.

In addition, the present invention also contemplates a tool used to deploy an implantable device within a uterus. In one embodiment, the tool comprises a cervical cap and a guide located on a proximal end of the cervical cap. In an alternate embodiment, the tool comprises one or more expanding elements attached to the implantable device and one or more manipulator elements. In another embodiment, the tool is used to deploy an implantable device and comprises a guide directed for placement of the implantable device within the uterus to create adhesions.

The present invention also contemplates a device for monitoring the tissue of a uterus comprising at least one imagable marker. The marker has a size that is less than a size of an unexpanded uterus and a surface for adhering the marker to a uterine wall. In addition, the marker is composed of a biocompatible material suitable for permanent implantation is the uterus.

The present invention also contemplates method of monitoring tissue of the uterus comprising introducing at least one imagable marker into the interior of the uterus and allowing the at least one marker to become embedded in tissue formed on the interior of the uterus. The method also includes using the at least one marker as a reference location to evaluate tissue features on the interior of the uterus. In addition, the at least one imagable marker is introduced into the interior during a procedure wherein the uterus is being treated for a condition of menorrhagia. Alternatively, the method may also include at least two imagable markers that are introduced into the uterus and wherein the at least two imagable markers provide a two dimensional frame of reference.

BRIEF DESCRIPTION OF THE DRAWINGS

Other features and advantages of the present invention will be seen as the following description of particular embodiments progresses in conjunction with the drawings, in which.

DETAILED DESCRIPTION OF THE INVENTION

Figure 1:
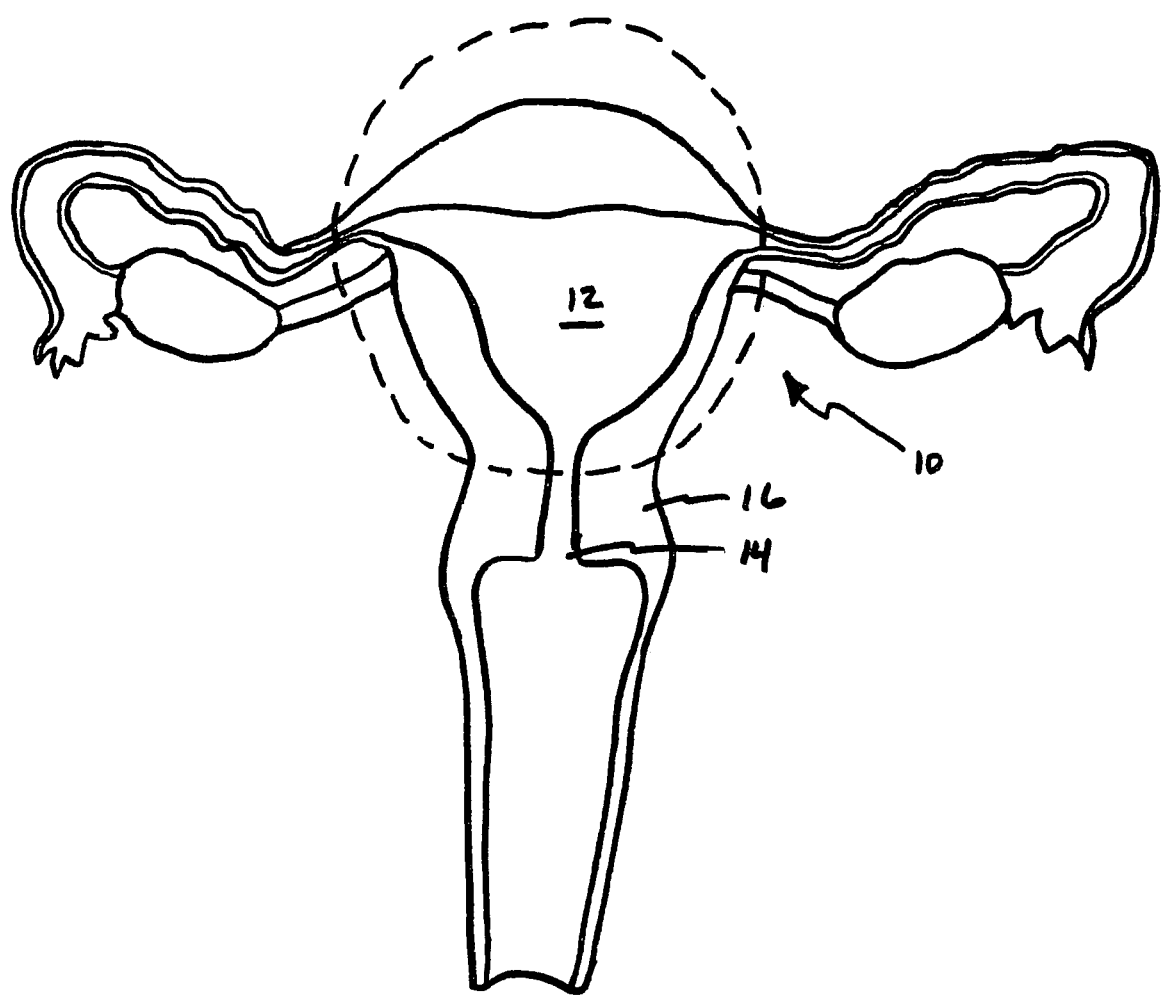
FIG. 1 is a sectional view of an embodiment of a hysterectomy.
Figure 2:
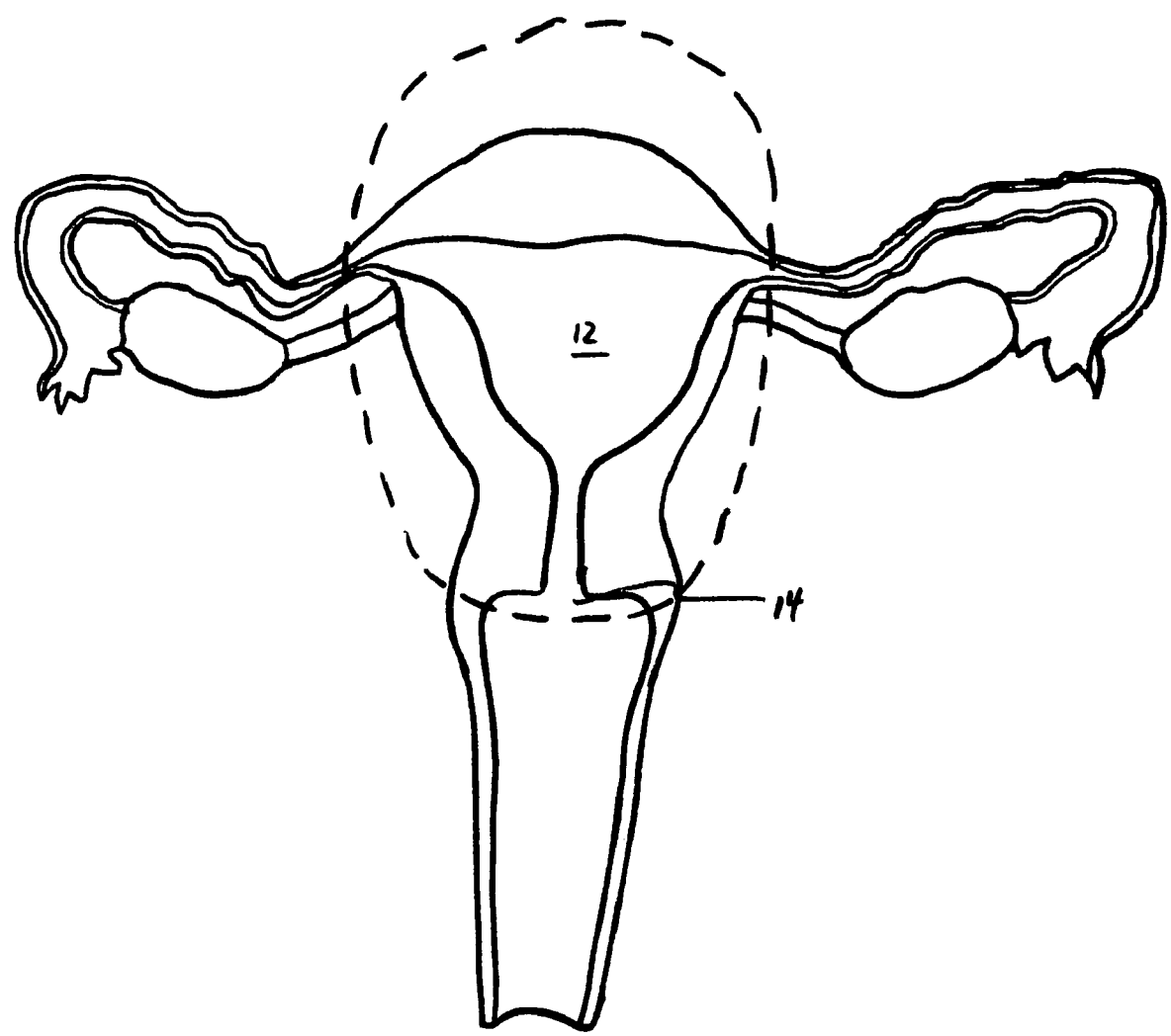
FIG. 2 is a sectional view of another embodiment of a hysterectomy.
Figure 3:
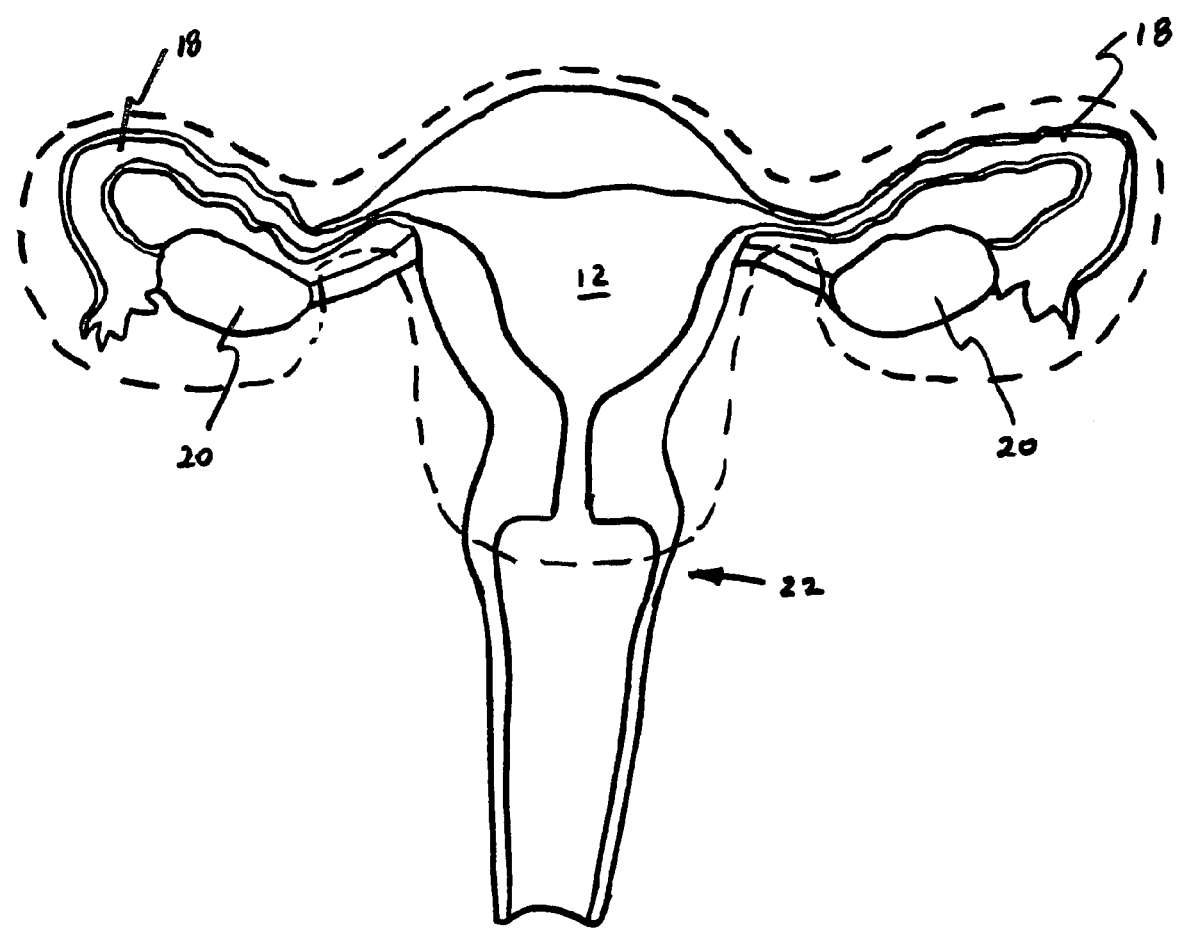
FIG. 3 is a sectional view of yet another embodiment of a hysterectomy.
Figure 4:
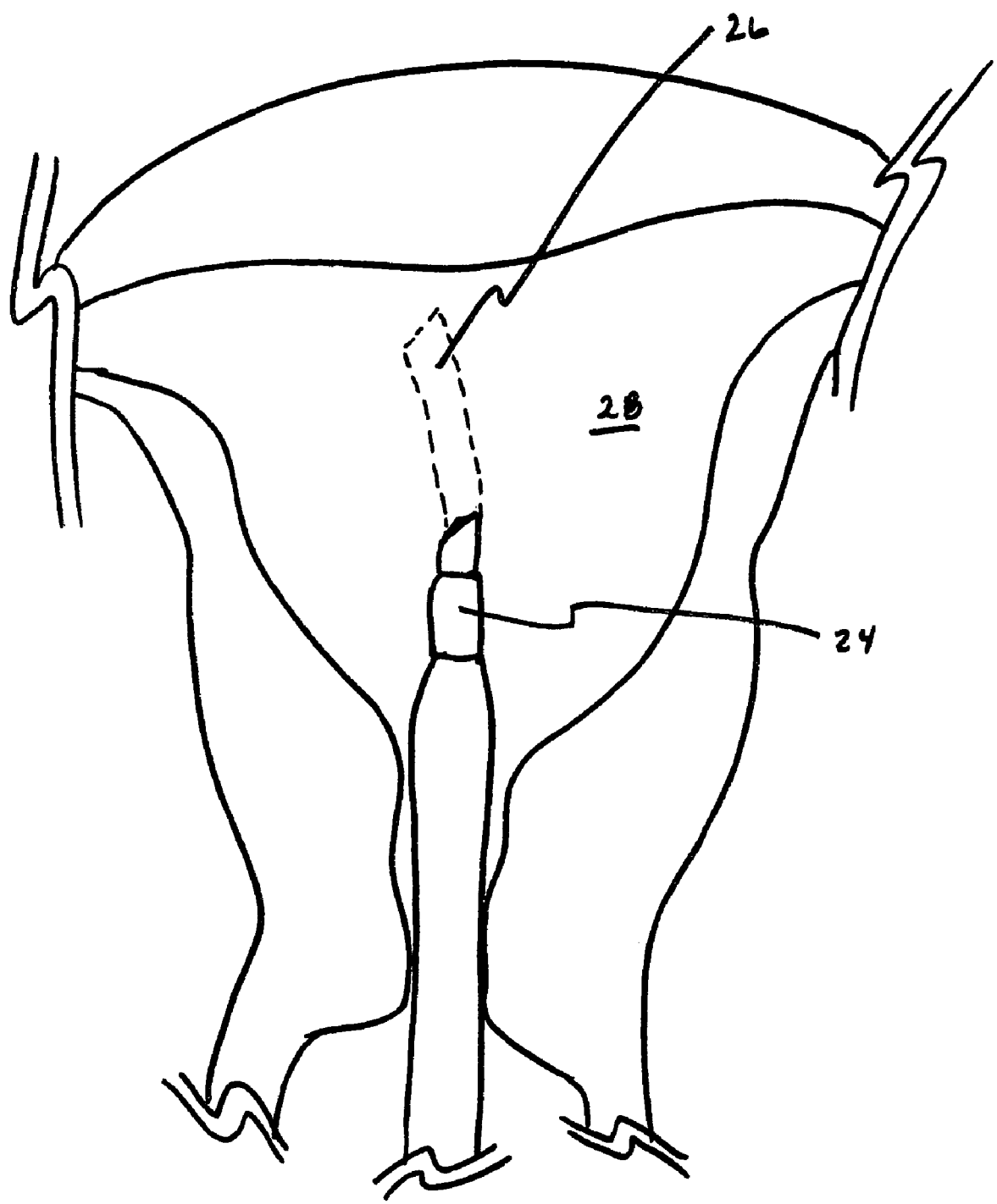
FIG. 4 is a perspective view of one embodiment of an ablation procedure.
Figure 5:
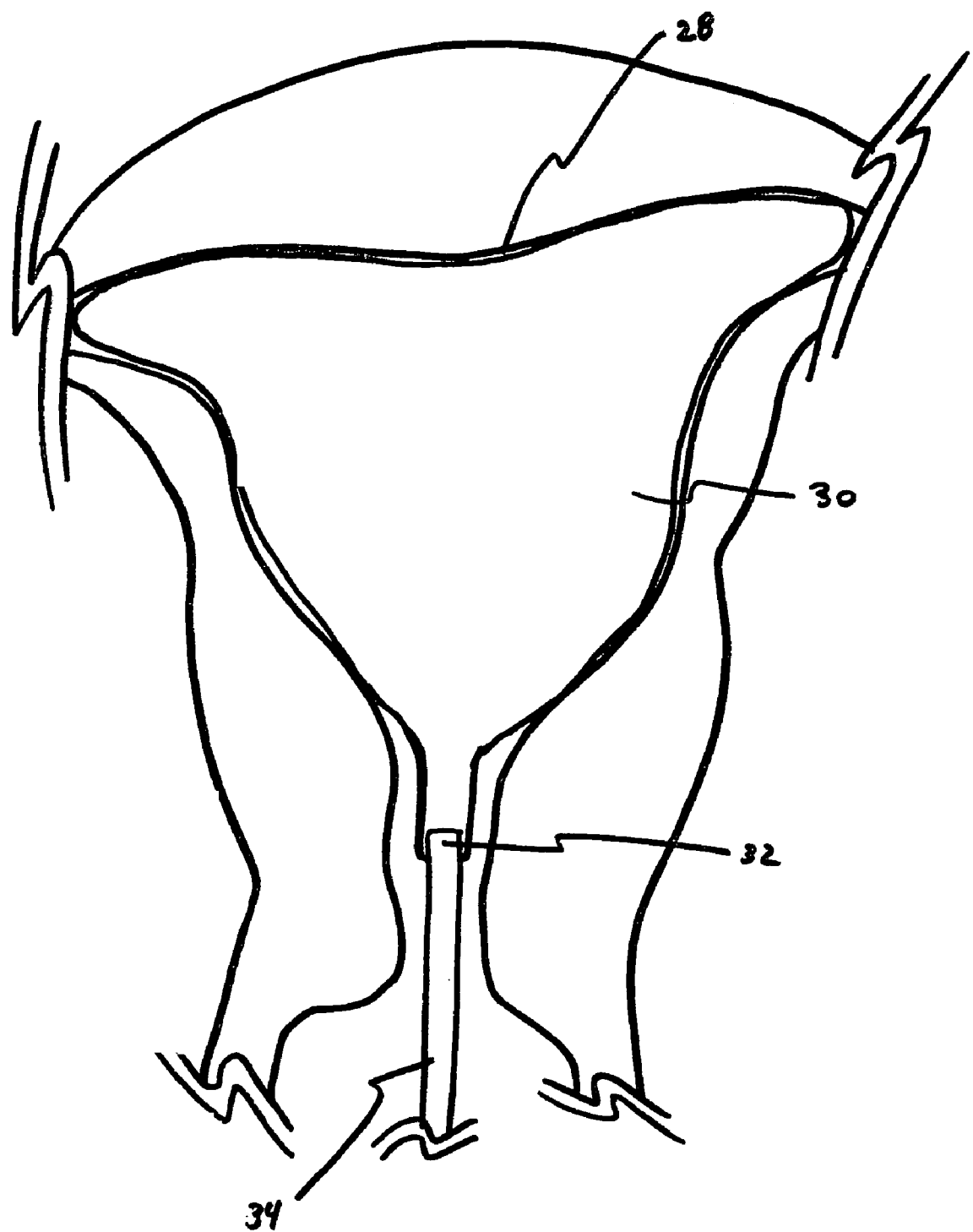
FIG. 5 is a perspective view of another embodiment of an ablation procedure.
Figure 6:
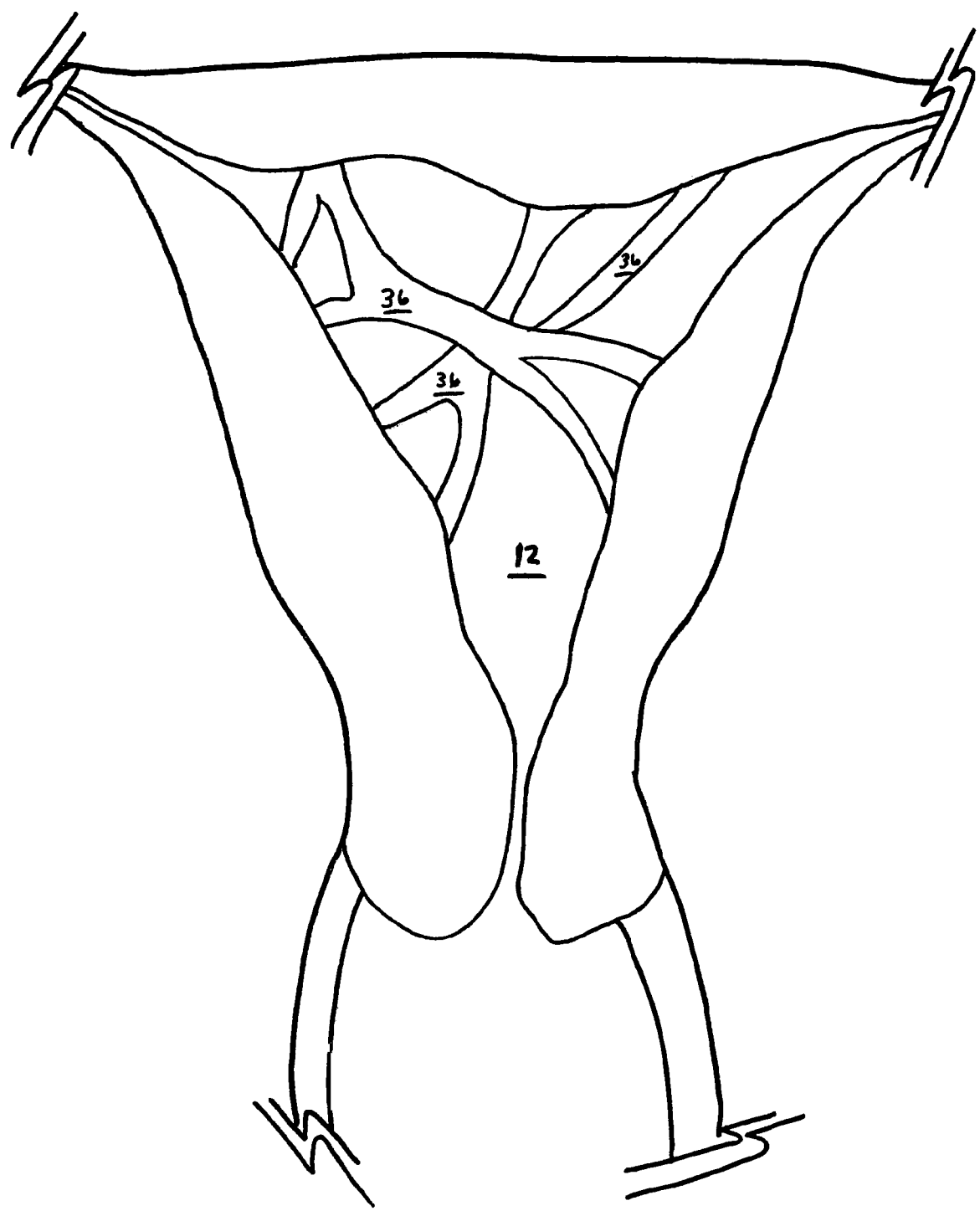
FIG. 6 is a perspective view illustrating intrauterine adhesions associated with Asherman's Syndrome.
Figure 7:
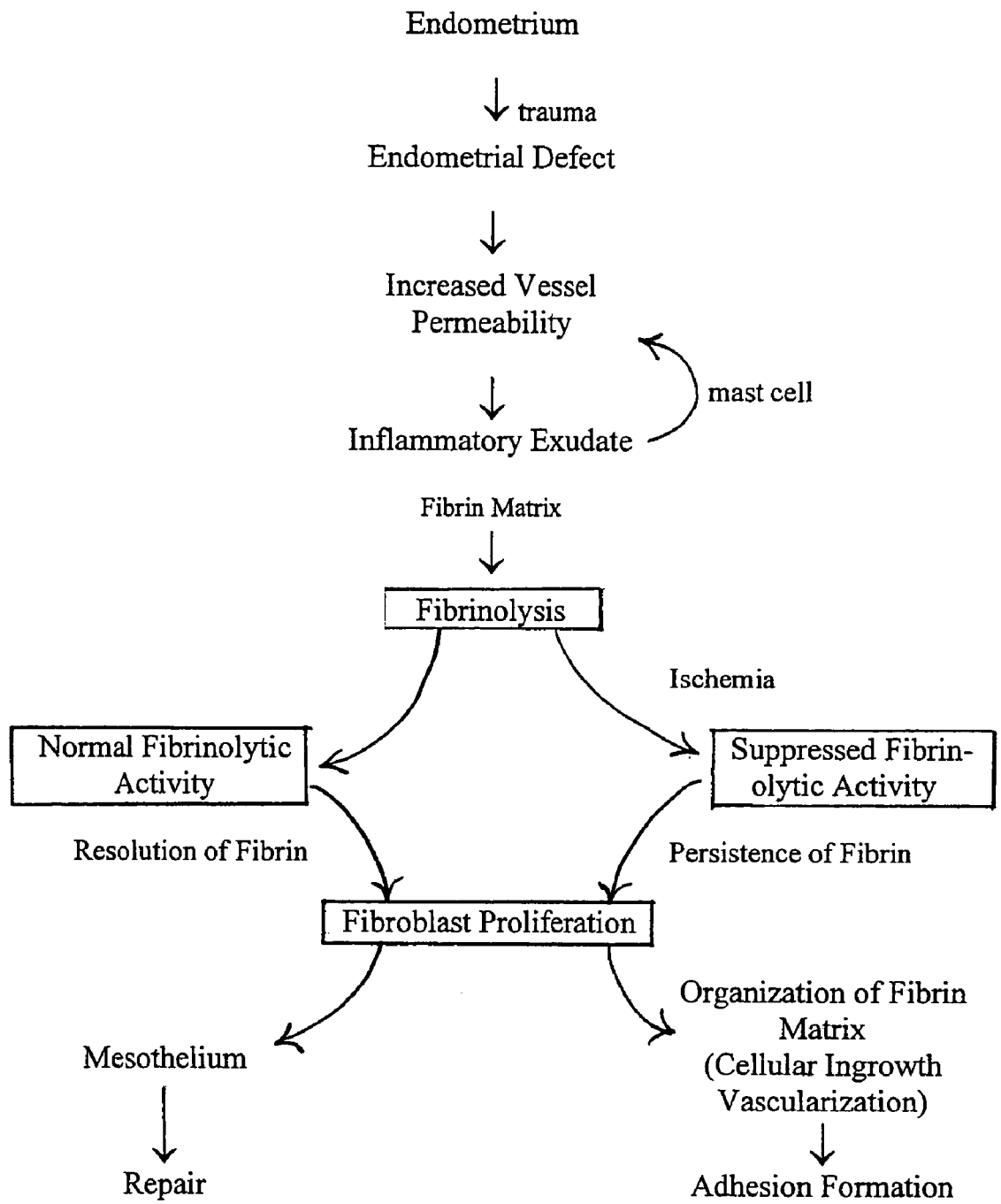
FIG. 7 is a general diagram illustrating the process of adhesion formation.
Figure 8:
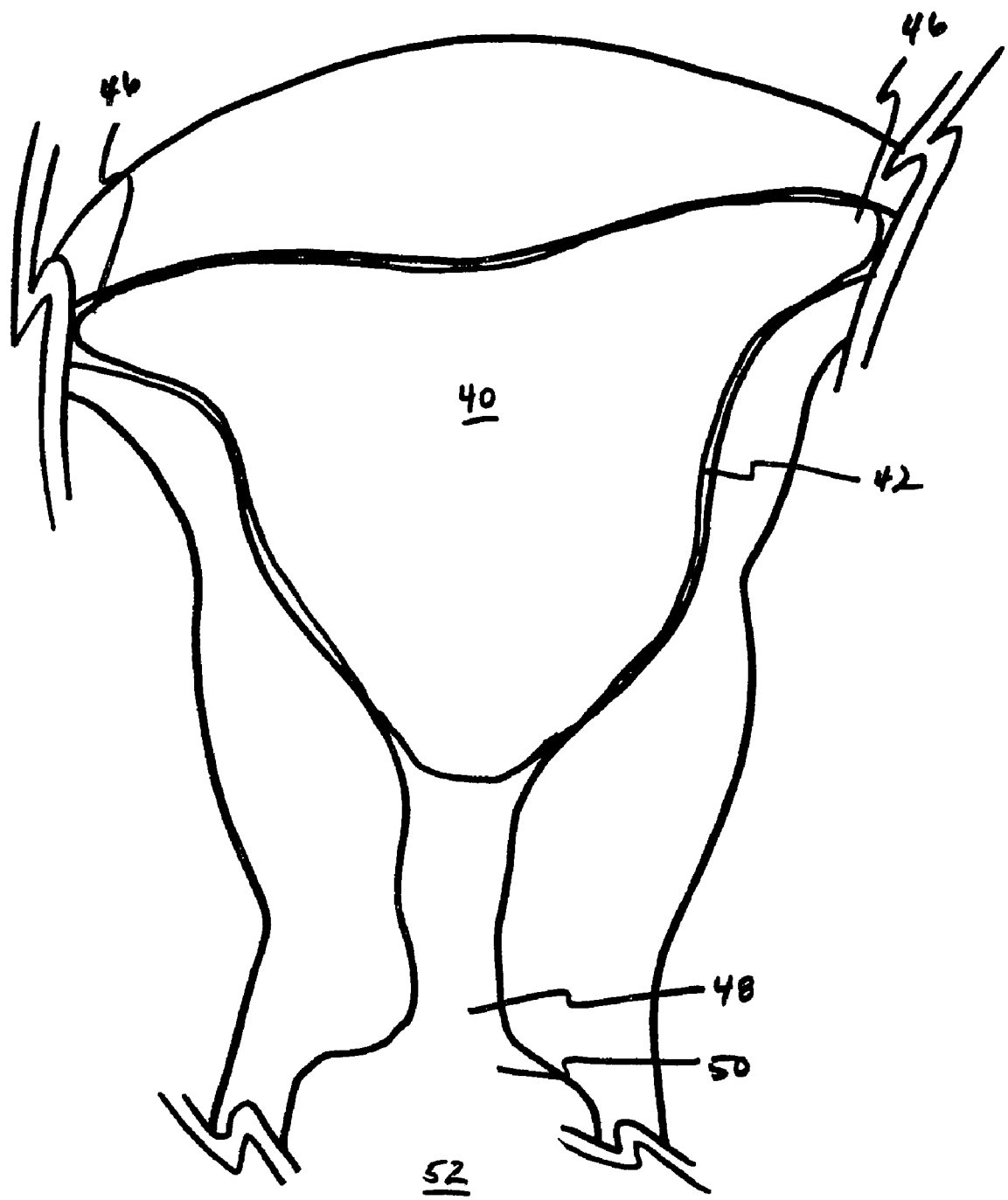
FIG. 8 is a perspective view of an embodiment of the intrauterine implant device in accordance with the present invention.
Figure 9A:
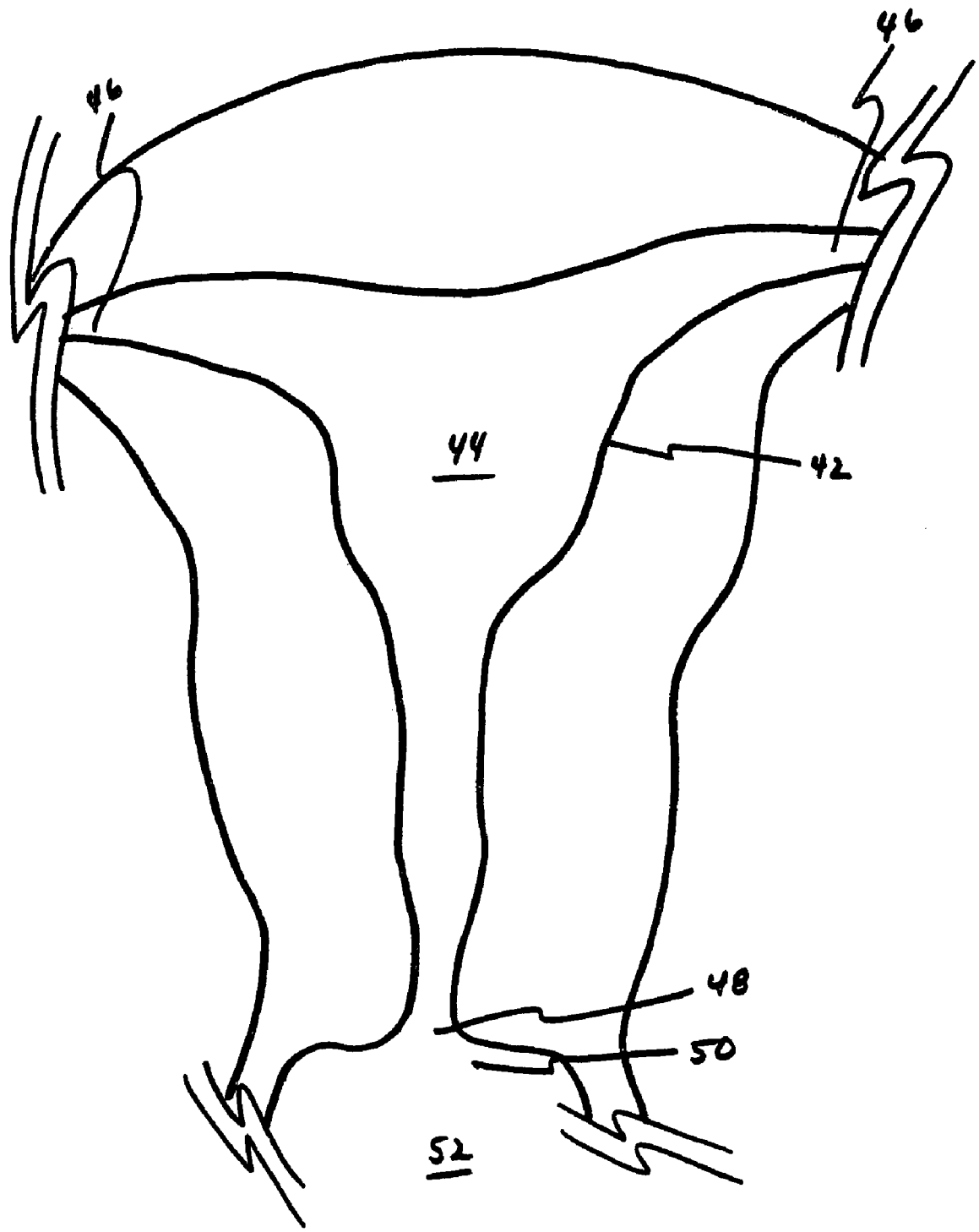
FIG. 9A is a front perspective view of a uterine cavity in a non-distended state.
Figure 9B:
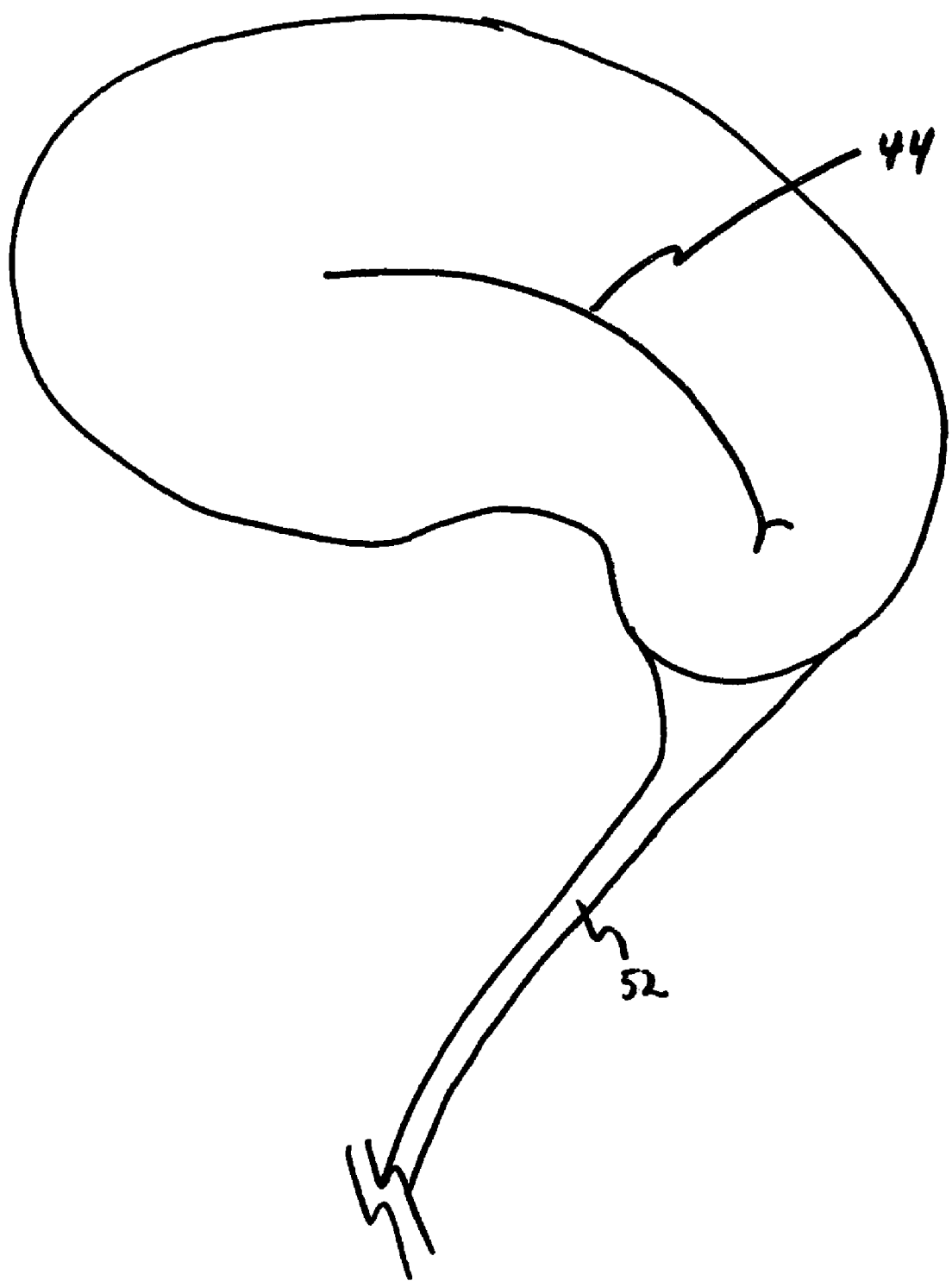
FIG. 9B is a side perspective view of a uterine cavity in a non-distended state.

Referring to FIG. 8, an embodiment of the intrauterine implant device 40 in accordance with the present invention is shown deployed within a uterus 42. The uterus 42, or womb, is part of the female internal genitals. The uterus 42 is a hollow, muscular organ approximately four inches long and three inches wide and is generally shaped like an upside-down pear. It should be noted that the uterus 42 depicted in FIG. 8 is in a distended state to clearly show the uterine cavity 44. However, it is understood that the uterine cavity is normally in a collapsed state, as shown in FIGS. 9A and 9B.

Two openings 46 located at the upper end of the uterus 42 lead to the Fallopian tubes that are connected to the ovaries (not shown). Opposite to the upper end openings 42 is a lower, narrow open end 48 that forms the cervix 50 of the uterus 42 and extends to the vagina 52. The thick walls of the uterus 42 are comprised of three layers of tissue and muscle: the inner endometrial layer, the middle myometrial layer and the outer perimetrial layer. It is the inner endometrial layer or lining that separates from the uterus 42 and leaves the body as the menstrual flow during a woman's menstrual period.

Excessive menstrual flow or bleeding, termed menorrhagia, is indicative of abnormal sloughing of the endometrial tissue layer. Unlike conventional therapies such as hysterectomy or ablation/resection procedures, as described above, the device 40 of the present invention achieves amenorrhea (i.e. cessation of bleeding) by way of an implant or substance that promotes formation of intrauterine adhesions. The intrauterine adhesions cause cessation of bleeding by a deactivation of the endometrial tissue, due to possibly a pressure gradient or neuro-modulating effect. Occlusion or obliteration of the uterine cavity may result. It is important to note that the endometrial tissue is deactivated through means other than the direct destruction of the lining, and that endometrial deactivation has been seen even in the presence of a small number of adhesions.

In general, the device of the present invention comprises a biocompatible material that is deliverable within a body cavity, such as the uterus. The material contains an attribute promoting tissue growth that results in adhesion formation within the body cavity. The attribute may be defined by a mechanical component and/or a non-cultured biologic component, further described below. Although the invention as disclosed herein generally refers to a uterus, other body cavities, such as cavities within a heart, abdomen or other similar cavities, are also included within the scope of the present invention.

Figure 10:
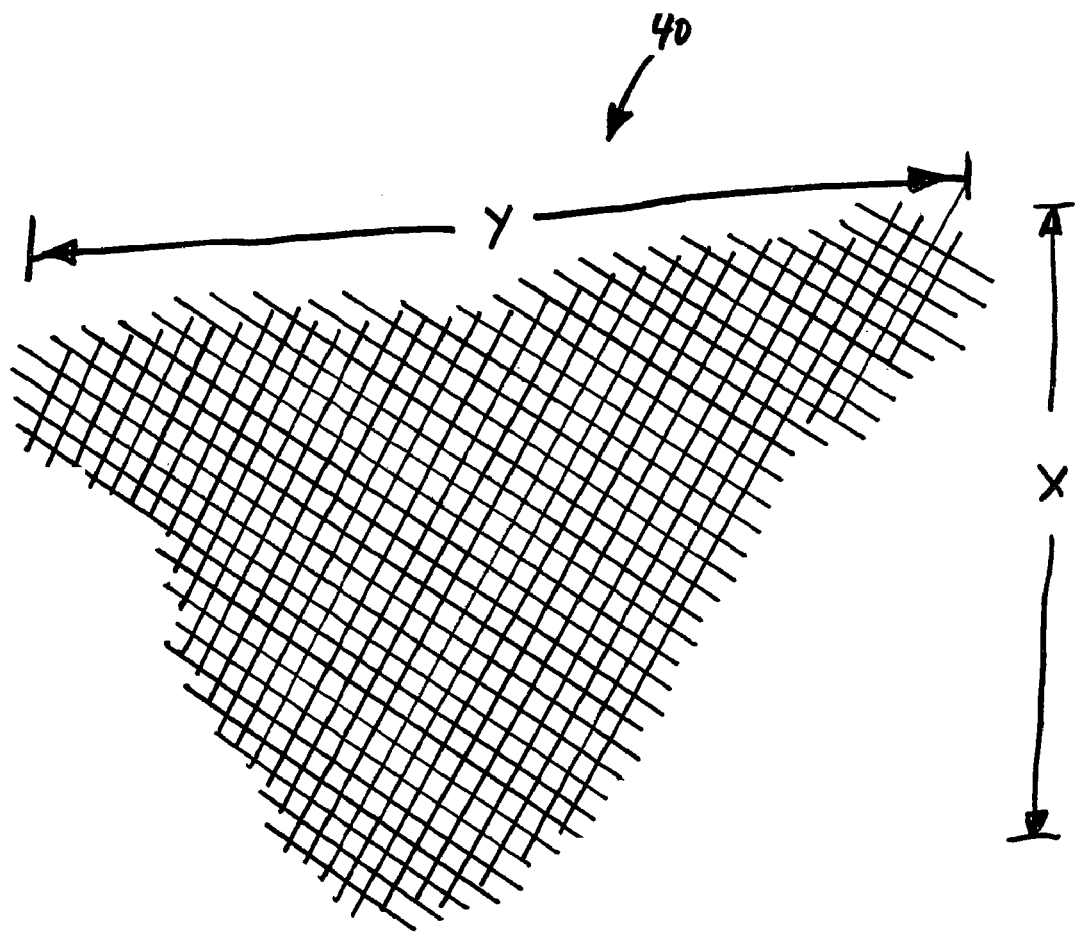
FIG. 10 is a perspective view of an embodiment of the intrauterine implant device in accordance with the present invention.

As shown in FIGS. 8 and 10, one embodiment of the device 40 of the present invention comprises a sterile material generally shaped or having physical properties to conform to the internal structure of the uterine cavity 44. In general, the device material may be flexible, rigid or semi-rigid and sized to fit within the uterus 42 of a patient. As such, the device 40 should be more or less triangularly shaped, having a height, X, of approximately 7 inches (17.78 cm) and a base, Y, of approximately 4 inches (10.16 cm). In an alternate embodiment (not shown), the device 40 comprises a flowable liquid or material that conforms to the uterine anatomy following device delivery.

Device Materials

The device 40 of the present invention can be made from a wide variety of materials including, but not limited to, mesh, suture, gel, porous, allograft, protein, hydrogel, liquid sealant, glue, cellulose, alginate, tissue, kitosan, particulate, foam and any combination of materials. The properties or characteristics of these materials may be non-absorbable, temporary/absorbable, whereby the material is broken down by the body through any means including enzymatic, hydrolytic, mechanical, etc. and excreted, or permanent/resorbable, whereby the material is remodeled through some process to form host or other similar tissue. In addition, the device material should be biocompatible, non-toxic and, preferably, one that is approved/cleared by the Food and Drug Administration (FDA) and has been used for a long period of time in humans with the purpose of creating adhesions. Further, for embodiments of the device 40 having a mechanical configuration, it is desirable that the material be capable of conforming to irregular volumes and/or shapes. In general, the device 40 should be designed such that it can be placed in, stored in and deployed from a catheter or similar device delivery tool.

In one embodiment, the material is a woven, surgical mesh. Alternatively, the mesh can be braided, spun, knitted, non-woven and any structural combination thereof. Examples of representative surgical meshes include GORE-TEX® (manufactured by W.L. Gore & Associates, Arizona), Marlex® (manufactured by C. R. Bard, New Jersey), Mersilene® (manufactured by Johnson & Johnson, New Jersey), Prolene® (manufactured by Johnson & Johnson, New Jersey), Surgipro® (manufactured by US Surgical, Connecticut), Surgisis® (manufactured by SIS Technology Cook Group, Indiana), Vicryl® (manufactured by Johnson & Johnson, New Jersey) and Atrium Surgical Mesh (manufactured by Atrium, New Hampshire). Specific references for these materials may be found in the manufactures' product catalogues. Additional surgical mesh materials such as polyester, felt, polyethylene fiber, non-absorbable mesh, PTFE (Polytetrafluoroethylene), absorbable mesh and other mesh materials not specifically disclosed herein may also be used to create or enhance the development of intrauterine adhesions 36.

In general, these materials are typically used for creation of adhesions or tissue repair within other regions of the body. One example of such use is hernia repair, whereby a specialized mesh or screen is used to hold the hernia in place. For this application, the material acts like a plug and soon becomes incorporated by the surrounding tissue to strengthen the weakened area.

Although select literature references describe some of the materials as being adhesion barriers, these materials are in fact very good at creating adhesions under specific circumstances. One such example is Surgicel® oxidized regenerated cellulose (manufactured by Johnson & Johnson, New Jersey), which is considered an adhesion barrier material and, in certain circumstances, an adhesion creator/promoter. Therefore, both adhesion barrier and adhesion promoter materials may be used for the device 40 of the present invention.

In another embodiment of the invention, the implant 40 is made of a woven material, such as a fabric with a specific weave, that is also biocompatible. In this configuration, the material of the device creates a lattice-like structure (having openings or pores) that promotes infiltration of fibrous tissue, resulting in adhesions 36. The material may be metallic, polymeric or a bio-material (including combinations of materials) and can be absorbable or non-absorbable, depending on the physical and procedural requirements. Additional material specifications or variables may include type of weave (such as plain, open, closed, twill, dutch, reverse dutch, twill dutch, or taffeta, including combinations of weaves), mesh count, fiber diameter, filament type (such as monofilament fiber or multi-filament fiber) or whether there are interconnection of weave points. A reference containing additional specifications, variables and general information on woven materials is Sefar America, Inc., Depew, N.Y. (sales literature booklet, dated 1998), which is incorporated herein by reference.

Figure 11:
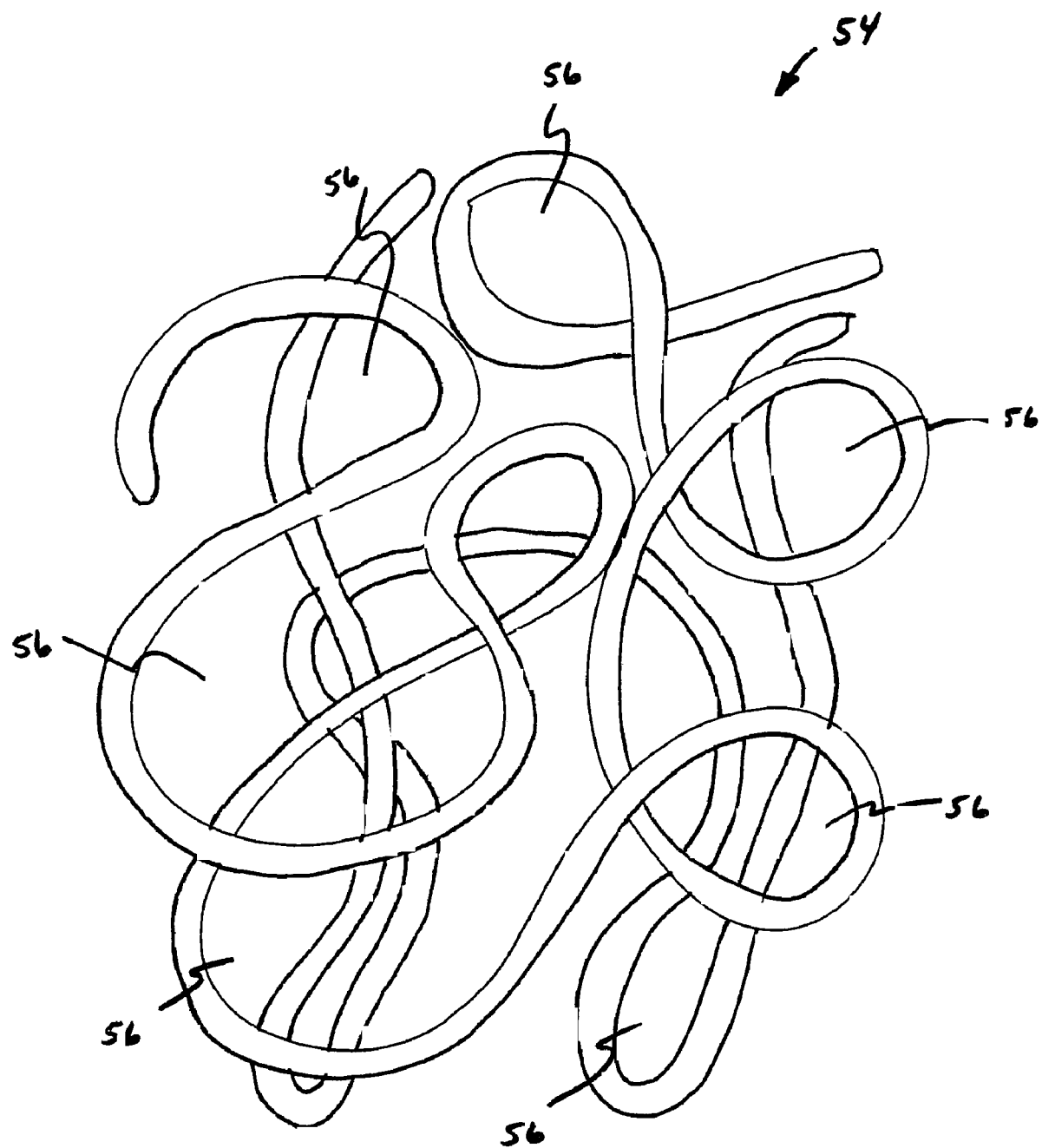
FIG. 11 is a perspective view illustrating an embodiment of a random fiber bundle in accordance with the present invention.

Alternatively, the device 40 of the present invention can also be made of non-woven materials. One type of non-woven material is a random fiber bundle 54. The fiber bundle 54 may be a thin mat, similar to a woven mesh, with an irregular fiber pattern. Examples of materials having an irregular fiber pattern include Scotchbrite® or Brillo® pad materials. In addition, the material may be fabricated from any monofilament or multi-filament material. An example of a monofilament material that can be used for the implant is suture material, such as Prolene® or Vicryl® (manufactured by Johnson & Johnson, New Jersey). Although the fibers of the non-woven material are arranged in a random orientation, the configuration of the fibers produces an associated effective pore size 56, shown in FIG. 11. Additional examples of non-woven materials include all the materials listed above, since materials fabricated into a woven product can also be manufactured into a random fiber bundle 54.

Numerous manufacturing methods and associated techniques may be used to fabricate the woven and non-woven materials used in the device 40 of the present invention. For example, in one embodiment, a monofilament having a thickness within the range of 0.003 to 0.007 inch (0.00762 cm to 0.01778 cm) is cut into 0.118 inch to 0.197 inch (0.3 cm to 0.5 cm) segments. The segments are then shaped into a predetermined configuration, such as a sphere or a cube. The porous individual shapes are then arranged into the final material design. The porosity of the resultant material is dependent on the size and shape of the fibers and the amount of compression (density) of the fibers. Examples of other manufacturing techniques within the scope of the present disclosure include heating, ultrasonic cutting, cold cutting, ultrasonic welding, injection molding, compression molding, stamping, drawing, forming and other techniques not specifically disclosed, but well known in the art.

In another embodiment, the device 40 of the present invention is made of porous materials. Examples of such porous materials include, but are not limited to, ceramics, alumina, silicon, powdered metals, Nitinol®, stainless steel, titanium, porous polymers, such as polypropylene, polyethylene, acetal, nylon, polyester, and any combination of such materials. Although these materials (and others not specifically described, but included in the scope of the claimed invention) may not be inherently porous, various manufacturing and processing techniques may be used to give the materials selective porosity characteristics.

In addition, one or more of these materials may be further incorporated into a mesh matrix (i.e. porous fibers woven into a mesh or configured in a random orientation). Alternatively, the materials can be configured as many particles of equal or different size or shape that are constructed into a matrix. In another embodiment, the polymeric materials may be manufactured to form a sponge-like material with open pore cells. This sponge-like configuration not only promotes adhesions 36, but also allows the implant 40 to better conform to the internal area of the uterine cavity 44. Specific examples of such materials include Ivalon, a polyvinyl sponge (manufactured by C. R. Bard, New Jersey) and Surgifoam® (manufactured by Johnson & Johnson, New Jersey). However, it should be noted that other materials not specifically listed herein may also be used.

Both the size of the pores of the material as well as the material's physical characteristics have an impact on the effectiveness of the implant 40. These material attributes determine the type of tissue that will develop or grow into the mesh and, ultimately, the type of adhesion 36 that will form within the uterus 42. The direct correlation between these parameters for treatment of menorrhagia can be determined from existing material classifications or types based on tissue in-growth, such as those used for hernia repair. For example, Type I includes materials with pore sizes greater than 75 microns which allows for growth of macrophages, fibroblasts (fibroplasias), blood vessels (angiogenisis) and collagen fibers into the pores. This pore size is similar to the pore sizes found in Prolene® (manufactured by Johnson & Johnson, New Jersey), Marlex® (manufactured by C. R. Bard, New Jersey) and other meshes described above. As such, Type I materials are suitable device materials.

Type II materials are micro-porous meshes with pore sizes less than 10 microns in at least one of three dimensions. Materials such as GORE-TEX® (manufactured by W.L. Gore & Associates, Arizona), PTFE and other surgical membranes are typical examples of these meshes. Thus, Type II materials are also appropriate device materials.

Type III materials contain multi-filaments and include macro-porous and/or micro-porous components. In general, Type III materials have varying pore sizes and are a combination of Type I and Type II materials. Several examples of Type III materials include Dacron mesh (such as Mersilene®, manufactured by Johnson & Johnson, New Jersey), braided polypropylene mesh (such as Surgipro®, manufactured by US Surgical, Connecticut), and perforated PTFE (such as GORE-TEX® MYCROMESH®, manufactured by W.L. Gore & Associates, Arizona). These and other Type III materials not specifically listed herein may also be used for the device 40 of the present invention.

In another embodiment of the invention, the device or implant 40 is fabricated from a liquid sealant or glue, such as collagen, tissue/collagen, thrombin, polymer, fibrin-based sealants and any combination thereof. In general, these materials are typically configured in a liquid format. However, collagen is a very common substance and may be found in numerous configurations, including flour, compressed mat pad, non-woven fiber or other molded, extruded or compressed shapes with varying density and/or porosity. Examples of collagen and tissue/collagen materials contemplated herein include Avitene® (manufactured by C.R. Bard, New Jersey), Helitene® (manufactured by Integra Life-Sciences Corporation, New Jersey), Dermalogen®, Dermaplant™ (manufactured by Collagenesis, Inc, Massachusetts), Apligraf®, Engineered Collagen Matrix™ and Vitrix™ (manufactured by Organogenesis Inc., Massachusetts). The collagen may be synthesized or derived from bovine, porcine or human sources.

An example of a collagen-thrombin sealant is Costasis®. Costasis®, manufactured by Cohesion Technologies, California, is a collagen-thrombin composite for use as a hemostatic agent to arrest or control bleeding at various sites within the patient's body. This material is comprised of bovine fibrillar collagen and bovine thrombin suspended in calcium chloride. At the time of application, fibrinogen (taken, for example, from the patient's plasma) is mixed with the Costasis®, thereby providing fibrinogen that is cleaved by the thrombin to form a collagen-reinforced liquid hemostat. The resultant liquid material may then be applied to the target site to control bleeding.

Alternatively, the physical properties of the liquid sealants may be altered to create hemostatic solids of specific shapes or pliable geometries. In one embodiment, the sealant material may be placed in a carrier matrix that has specific flow requirements and may be activated by heat or moisture to change the sealant's physical characteristics. An example of an appropriate carrier matrix is thrombin-based CoStop®, also manufactured by Cohesion Technologies, California. However, unlike Costasis®, CoStop® does not require plasma from the patient. Simply combining the patient's blood with the thrombin-based CoStop® is sufficient to cause platelet activation. As soon as the combination of blood and thrombin causes platelet activation, the thrombin further catalyzes the mixture to form a fibrin clot. As such, platelet activation initiates clot formation. A collagen-fibrin matrix develops, forming the basis or support-structure for the tissue that will be created at the target site. Thus, when used to treat menorrhagia, CoStop® is placed within the uterus 42 of the patient and forms the collagen-fibrin matrix. The newly formed tissue bridges together the posterior and anterior walls of the uterus 42, thereby creating an adhesion 36 and promoting amenorrhea.

Alternative methods and components may also be used to modify the physical properties of the liquid sealants. Although not specifically mentioned herein, these methods and components are well known in the applicable art and, therefore, are within the scope of the present disclosure and claimed invention.

In another embodiment, the device 40 of the present invention is made of allograft materials (i.e. a graft of tissue taken from a donor of the same species as the recipient). These materials use the structure and properties of the allograft tissue as a matrix for new tissue formation. Osteofil™ (manufactured by Regeneration Technologies Inc., Florida) is an example of one such material. The Osteofil® is placed within the uterus 42 of the patient and a fibrous tissue is formed within the matrix. This new tissue forms the basis for the adhesion 36. The allograft tissue from Regeneration Technologies Inc. is initially contemplated as demineralized bone; however, other tissues derived from animals or humans may also be used. In addition to Osteofil®, other similar materials including, but not limited to, Natural Matrix (Xenograft), such as OsteoGraf® N-Block (manufactured by Cera Med Dental, LLC, Colorado) and other tissues available from various accredited tissue banks are also within the scope of the claimed invention.

In yet another embodiment, protein materials are used to fabricate the device 40 of the present invention. Various companies and organizations have studied the use of proteins for creating both non-stick and attachable surfaces. One such company is Protein Polymer Technology located in San Diego, Calif. Protein Polymer Technology creates synthetic genes using recombinant DNA technology. In particular, Protein Polymer Technology is able to configure small protein building blocks into high molecular weight polymers.

Another company that uses proprietary technology to create application specific proteins is Gel-Del Technologies (St. Paul, Minn.). Gel-Del Technologies, like Protein Polymer Technology, and other similar companies process proteins using various methods. The physical structure and composition of the protein are modified to create a wide variety of properties for the protein. For example, proteins have been created that have cellular receptors, which promote active association or adhesion 36. The physical characteristics (for example, shape) of the protein and its side chain elements influence the development of a fibrous response and the formation of the desired adhesions 36. In particular, the available side chain elements regulate selective infiltration of tissue into the protein structure, thereby producing adhesions 36 at the tissue target site.

In general, proteins may be developed into a wide variety of formats. Examples of various protein formats include small beads, sheets, strips or other regular or irregular shaped configurations. The protein format allows the protein to be implanted in, for example, the uterus 42 to create the response necessary for adhesion formation.

In another embodiment of the invention, the device or implant 40 is fabricated from hydrogel materials. Hydrogels are coherent three-dimensional polymeric networks that can absorb large quantities of water without dissolution of the polymer network. Classes of hydrogels, based on their method of preparation, include homopolymer hydrogels, copolymer hydrogels, multipolymer hydrogels and interpenetrating hydrogels. In general, hydrogels are hydrophilic polymers incorporating Chitson derivatives or polyethylenimine together with polyvinylpyrrolidone (PVP). Hydrogels may also include cellulose derivatives, polyvinyl alcohol (PVA) or polyethylene glycol (PEG). An example of one common hydrogel is polyHEMA (poly(2-hydroxyethyl) methacrylate) These highly compatible water-soluble polymer systems naturally combine with each other to form gels possessing excellent physical properties. These properties may be varied by the chemistries of the gel (i.e. compounding), active ingredients and biomolecules, which can be readily incorporated without impairing biological activity. Virtually any material that can be dissolved, emulsified, or suspended can be added prior to gel-formation and evenly distributed in the finished gel.

The hydrogel Aquatrix™ II (manufactured by Hydromer, New Jersey) is an example of one such hydrogel product. The gel may be loaded with any of the above-mentioned materials, such as Marlex® (manufactured by C. R. Bard, New Jersey), Mersilene® (manufactured by Johnson & Johnson, New Jersey), Surgipro® (manufactured by US Surgical, Connecticut), Surgisis® (manufactured by SIS Technology Cook Group, or any other material that is pulverized, ground, etc. and combined with the hydrogel material. In this configuration, the hydrogel is acting as a carrier material to allow for dispensing of the scaffold or lattice material. The material can then be delivered as a flowable liquid with a suspension of particles. Further, the gel may be formulated to be absorbed or resorbed by the body within 30 to 60 days. However, the particle/mesh would remain, forming the desired adhesion 36 at the target site. In an alternate embodiment, the gel may be formulated to be non-absorbable. In the case of a non-absorbable gel, the gel may be placed at the target site and then blown with a gas to form small pores. The pores function in a manner similar to the mesh openings or pores, allowing in-growth of tissue and, ultimately, forming adhesions 36.

In general, the materials used with the device 40 of the present invention may be comprised of a combination of absorbable and/or non-absorbable materials or components. In one embodiment, the absorbable material may be comprised of a radio-opaque marker, or any other type of imagable marker, that allows the target site to be imaged. In another embodiment, the absorbable material may be used to fixate the non-absorbable material at the target site in the patient. For example, the absorbable material may be configured as a cervical cap. The cervical cap is inserted at the time of implantation of the device 40 and holds the device 40 in-place within the uterus 42. Within approximately 8 weeks, adhesions 36 form and the body of the patient absorbs the absorbable material of the device 40.

Method of Use

Many methods for creating intrauterine adhesions 36 are contemplated herein. Each methodology has a slightly different mechanism for creating adhesions 36. As explained above, only a limited understanding of the actual mechanism for adhesion creation is currently known. However, it seems that intrauterine adhesions 36 perform the same function of producing amenorrhea.

In one embodiment, the size and/or configuration of the device 40 is optimized to promote effective adhesion development within the uterus 42. In another embodiment, the device 40 is configured to contact substantially the entire area of the endometrium to maximize the yield (i.e. up to 100% coverage) of adhesions within the uterus 42. Alternatively, there may be optimal locations within the uterus 42 for site-specific deployment and/or placement of the device 40. As such, the implant 40 need only contact specific or discrete areas of the endometrium for effective adhesion formation (i.e. adhesions in less than 100% of the endometrium). For example, the device 30 may be located in the cervical canal, and not the uterus 42, to produce sufficient adhesions 36 to control bleeding. As another example, the device 40 may be positioned at a specific site only within the uterus 42. Alternatively, a combination of uteral and cervical locations may be used for beneficial adhesion formation.

In another embodiment of the invention, the implant or device 40 may include a means for assessing and determining specific areas in the uterus 42 that are areas of excessive bleeding. These discrete areas may then be treated to specifically form adhesions 36 at these target sites. This approach allows the endometrium to remain viable and, simultaneously, reduces and/or controls bleeding. Since the endometrium is not completely obliterated, this method may allow for reversal of the procedure (i.e. removal of adhesions). Research has shown that adhesions 36 may be removed and, thus, uterine viability restored.

In general, the method of use or treatment system of the present invention is contraceptive in nature. The device or implant 40 creates intrauterine adhesions 36 which deactivate the endometrial tissue. In addition, the adhesions 36 may also obstruct the Fallopian tubes and/or the entrance to the Fallopian tubes. This, in turn, eliminates the possibility of pregnancy (i.e. prevents conception) and childbearing. However, if only a limited area within the uterus 42 requires formation of adhesions 36, the procedure and its associated effects may be reversed. Therefore, if the adhesions 36 are not extensive, it is possible to restore menstrual function, and the potential of pregnancy, to the uterus.

Adhesion formation or coverage is important not only in placement of the coverage (which is related to device placement) but also percentage of coverage. Although the device 40 and methods referenced herein are directed at creating 100% coverage of adhesions 36 over the entire area of the endometrium, it should be understood that alternative device configurations and methods of use relating to less than 100% adhesion and/or endometrial area coverage are also contemplated herein. For example, in general, the percent of coverage must be greater than 75% and/or the placement of coverage should be within the lower two-thirds of the uterus and/or the entire cervical canal. Other coverage options, though not specifically described herein, are also included within the scope of the claimed invention.

The general adhesion formation is a localized response to an inflammatory condition and foreign body (i.e. intrauterine device 40). The curettage or other pretreatment (further discussed below) causes trauma to the endometrium and initiates an inflammatory response. The body then begins to create fibroblasts (connective tissue) at the injury sight as means to heal the trauma). These fibroblasts continue to respond to the localized inflammation creating more and more fibrous tissue. As the fibrous tissues are created, the posterior and anterior walls of the uterus 42 are joined more closely by the scar tissue. The myometrial cells eventually infiltrate the scar tissue and the surrounding tissue reabsorbs the endometrium. Long-term deactivation of the endometrial tissue is believed to be due in part to the increased intrauterine pressure created by the adhesions 36. There are also other modulating factors, not specifically described herein, that may contribute to the deactivation of the endometrium.

In addition to creating permanent intrauterine adhesions 36 and treating menorrhagia, the intrauterine device 40 of the present invention can also be used on a temporary basis or as a lifestyle choice. The disclosed implant device/system 40 could also offer women the option of whether or not to have periods. Thus, the device 40 may be used as a convenience to women to end their menstrual periods without having to undergo major surgery. Further, the device 40 may be used to eliminate painful menstrual cycles or premenstrual symptoms. As yet another alternative, the device 40 may be used as a temporary means of contraception. When a woman is ready to have children, the procedure could be reversed, whereby the adhesions 36 are removed and menstruation returns.

Pretreatment

In one embodiment of the invention, the methodology used to create adhesions 36 involves pretreatment of the endometrium prior to placement of the device 40 in the uterus 42. The pretreatment method may be either direct or indirect. Generally, indirect pretreatment occurs during the time period prior to the procedure. In contrast, direct pretreatment occurs during the actual procedure.

Direct pretreatment (via mechanical means, chemical means or a combination thereof) is performed in order to invoke a healing response from the uterus 42. One type of direct pretreatment involves creating trauma to the endometrium prior to deployment of the device 40. Methods to achieve this trauma and, in some instances, necrosis of tissue may include curettage or a form of endometrial ablation. These methods may be performed with a sharp or blunt curette (vacuum curettage), roller ball electrocautery device, thermal energy device (such as re-circulating hot water), hot water filled balloon, radio-frequency (RF) energy director, microwave, cryogenic device (to freeze the tissue), cytotoxic agent, intense LASER light and other devices capable of imparting trauma to the endometrial lining, including combinations of such devices.

Figure 12B:
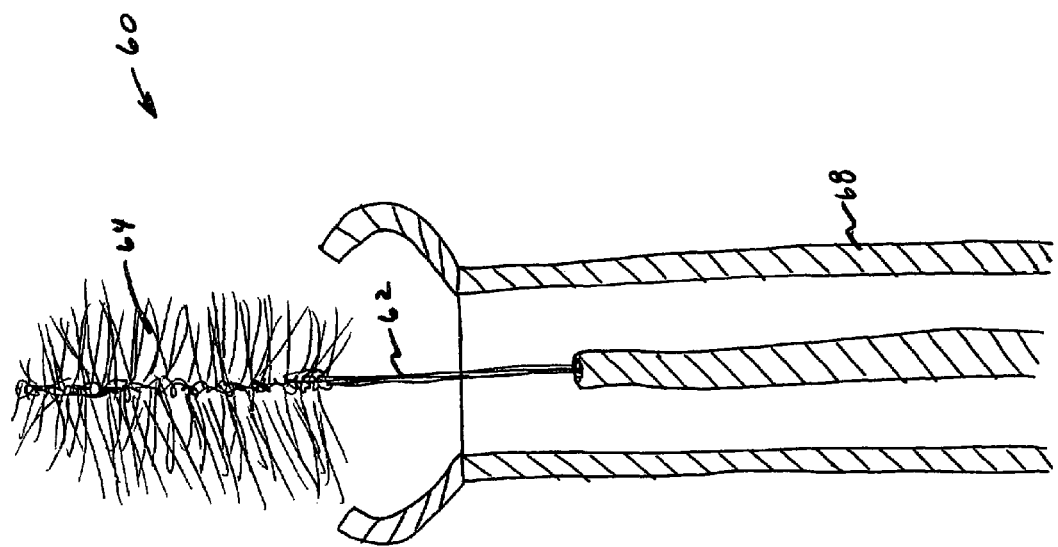
FIGS. 12A-12F illustrate various embodiments of a pretreatment device in accordance with the present invention.
Figure 12A:
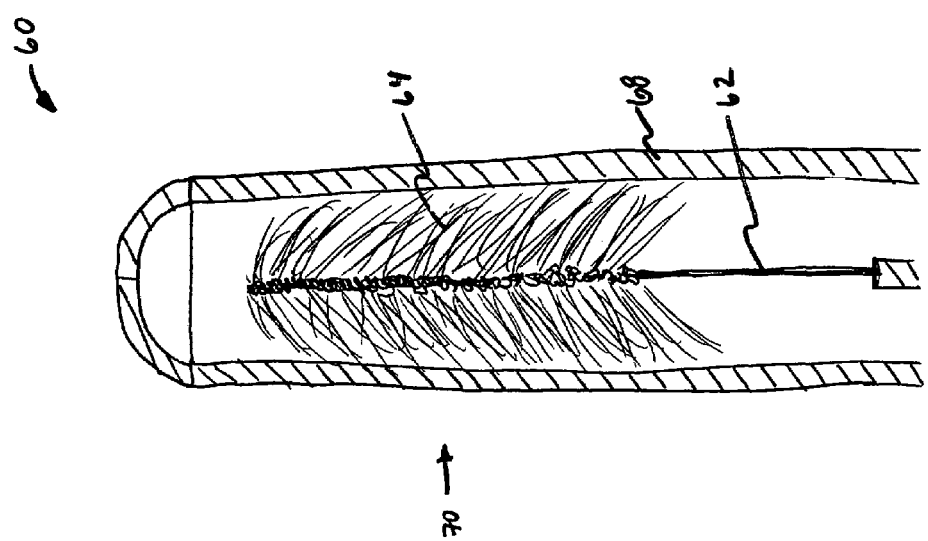
Figure 12C:
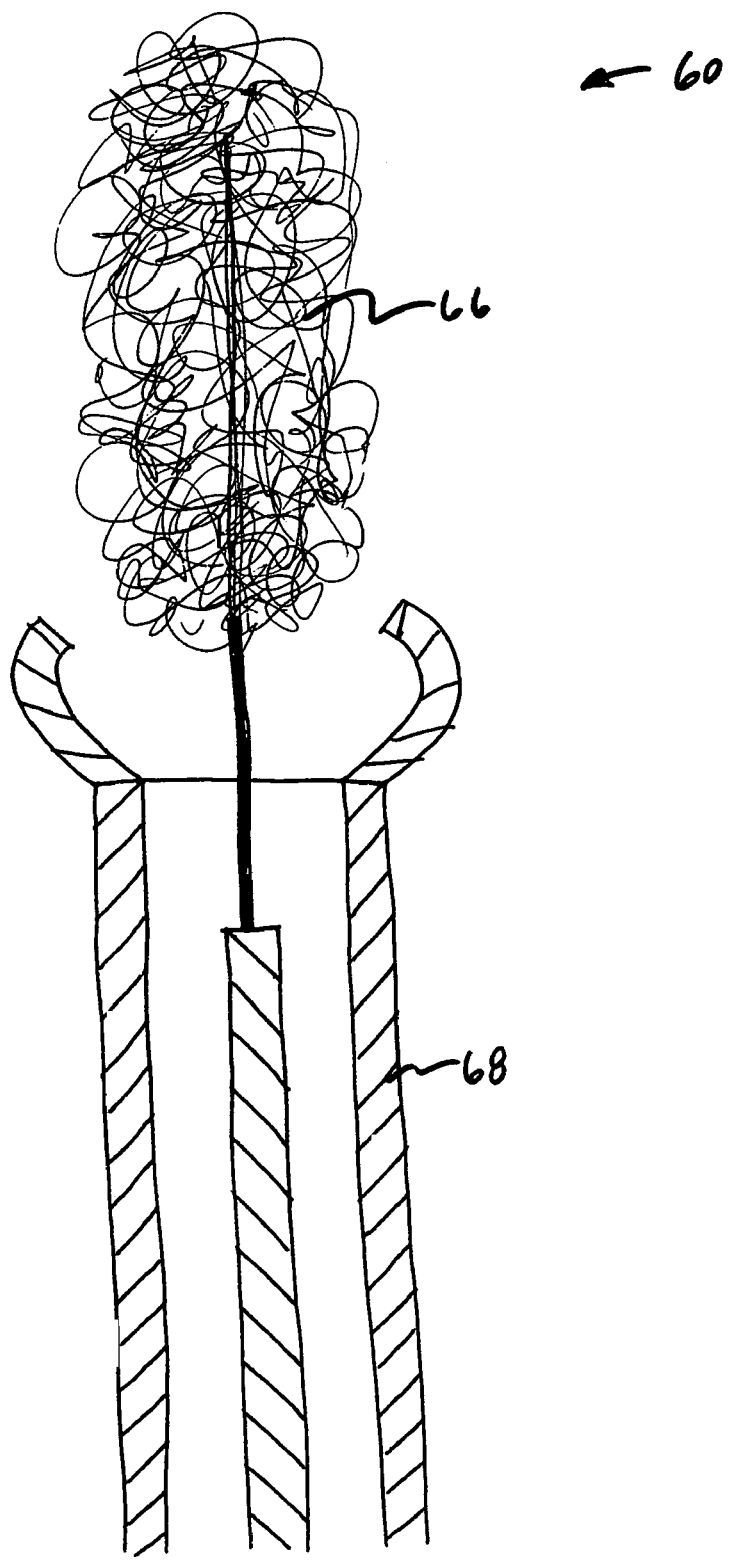

One embodiment of a pretreatment device 60 in accordance with the present invention is shown in FIGS. 12A and 12B. The pretreatment device 60 is configured similar to that of a bottle-brush and can also function as the implant. In this configuration, the pretreatment device 60 includes a stem section 62 and an adjacent trauma-inducing section 64 consisting of bristles or spike-like projections. The stem 62 of the device may be made of rigid polymers, ABS, nylon, PVC, metallics, such as stainless steel or aluminum, and any combination of such materials. The bristles 64 can be fabricated from semi-rigid polymers, nylon or polyethylene. Alternatively, the trauma-inducing section 64 can be configured as a Brillo® pad-like structure 66 capable of scouring tissue, as shown in FIG. 12C. The Brillo® portion 66 may be comprised of collagen coated with a sclerosing agent and can self-expand when deployed from the catheter 68.

Prior to delivery, the brush or bristle portion 64 of the device 60 is contained in the distal section 70 of a catheter or other similar type of delivery tool 68. Preferably, the outer surface of the delivery tool 68 is smooth and/or lubricious to allow for easy insertion into the patient. During the delivery and treatment procedure, the delivery tool 68 is inserted transcervically into the patient and the distal section 70 is positioned within the uterus 42. The pretreatment device 60 is maneuvered so that the bristle portion 64 of the device 60 is deployed at the target site. The device 60 is further manipulated, for example, rolled, twisted, pushed and/or pulled, so that the brush portion 64 inflames the endometrium tissue. The brush portion 64 is then disconnected from the pretreatment device 60 and left in the uterus 42 of the patient. The bristles 64 of the device 60 allow in-growth of fibrous tissue and promote adhesion formation. After the implant 40 is deployed, the catheter 68 is removed from the patient.

Figure 12D:
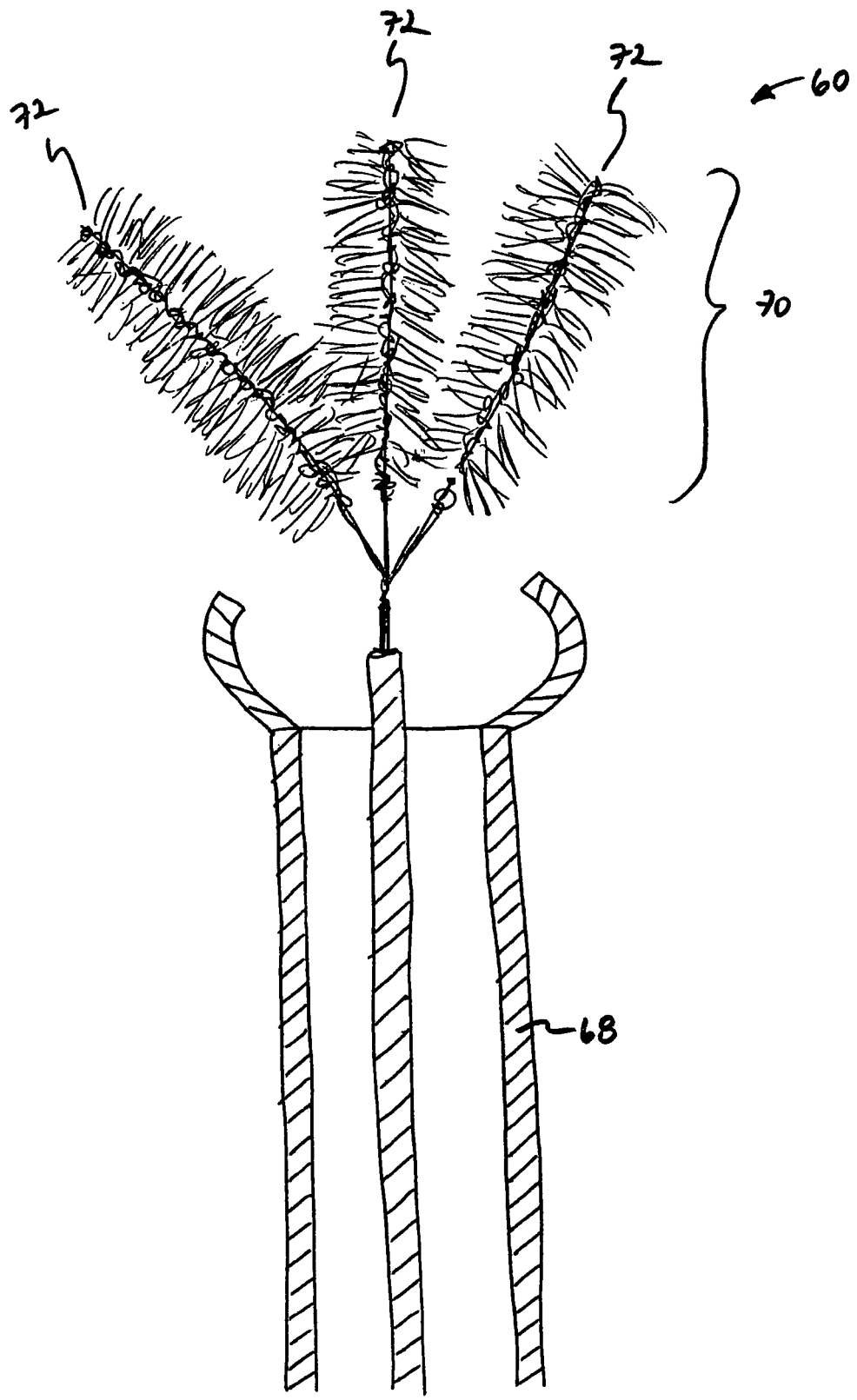

FIG. 12D illustrates an alternate embodiment of the bottle-brush pretreatment device 60. The distal section 70 of the device 60 comprises a multiple-pronged brush 72. This configuration reduces the amount of manipulation required to produce sufficient trauma to the tissue and, also, allows for greater coverage of the endometrium.

Figure 12E:
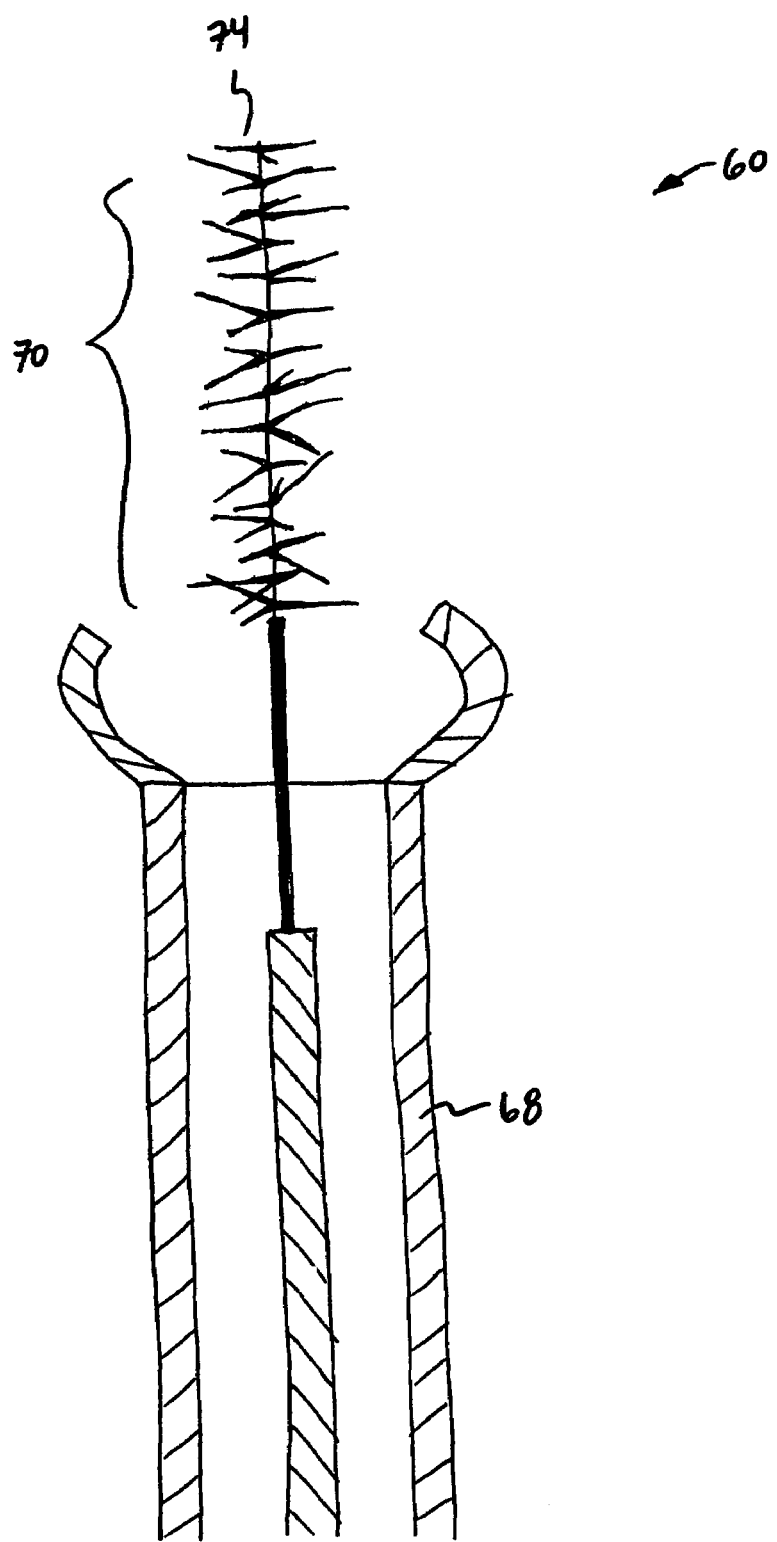

In yet another embodiment of the bottle-brush pretreatment device 60, the distal section 70 of the device 60 includes a wire with sharp protrusions 74, similar to a barbed-wire, as shown in FIG. 12E. As with the bottle-brush configuration, the barbed-wire end 74 of the pretreatment device 60 is rolled, twisted, pushed and/or pulled across the surface of the tissue to cause sufficient insult to the endometrium. Alternatively, an electric current can be applied to the wire 74 as another means of further abrading the endometrial tissue.

Figure 12F:
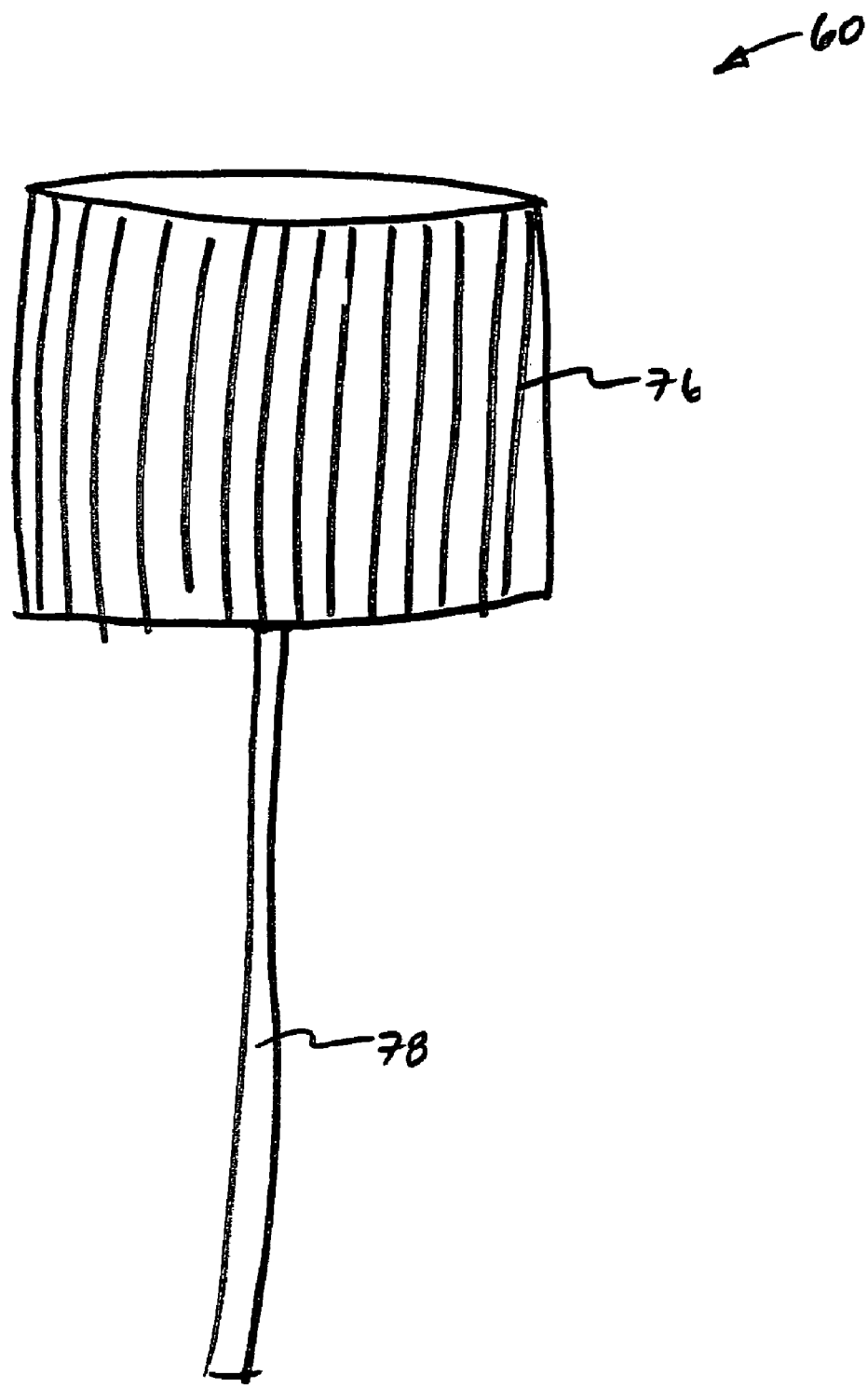

Referring to FIG. 12F, the bottle-brush portion of the pretreatment device 60 can also be designed in a cap or collagen plug 76 configuration. The collagen plug 76 has a naturally abrasive surface and is attached to a stylet 78 for manipulation and deployment. The stylet 78 is rotated, pushed or pulled to create sufficient trauma to the endometrium. Alternatively, a crystalline material could be embedded in the collagen of the plug 76 to create greater surface roughness. After the pretreatment procedure is complete, the plug 76 is unscrewed from stylet 78 and remains in the uterus 42 to promote adhesion formation.

Figure 13A:
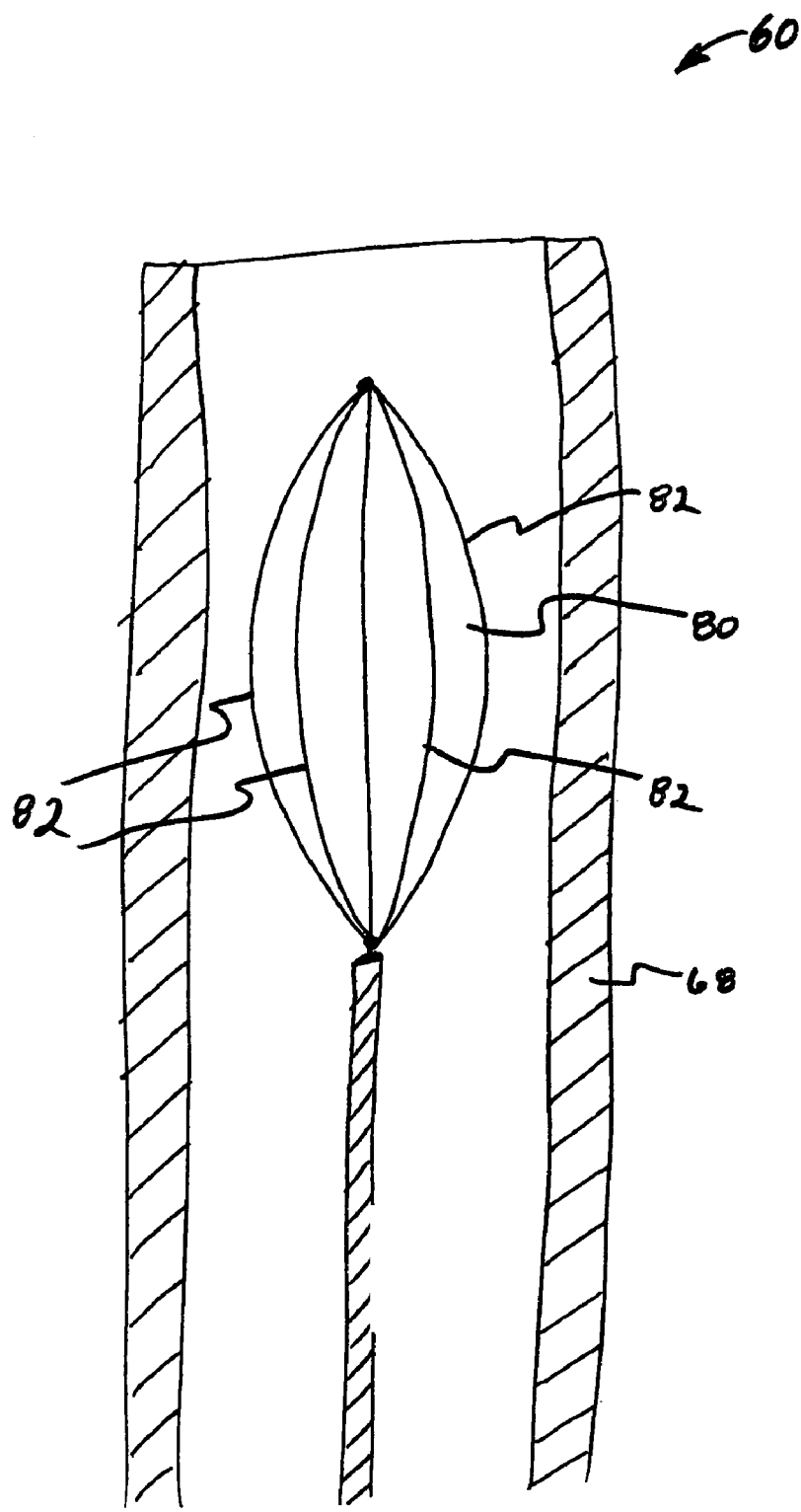
FIGS. 13A-13C illustrate alternate embodiments of a pretreatment device in accordance with the present invention.
Figure 13B:
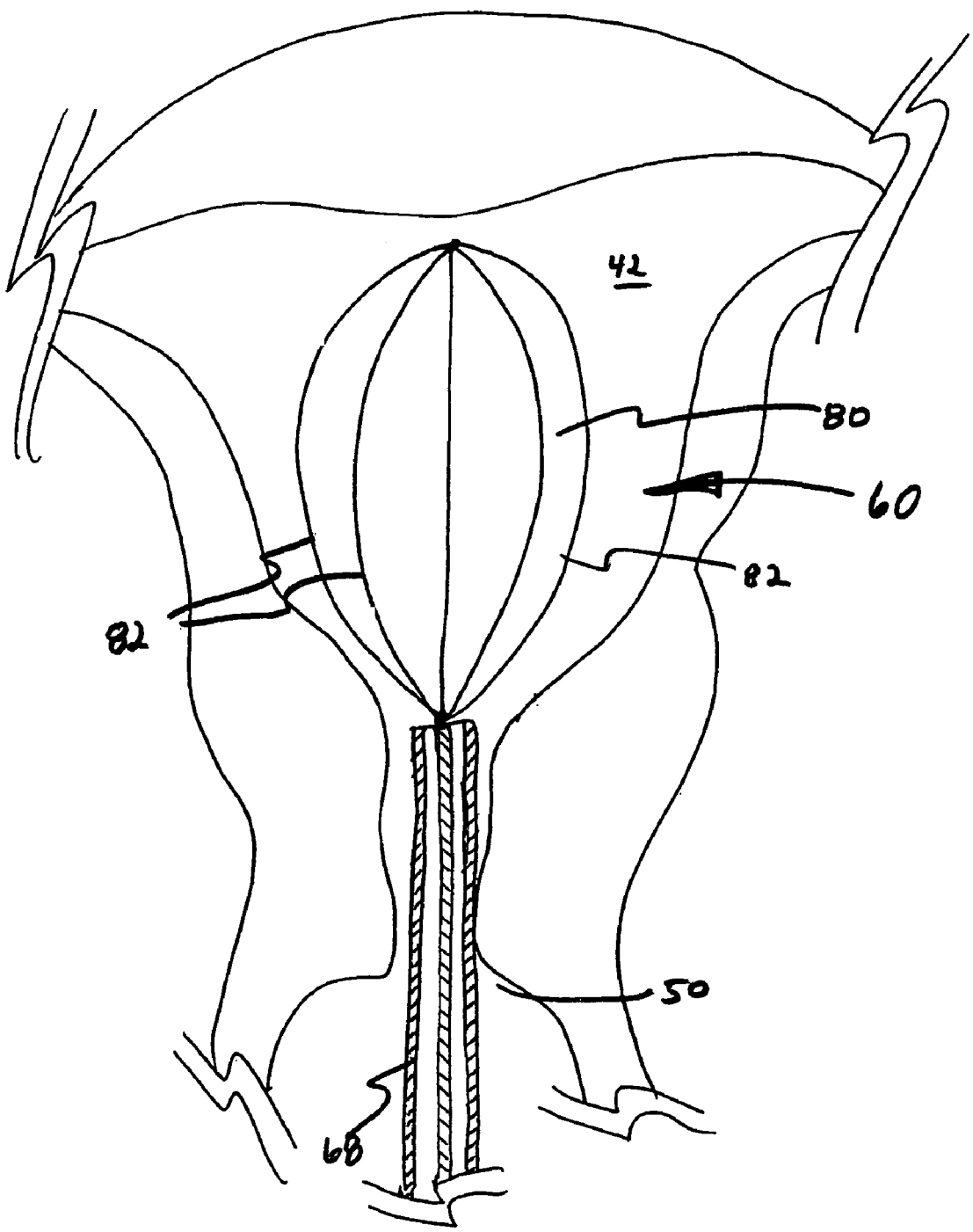
Figure 13C:
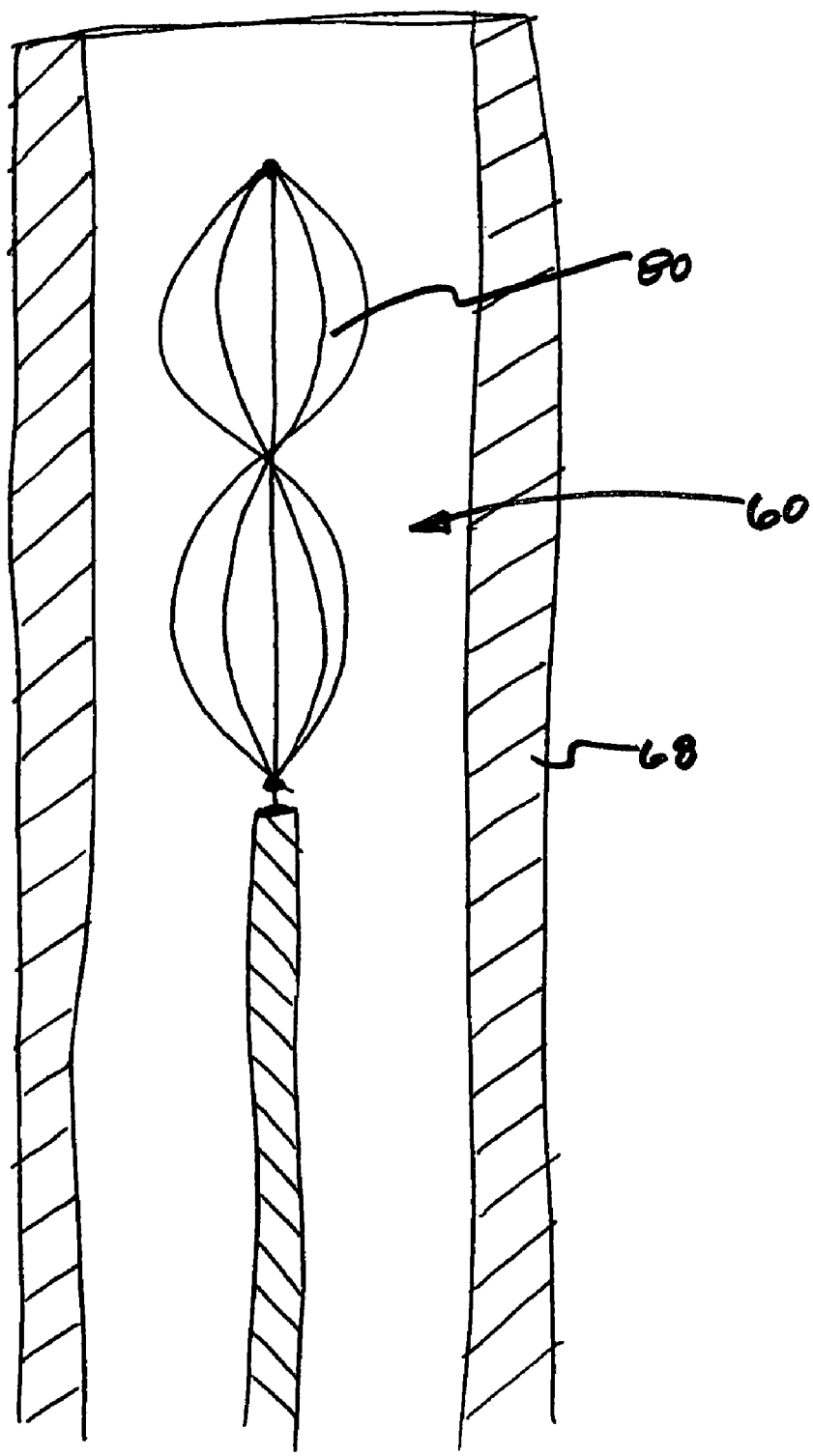

Referring to FIGS. 13A and 13B, an alternate embodiment of the pretreatment device 60 comprises a wire-formed distal end 80. The distal section of the device 60 is comprised of one or more wires 82 that are configured to form an egg-beater or whisk-like design. Nitinol®, stainless steel, titanium and other similar materials, including combinations of such materials, may be used to fabricate the wires 82 of the device 60. Prior to insertion through the cervix 50 and into the uterus 42 of the patient, the wires 82 are retracted into the cannula 68 of the delivery tool. The wires 82 may fold together, similar to closing an umbrella, or twist toward the center axis of the device 60, as shown in FIG. 13C, in order to fit within the cannula 68. After the device 60 is positioned within the uterus 42, the wire-formed distal end 80 is deployed causing the wire form to radially expand from the center axis of the device 60. The device 60 is then manipulated in a curettage-like action to scrape or insult the endometrium. After the pretreatment procedure is complete, the wire-formed distal end 80 is retracted and the device 60 is removed from the patient.

Figure 14A:
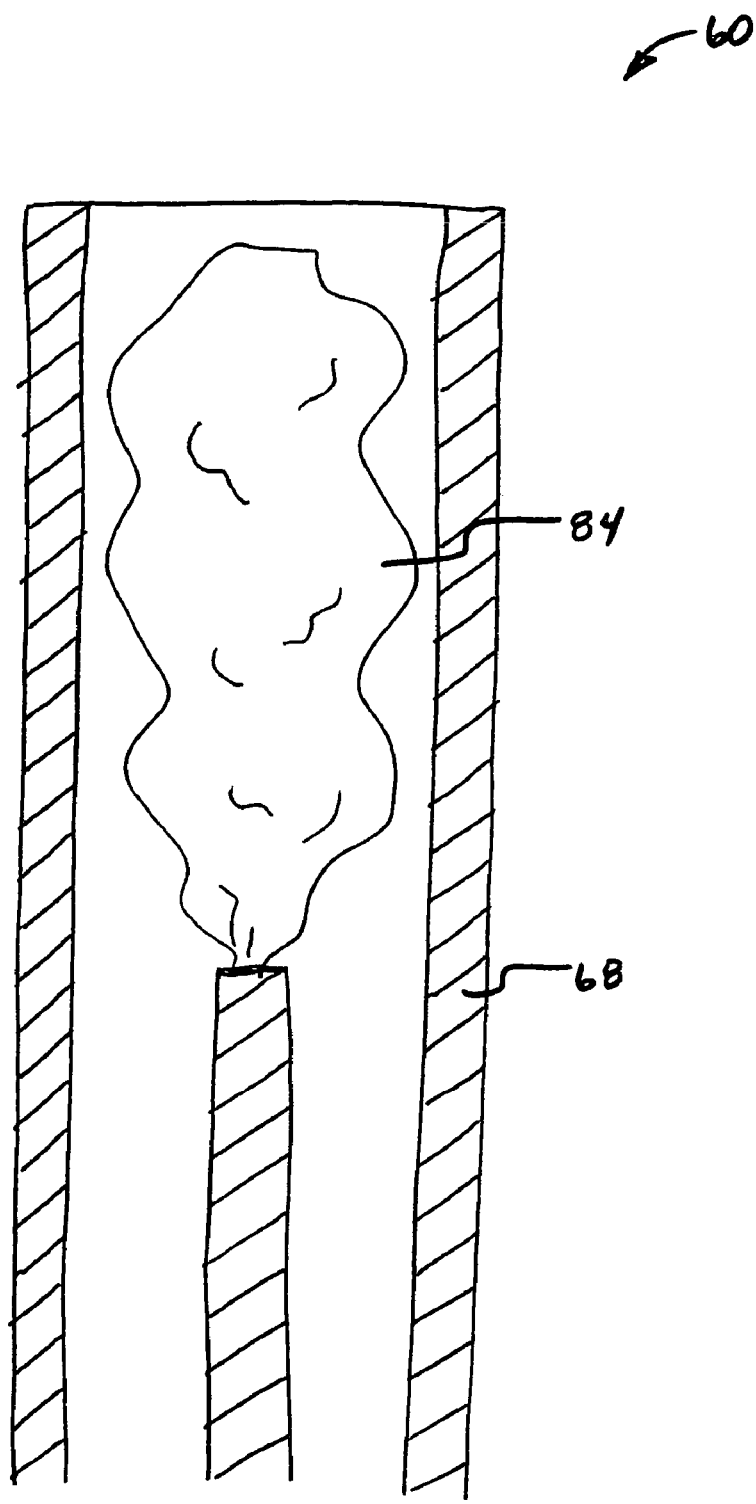
FIGS. 14A-14C illustrate various views of another embodiment of a pretreatment device in accordance with the present invention.
Figure 14B:
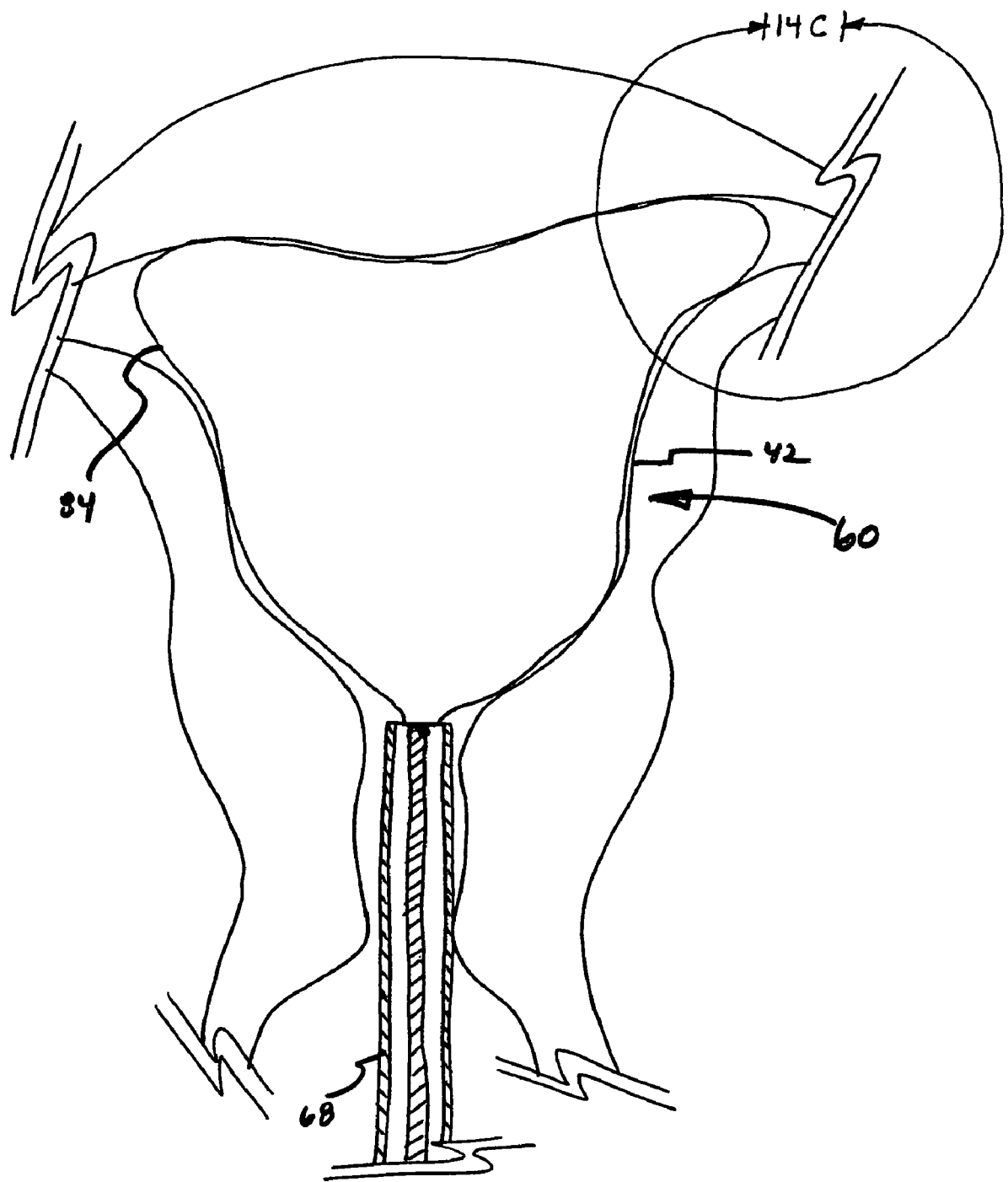
Figure 14C:
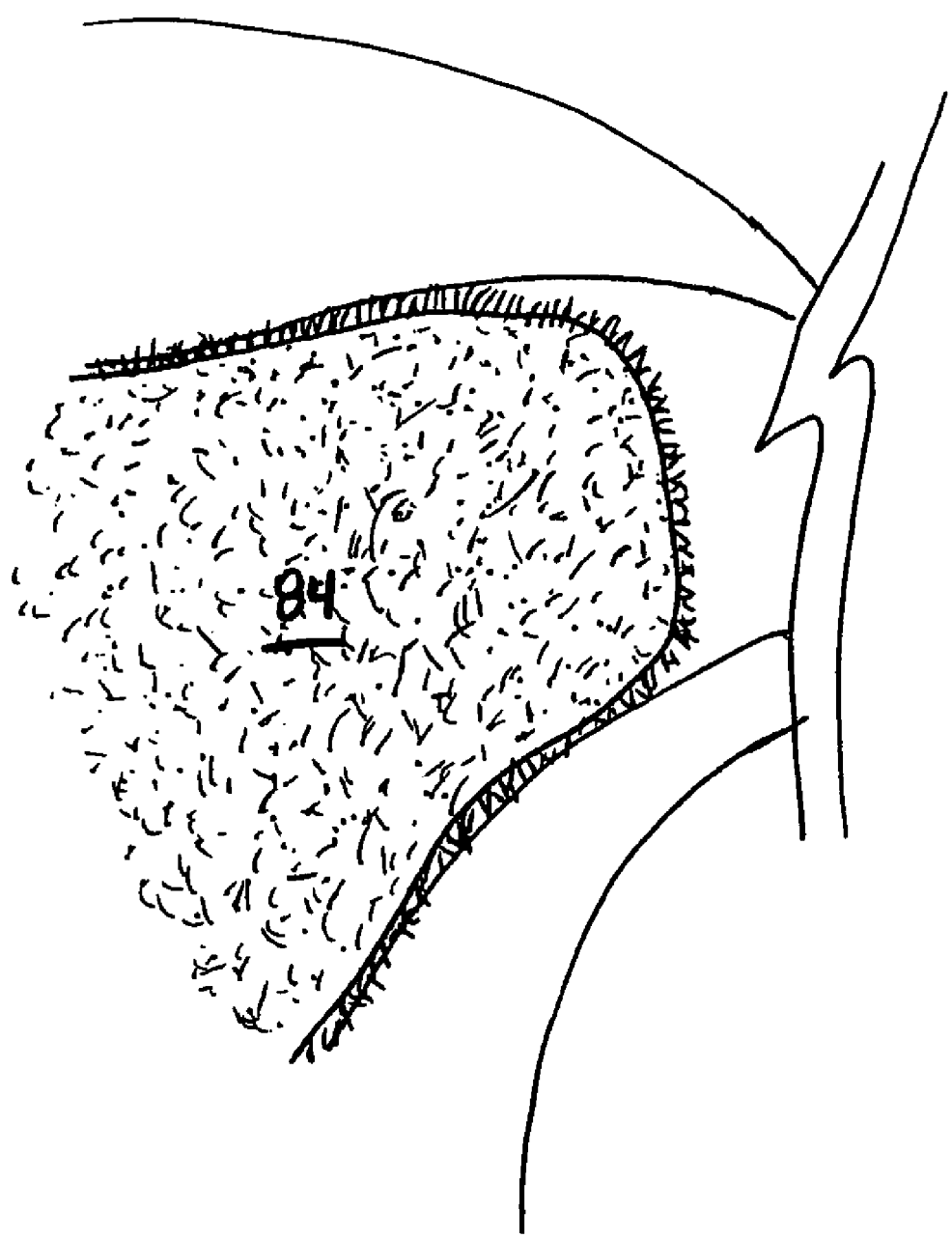

In another embodiment of the invention, a balloon 84 having a rough external surface is used to induce trauma to the endometrium. As shown in FIGS. 14A and 14B, the balloon 84 is deflated and housed within the lumen of a cannula 68 prior to deployment. After the distal portion of the pretreatment device 60 is accurately positioned within the uterus 42, the balloon 84 is deployed or radially inflated to fill the uterine cavity. The external surface of the balloon 84, shown in FIG. 14C, may include various fine wires, blades, small bristles or other abrasive textures capable of abrading tissue. The device 60 is then manipulated, for example, rotated, pushed and/or pulled, or repeatedly inflated and deflated, so that the abrasive surface of the balloon 84 inflames the endometrium. The balloon 84 is deflated and retracted into the cannula 68 and the device 60 is removed from the uterus 42 of the patient after the pretreatment procedure is completed.

Figure 15:
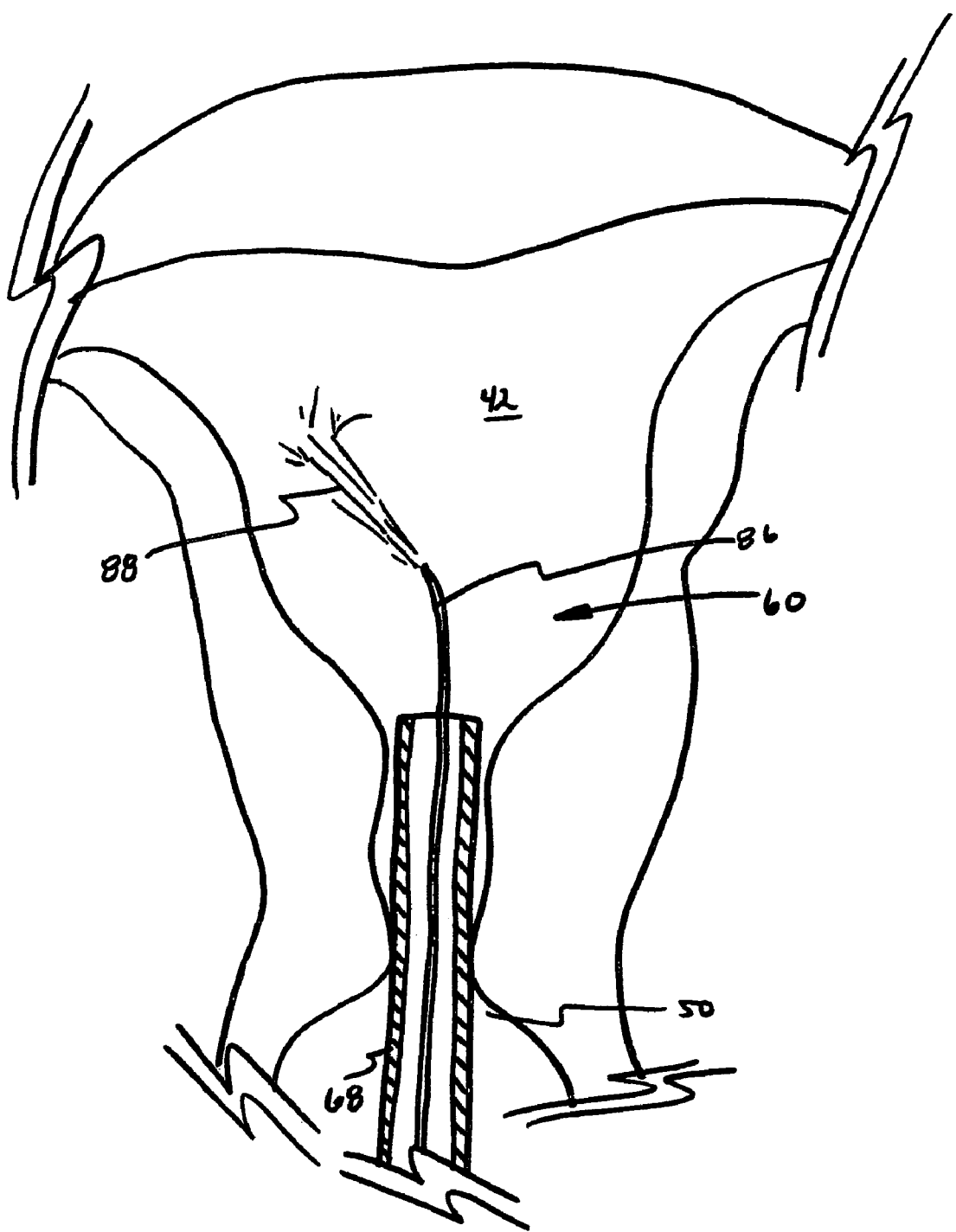
FIG. 15 illustrates a sectional view of another embodiment of a pretreatment device in accordance with the present invention.

Referring to FIG. 15, the pretreatment device 60 of this embodiment of the invention utilizes a type of "sandblasting" or liquid abrasion technique to create trauma to or insult the endometrium. A flexible tube 86 having a curved, steerable tip housed within a catheter 68 is used to deliver the pretreatment fluid 88 and, thereby, insult the tissue. In one embodiment, the fluid 88 comprises a crystalline salt that is suspended in or pulled into the water stream: Prior to delivery, the uterus 42 of the patient may be distended utilizing a gas, such as carbon dioxide ($CO_2$), or a mechanical spreader to fully expose the entire surface area of the endometrium. The pretreatment device 60 is then inserted through the cervix 50 and into the uterus 42 of the patient. After the device 60 is properly located in the uterus 42, the steerable tip is maneuvered within the uterus 42 so that the fluid suspension 88 impinges on the endometrium and blasts away the tissue. The pretreatment device 60 is removed from the patient after the procedure is completed. Although a flexible tube having a curved, steerable tip housed within a catheter is one embodiment, other tube and/or catheter configurations and steering/guiding means, though not specifically described herein, are also included within the scope of the claimed invention.

Indirect pretreatment involves the use of drugs or the patient's own biological timing cycle. In one embodiment, a hormonal drug therapy is used to help reduce the thickness of the endometrium and down regulate the patient prior to the procedure. Drugs such as depolupron (luprolide acetate) may be used to stimulate such a response when given in dosages of 3.75 gm/month. This drug therapy may be initiated up to sixty (60) days prior to receiving the device 40. In addition, this treatment may continue for a period post-implant to ensure complete acceptance of the device 40 at the target site. Alternatively, other hormone-altering medications (such as progesterone, estrogen), antibiotics, drugs or other indirect pretreatment preparations may also be used prior to implantation of the device 40 within the patient's uterus 42.

In an alternate embodiment, indirect pretreatment involves timing the device implantation procedure to the patient's normal menstrual cycle. For example, for some patient's, optimal timing is defined as the point in time when the patient's endometrium is in a specific state or condition. Generally, the endometrium is at its thinnest at the beginning and end of the menstrual cycle. In particular, the fourth or fifth day after the initiation of bleeding is known to be when the endometrium is at its thinnest and beginning to reform (i.e. also known as the proliferative stage). As such, the endometrium is most vulnerable to insult and should be in an optimal state for adhesion formation. Therefore, it would be most advantageous to perform the procedure using the intrauterine device 40 of the present invention during these time periods. In addition, timing could also be used in conjunction with drug therapy to further optimize the endometrial lining.

Another embodiment of a pretreatment method uses drugs, hormones or other chemicals either alone or in conjunction with the mechanical pretreatment devices 40 previously disclosed. For example, the mechanical devices 40 may be coated with the chemicals configured in a dry format. The chemicals are hydrolyzed and, thereby, activated when they come in contact with the patient's body fluids and/or tissues. Alternatively, the chemical(s) may be dispensed in a liquid format at the treatment site and allowed to act upon the tissue for a specified time period. At the end of the time period, the implant may be deployed or, as an alternative, the reaction is stopped prior to the implant being deployed.

Examples of appropriate chemicals include weak acids, weak bases, saline (with a high concentration of salt to create an osmotic effect), silver nitrate, quinine solution, sodium morrhuate, sodium tetrade, alcohols, alcohols with formalin (i.e. formaldehyde) and other similar sclerosing/necrosing agents or chemicals that cause insult to the endometrium. This pretreatment procedure may also require post-procedure neutralization of the chemicals followed by a lavage of the uterine cavity to allow proper adhesion formation.

Post-Treatment

After the device 40 is implanted at the target site in the patient's uterus 42, the patient may be placed on antibiotics to treat possible infections that may occur within the uterus 42. Although it may not be desirable to eliminate a low grade infection since this may be one of the factors that allows for the successful creation of uterine adhesions, long-term unresolved infections are undesirable and should be treated. Alternatively, additional hormone therapy, drugs or chemicals may also be given to the patient as post-treatment (to down regulate the patient) or for a prescribed period of time after the procedure.

Method of Device Deployment

The preferred method for deployment of the device 40 of the present invention is trans-vaginally and trans-cervically, without the need for surgical intervention, and, therefore, can be performed aseptically. In general, a catheter, cannula or similar device 68 is inserted through the cervix 50 and into the uterus 42 of the patient. A fluid, gas or mechanical means may be used to distend the uterus 42, thereby facilitating delivery of the device 40. The device or implant 40 is then deployed through the catheter 68 with or without the use of additional tools, out the distal end of the catheter 68, and into the uterine cavity 44. After device delivery, the catheter 68 is removed from the patient and the uterus 42 is subsequently allowed to contract or collapse to its natural state, whereby all of the uterine walls are brought into contact with the device 40. In most cases, the procedure is performed without the use of a hysteroscope or other imaging device. Thus, the procedure is performed without direct visualization of the uterine cavity. However, if necessary, imaging techniques such as ultrasound and fluoroscopy may be used. In general, the procedure of the present invention allows the patient to be treated in an out-patient setting and requires minimal pain management and time.

In an alternate embodiment, an additional apparatus or tool is used with the implant 40 of the present invention. The additional apparatus is a hollow tube or guide that forms a pathway to the cervix 50. The guide is implanted, either permanently or temporarily, within the patient. Alternatively, the apparatus may also be a lumen, channel or other similarly configured component. The pathway formed by the apparatus not only enables easy insertion of the device 40 but also allows for drainage of the uterine cavity 44. In addition, the pathway may also be used for post-procedure therapy or future diagnosis of the uterine cavity 44. For example, if required, a biopsy of the uterine tissue may be performed using the channel as an access port.

Figure 16A:
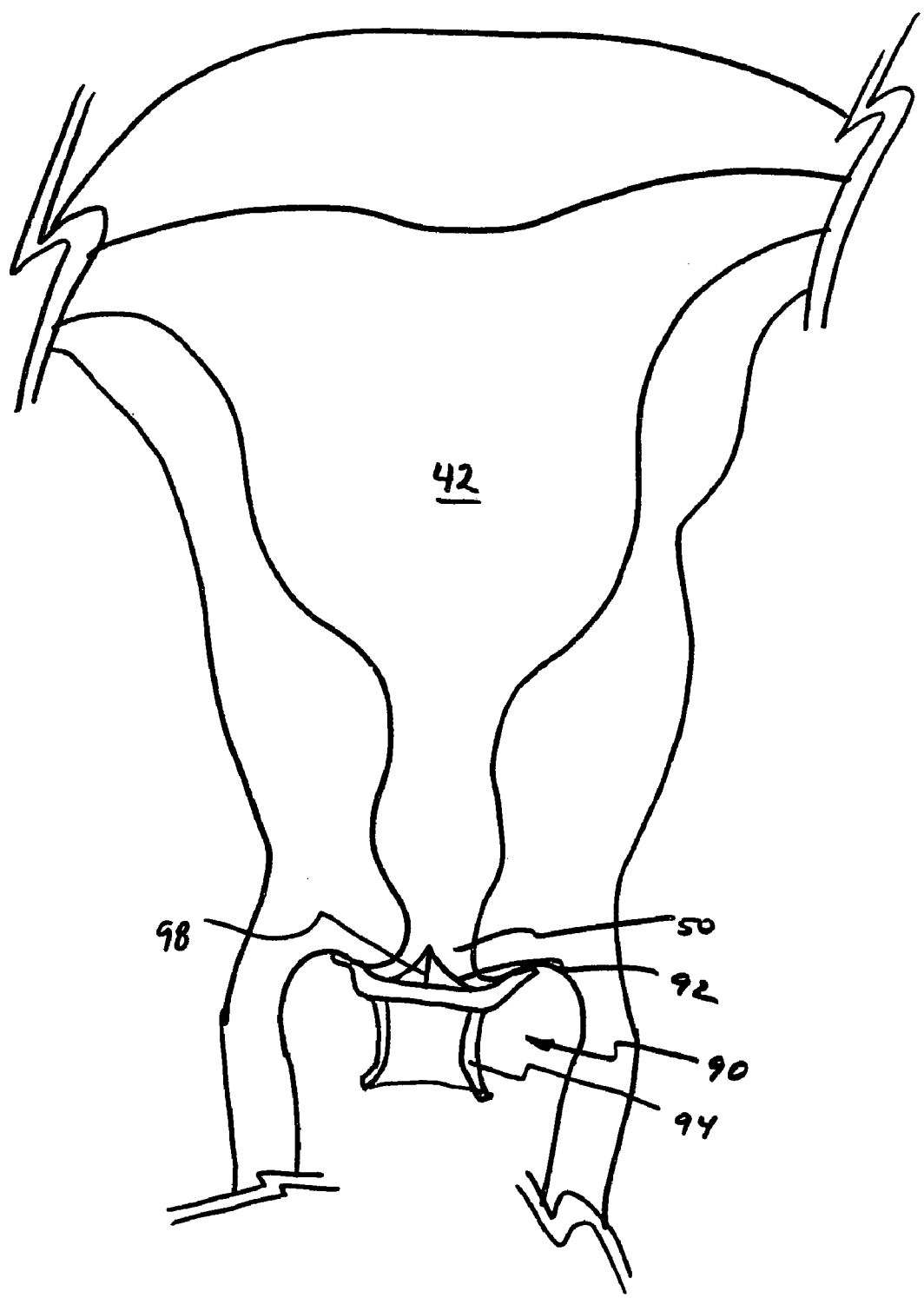
FIGS. 16A-16D illustrate various views of a cervical cap used with a delivery tool in accordance with an embodiment of the present invention.
Figure 16B:
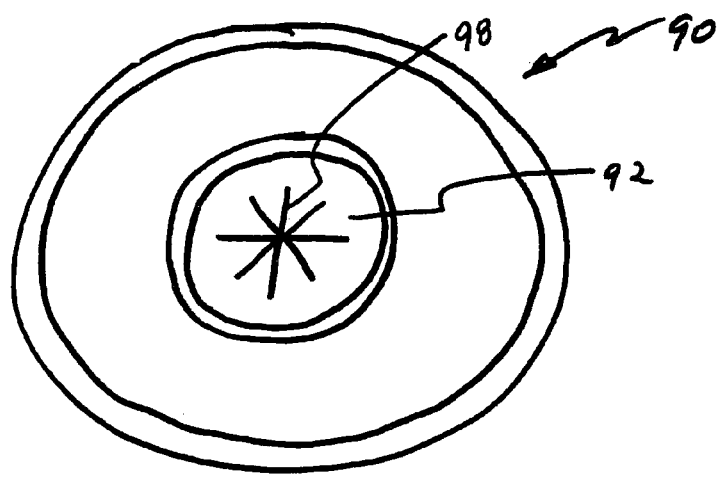
Figure 16C:
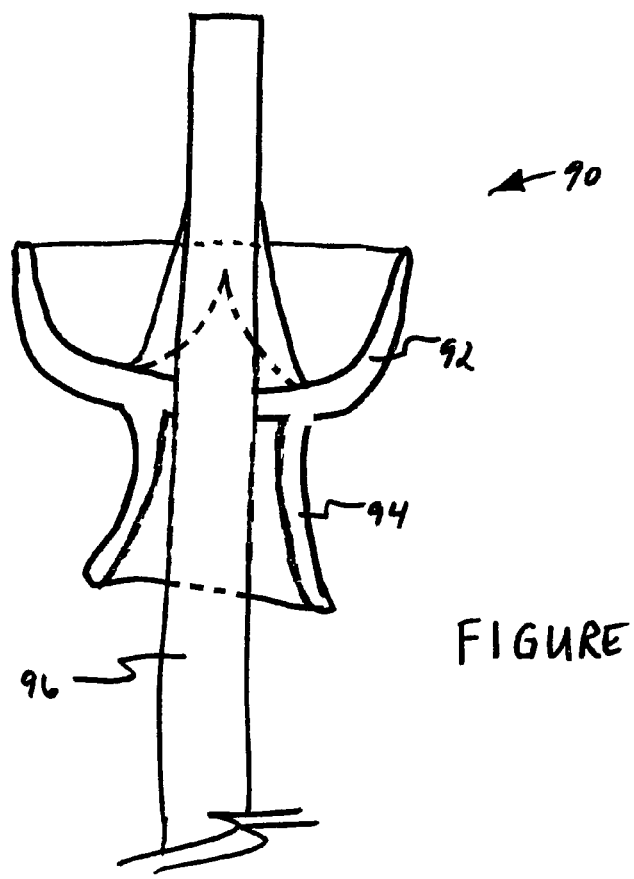

Alternatively, a cervical cap can also be used in conjunction with a deployment or delivery tool. As shown in FIGS. 16A and 16B, the cervical cap 90 comprises a one-way valve device 92 that is deployed on the cervix 50 of the patient. In addition to the one-way valve 92, the cap 90 also includes a hollow tube or guide 94 located on the proximal end of the cap. In the embodiment shown in FIG. 16A, the guide 94 allows access for a tool, such as a catheter 96. Initially, the cap 90 is installed on the catheter/delivery tool 96. One or more slits 98 located on the valve or duck-bill portion of the cap 90 open to allow passage of the catheter 96 therethrough, as shown in FIG. 16C. When the catheter 96 is inserted through the cervix 50 and into the uterus 42 of the patient, the cap 90 is deployed onto the cervix 50. After the implant 40 is delivered and the catheter 96 removed from the uterus 42, the cap 90 remains attached to the cervix 50.

Figure 16D:
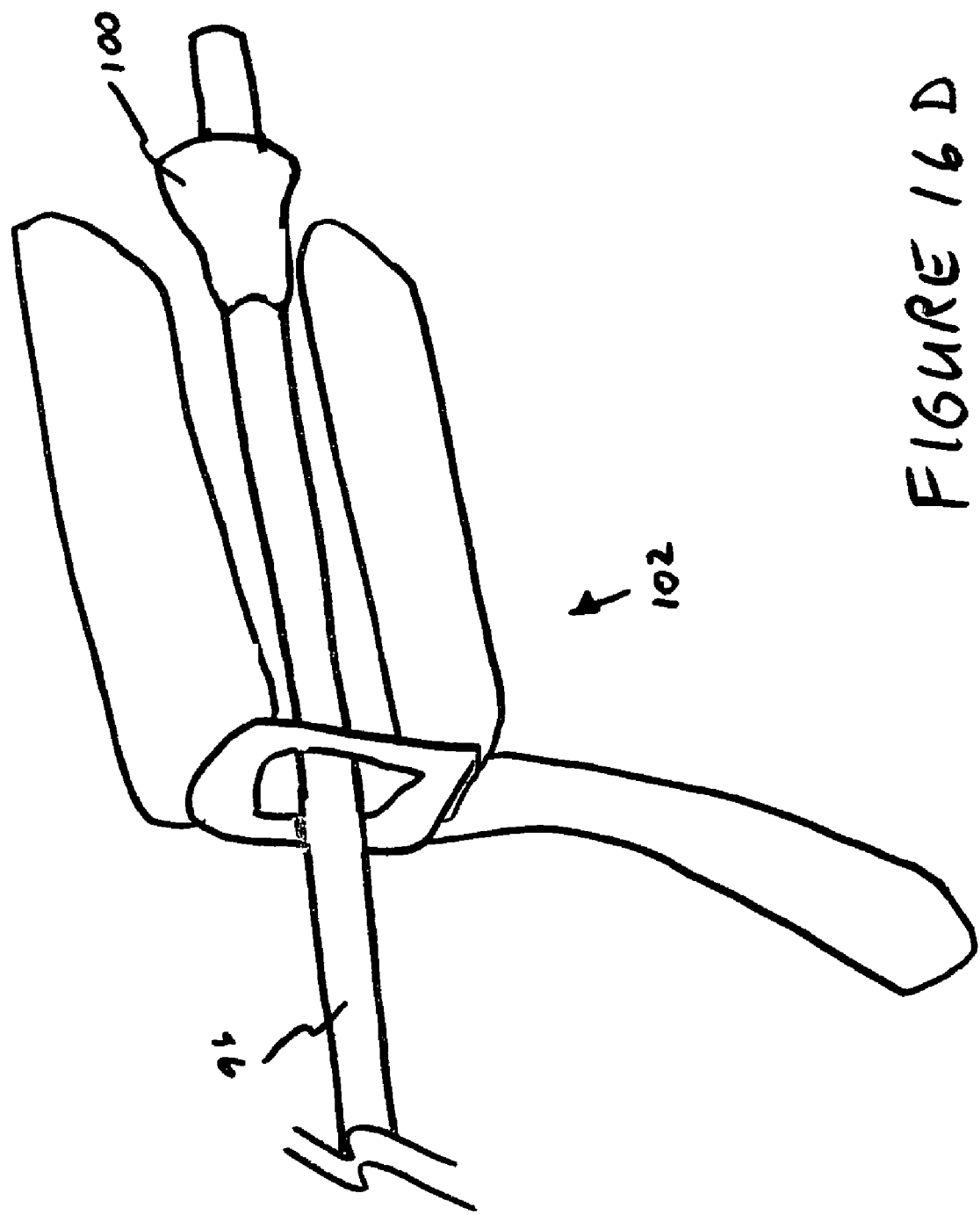

In an alternate embodiment, the cervical cap forms a cup-shaped device 100 attached to a hollow tube or catheter body 96. Referring to FIG. 16D, the cup 100 attaches to the cervix 50 of the patient (not shown) and includes one or more lumen/ports for dispensing fluid, creating vacuum, delivering tools (such as a curret wire) and deploying the implant. In addition, the deployment tool may also be configured to include a speculum 102 to dilate the vagina and allow free movement there-through of the catheter portion of the tool.

Figure 17:
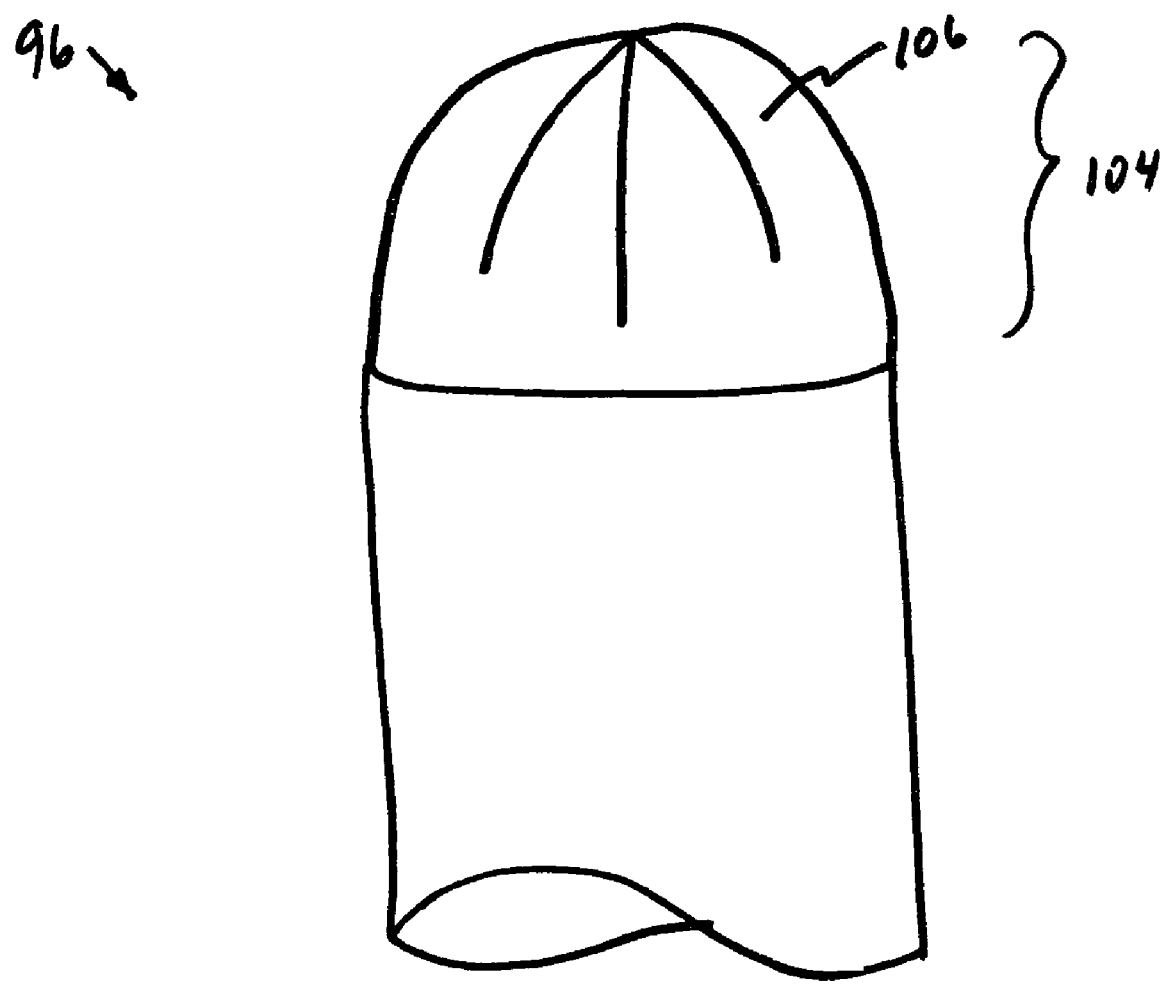
FIG. 17 illustrates a perspective view of the distal end of a catheter in accordance with an embodiment of the present invention.

In another embodiment of the present invention, device deployment is conducted via a cannula or catheter 96 inserted through the vaginal opening and the cervix 50. The cannula provides a means of access to the inside of the uterus 42. As shown in FIG. 17, the distal end 104 of the cannula or catheter 96 comprises an atraumatic, blunt tip 106. The tip 106 is made of a low durometer material, such as silicone, low durometer PVC, polyurethane, thermoplastic elastomers (TPEs) or other materials comprising a shore hardness of less than 50 durometers. In order to withstand insertion forces, the body of the catheter 96 is made of higher durometer materials, such as Polyvinyl Chloride (PVC), Polypropylene, urethane, polyethylene or other similar materials. Using this access means, the physician can then dispense the material or deploy the device 40 using either direct mechanical motion (stylet movement) or pressure/force created in a device external to the patient (for example, a syringe or spray-can type device).

Numerous methods for dispensing various types of implants 40 may be used in conjunction with the cannula or catheter 96. For example, in one embodiment, the intrauterine device 40 is comprised of a mesh sheet that is cut to a predetermined size. Basing the dimensions on a large population sample can be used to optimize dimensions of the implant size. Alternatively, the mesh sheet can be custom sized to the patient's uterus 42 by pre-imaging the uterus to determine its shape and then using that image to cut the mesh into the appropriate configuration. The mesh sheet is loaded into the cannula 96 and the cannula 96 is manipulated through the cervix 50 and into the uterus 42. A stylet, wire or other type of tool is used to push the mesh out of the cannula 96 and into the uterine cavity. The mesh unfolds, due to either physician manipulation or the material characteristics of the mesh, and covers the posterior surface of the uterine cavity.

Several embodiments of various deployment tools are shown in the following Figures. In general, the deployment tools include one or more expanding elements attached to the implant. The expanding elements may be absorbable, resorbable or non-absorbable. In the non-absorbable configuration, the expanding elements are detached from the implant after deployment and removed from the patient. The expanding elements are generally attached to the implant in such a way as to cause the implant to unfold, spread and/or expand within the body cavity. In addition, one or more manipulator elements can also be used to motivate, urge or manipulate the expanding elements into a configuration that stretches and expands the implant within the body cavity. The manipulator elements may also be absorbable, resorbable or non-absorbable.

Figure 18B:
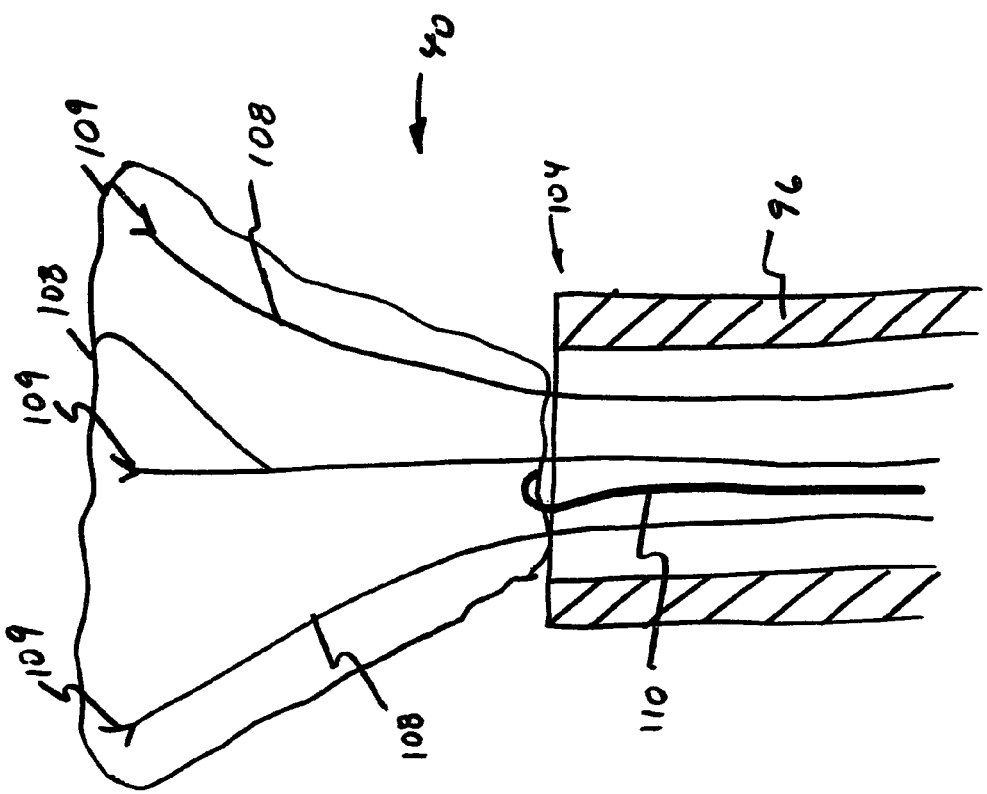
FIGS. 18A-18B illustrate an embodiment of the deployment tool in accordance with the present invention.
Figure 18A:
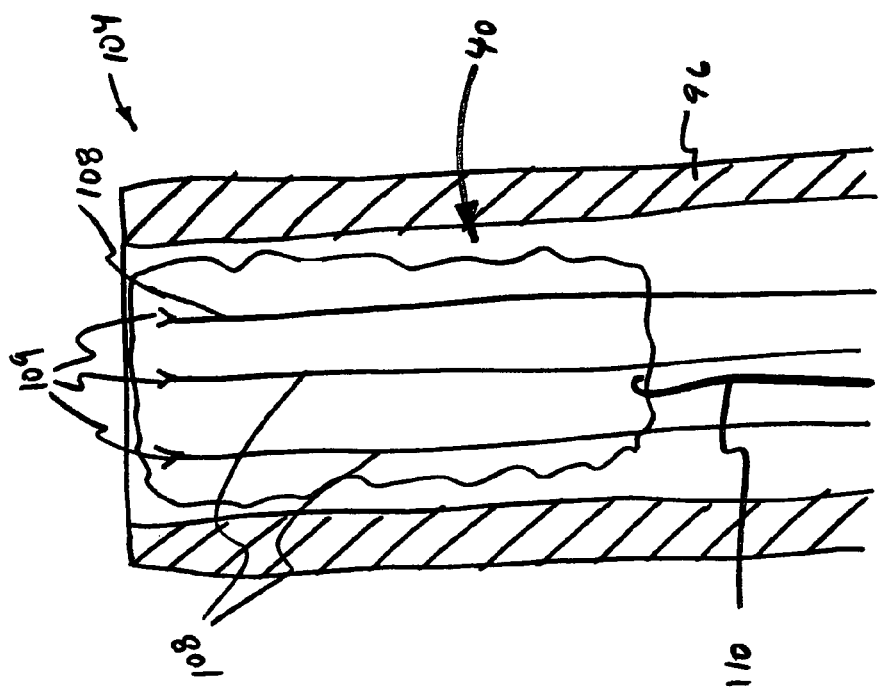

Referring to FIGS. 18A and 18B, one embodiment of the deployment tool comprises a wire hook 110 and one or more wires 108 that are attached to the implant 40 via a one-way barb 109. During deployment of the device 40, the barbed-wires 108 are advanced through the distal end 104 of the catheter 96 and into the uterus 42 of the patient. The wire-hook 110 is then retracted causing the implant 40 to expand and spread into the uterine cavity. In general, the barbed-wires 108 are designed and fabricated to expand into a fan-shape when extended from the catheter lumen. However, the particular location of attachment of the barbed-wires 108 to the mesh material also promotes further stretching or expansion of the implant 40 in both vertical and horizontal directions. After the implant 40 is properly positioned in the uterus 42, the wire-hook 110 is advanced and used to release the barbed-wires 108 from the implant 40 and retract the wires 108 back into the lumen of the catheter 96 for subsequent removal from the patient.

Figure 19A:
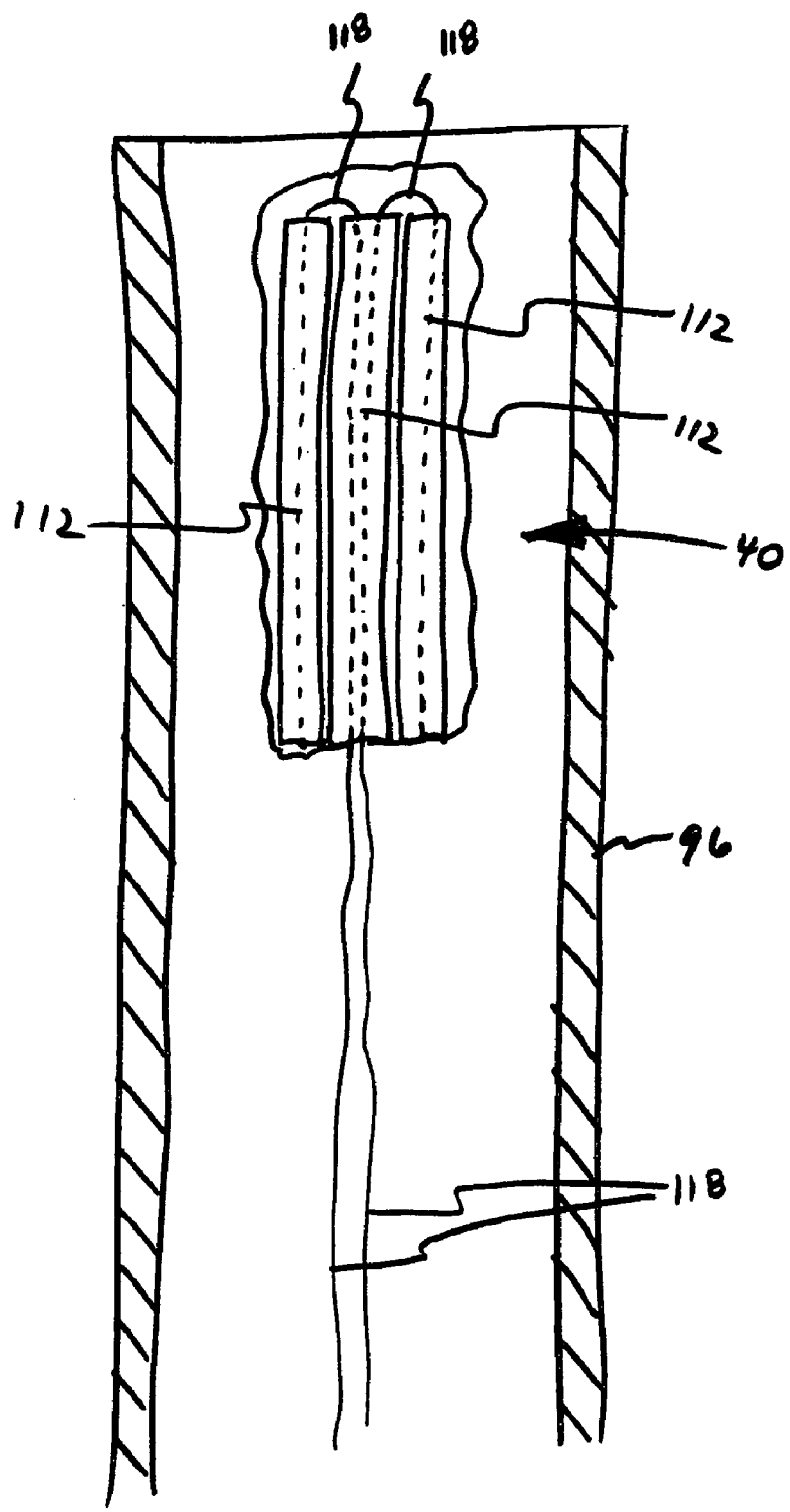
FIGS. 19A-19B illustrate another embodiment of the deployment tool in accordance with the present invention.
Figure 19B:
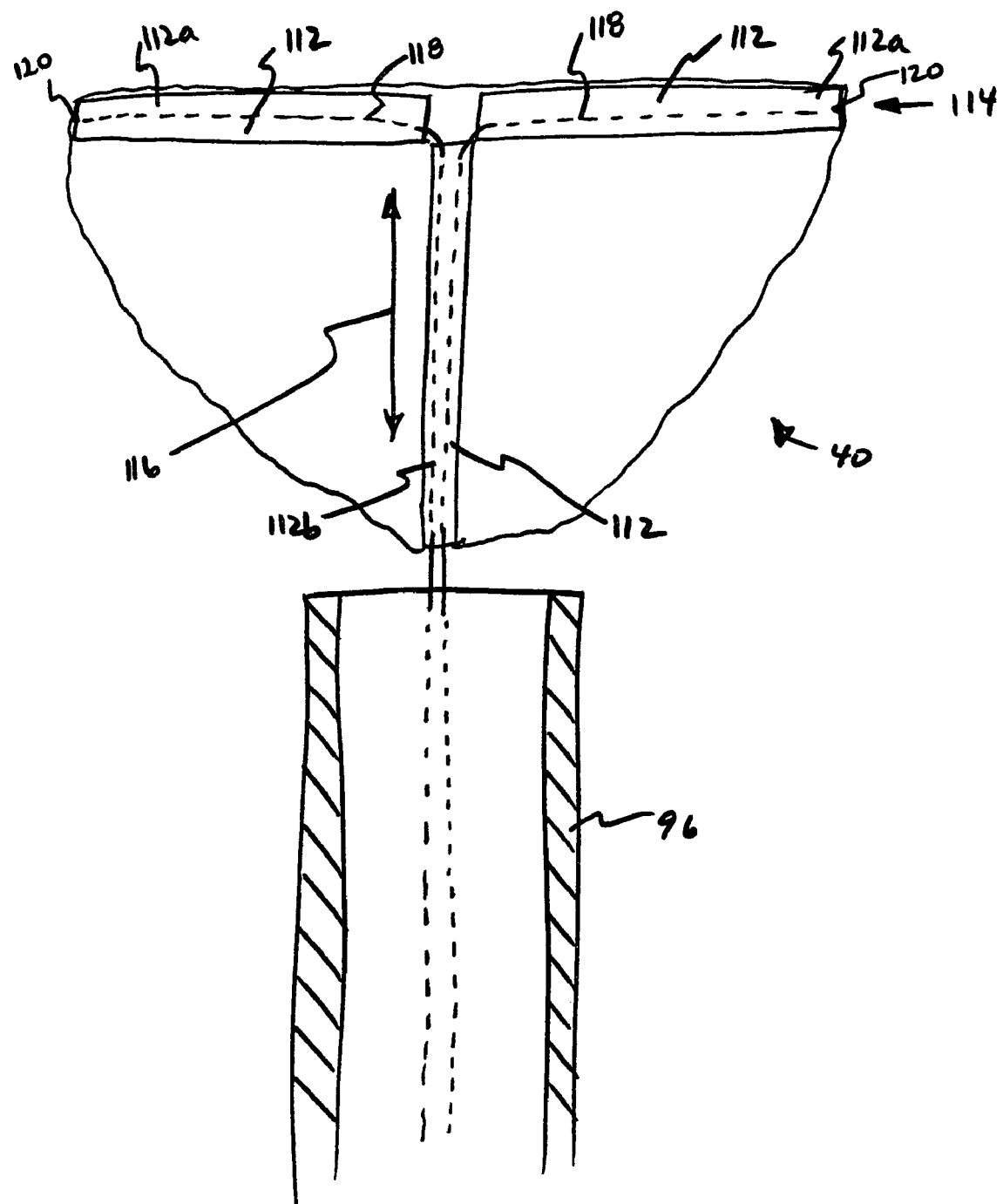

Another embodiment of a deployment tool is shown in FIGS. 19A and 19B. The deployment tool and delivery method of this embodiment are similar to that of an intrauterine device (IUD). The deployment tool comprises a catheter 96 and three rigid lumens or arms 112 that are attached to the implant 40. For an implant 40 configured similar to an inverted triangle, two of the lumens or arms 112a are attached to equal halves of the base 114 of the triangularly-shaped implant 40 and the third lumen 112b is attached to and runs along the height 116 of the triangularly-shaped implant 40. A string or monofilament 118 is housed within the lumen and attached to the outer end 120 of each of the arms 112a. The strings 118 are threaded through the lumen that runs along the height 116 of the implant 40 and into the catheter 96 for manipulation by the physician. Prior to delivery, the arms 112a are retracted adjacent to the third lumen 112b. After the tool is inserted through the cervix 50 and into the uterus 42, the three rigid lumens 112 are positioned within the uterine cavity using a stylet or similar device. The strings 118 are pulled by the physician in a proximal direction, thereby causing the arms 112a to deploy the implant 40. After the device 40 is implanted in the uterus 42, the catheter 96 is removed from the patient. The biocompatible lumens 112 and strings 118 remain in the uterus 42 and/or are absorbed by the tissues.

In an alternate embodiment (not shown), a hinge located at the junction of the three lumens 112 replaces the function of the monofilament 118. In this configuration, the hinge, in a spring-like fashion, automatically deploys the arms 112a of the tool as soon as they are released from the catheter 96 into the uterus 42 of the patient. This configuration and method is also similar to the IUD design and method of deployment.

Figure 20B:
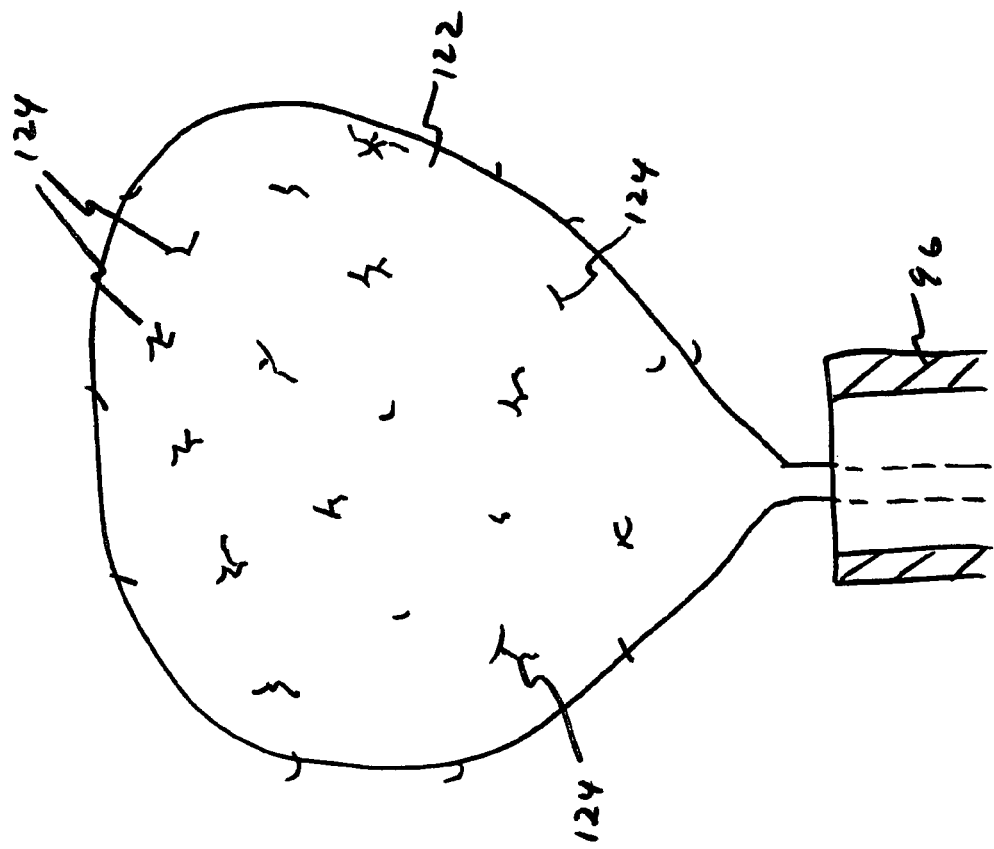
FIGS. 20A-20B illustrate yet another embodiment of the deployment tool in accordance with the present invention.
Figure 20A:
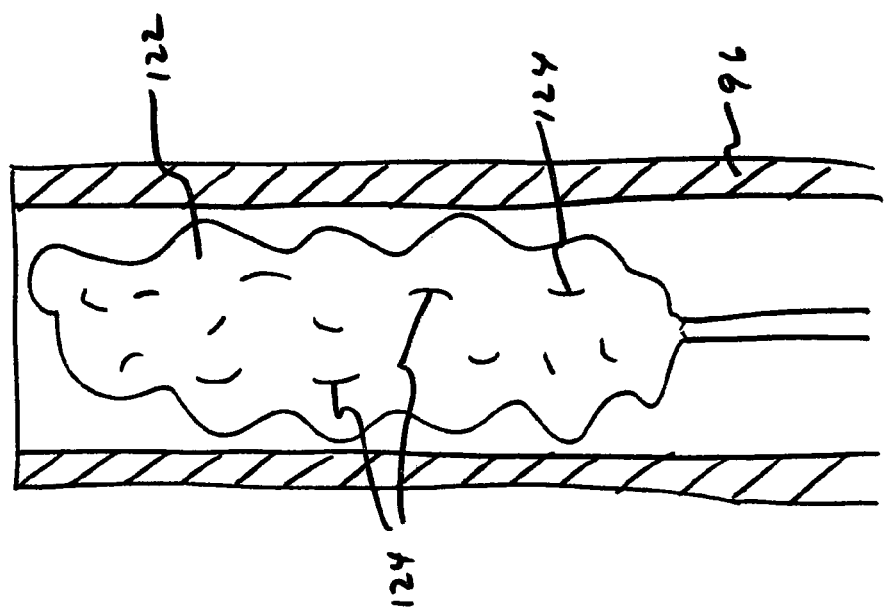

Referring to FIGS. 20A and 20B, the deployment tool comprises an elastic membrane 122, such as a balloon, coated with mesh, mesh particulate or other adhesion creating substance 124. The substance 124 forms a brittle coating on the external surface of the membrane 122. During deployment, the catheter 96 is placed in the uterus 42 of the patient and the balloon 122 is advanced and inflated via an inflation lumen. The expanded membrane 122 causes the particulate 124 to break off the surface of the balloon 122 and coat the endometrium. The balloon 122 is then deflated and removed from the uterus 42 of the patient. Alternatively, the balloon 122 can be made of a biocompatible material and, therefore, can remain within the uterine cavity.

Figure 21B:
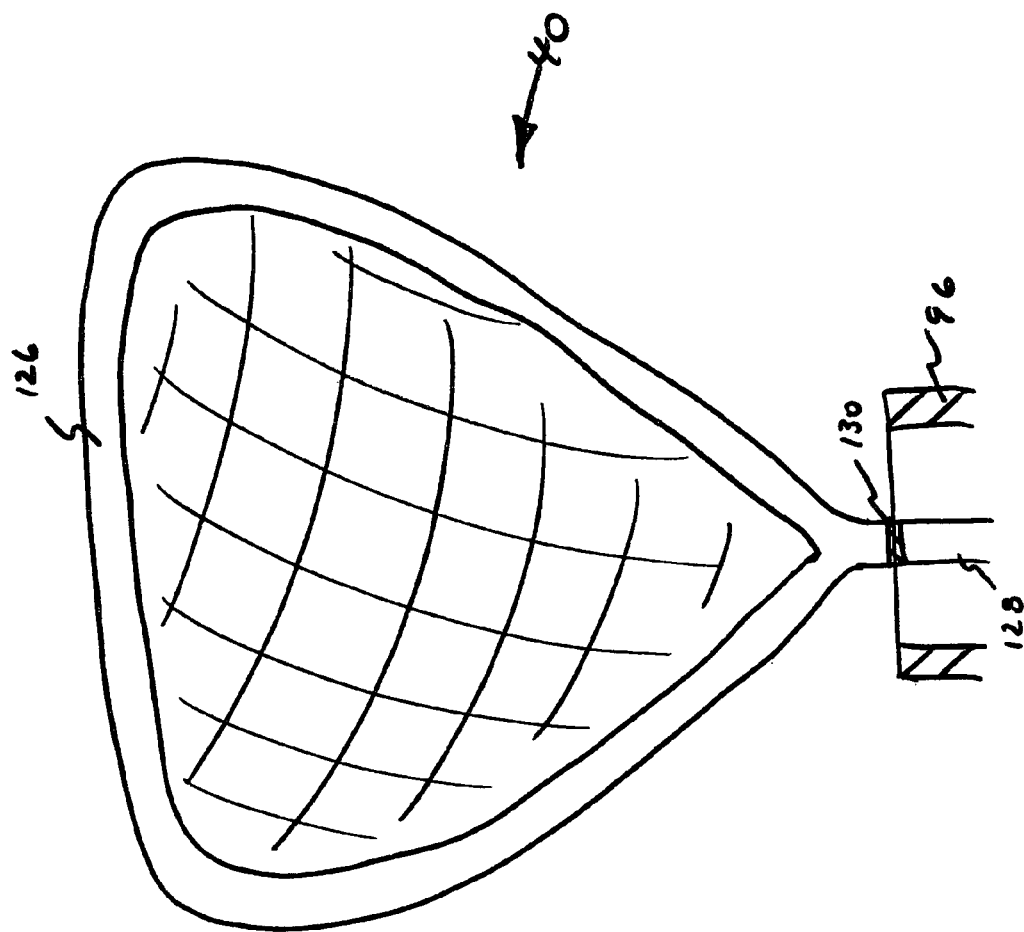
FIGS. 21A and 21B illustrate another embodiment of the deployment tool in accordance with the present invention.
Figure 21A:
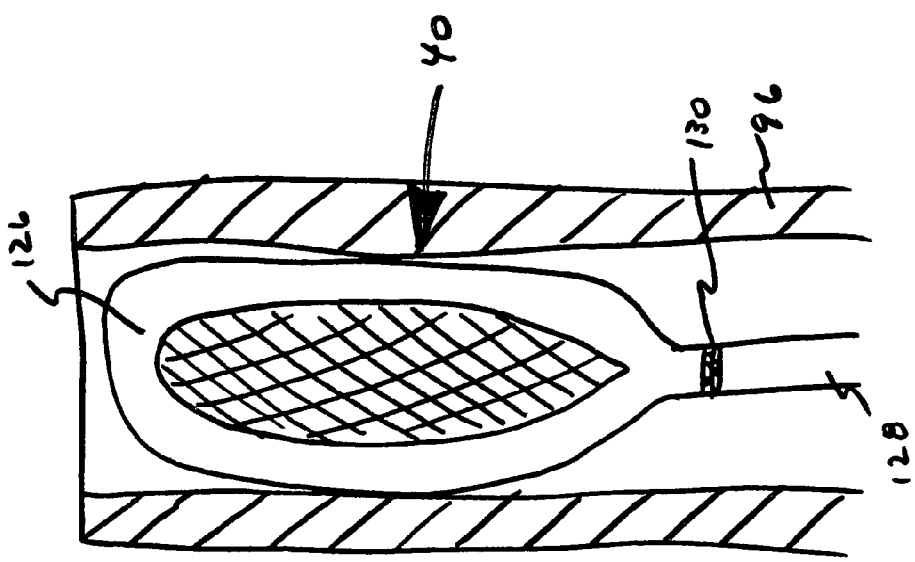

Another embodiment of the deployment tool of the present invention is shown in FIGS. 21A and 21B. The deployment tool comprises a catheter 96 and an inflatable tube 126 attached to the perimeter of the device or implant 40. The inflatable tube 126 includes an inflation lumen 128 that is connected to the tube 126 and runs along the length of the catheter 96. The device 40 is deployed in the uterine cavity 44 according to the above-described methods. The tube 126 is then inflated, causing the implant 40 to conform to the internal geometry of the uterus. The tube 126 may either be sealed (at its connection 130 with the inflation lumen 128) or disconnected from the inflation lumen 128 by twisting the catheter 96. Therefore, the tube portion 126 of the deployment tool remains in the uterus 42 in either an inflated or deflated state.

Alternatively, the implant 40 may have a self-expanding structure attached to its perimeter to motivate it to unfold. This structure may consist of a material that has a memory and/or spring-like structure or behavior (i.e. elastic properties). Examples of representative materials include, but are not limited to, metallics, such as Nitinol® or stainless steel, and polymerics, such as nylon, acetal or propylene.

Figure 22A:
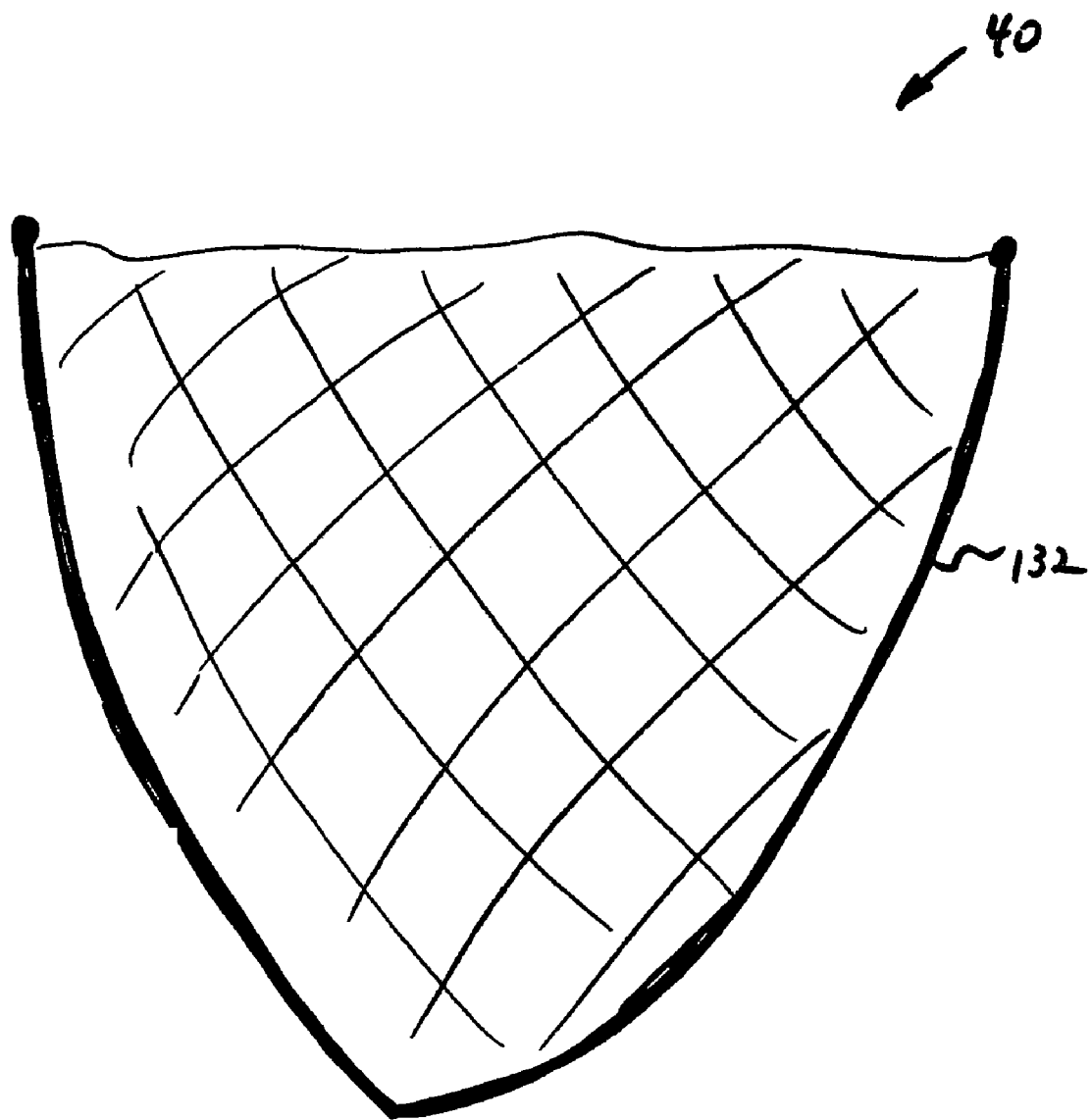
FIGS. 22A-22B illustrate perspective views of embodiments of a self-deploying implant structure in accordance with the present invention.
Figure 22B:
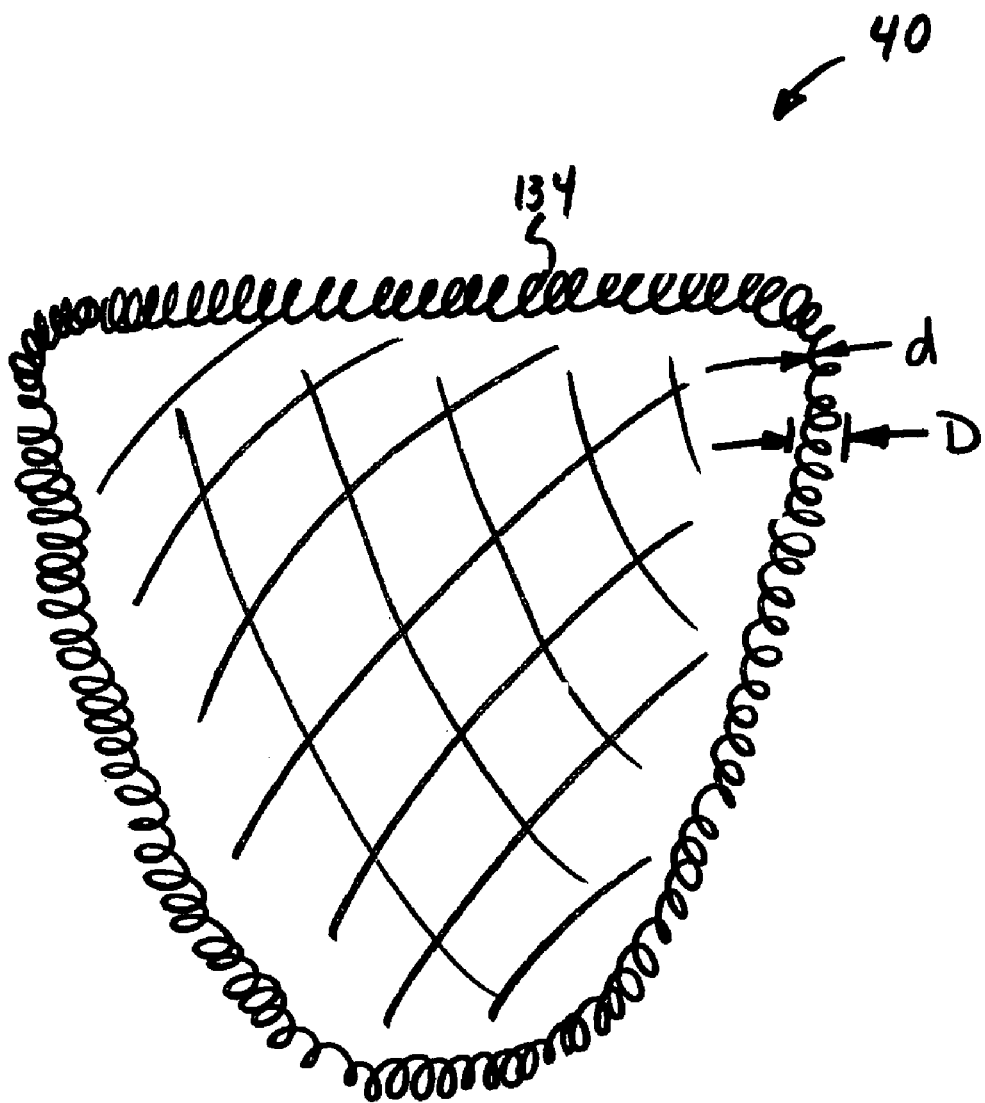

In one embodiment, shown in FIG. 22A, the self-deploying structure is a wire 132 that is attached to a portion of the perimeter of the implant 40. The wire 132 is made of a thermally activated material, such as Nitinol®, that expands in response to the patient's body temperature. Alternatively, the frame of the device comprises a very compliant, tightly wound spring 134. Referring to FIG. 22B, the wire diameter of the device, d, is approximately 0.001 inch (0.025 cm) and the spring diameter, D, is about 0.010 inch 0.25 cm). However, other spring configurations may also be used with the present invention. The garter-like spring 134 self-expands upon deployment from the catheter 96 and spreads the device 40 within the uterine cavity.

Figure 23:
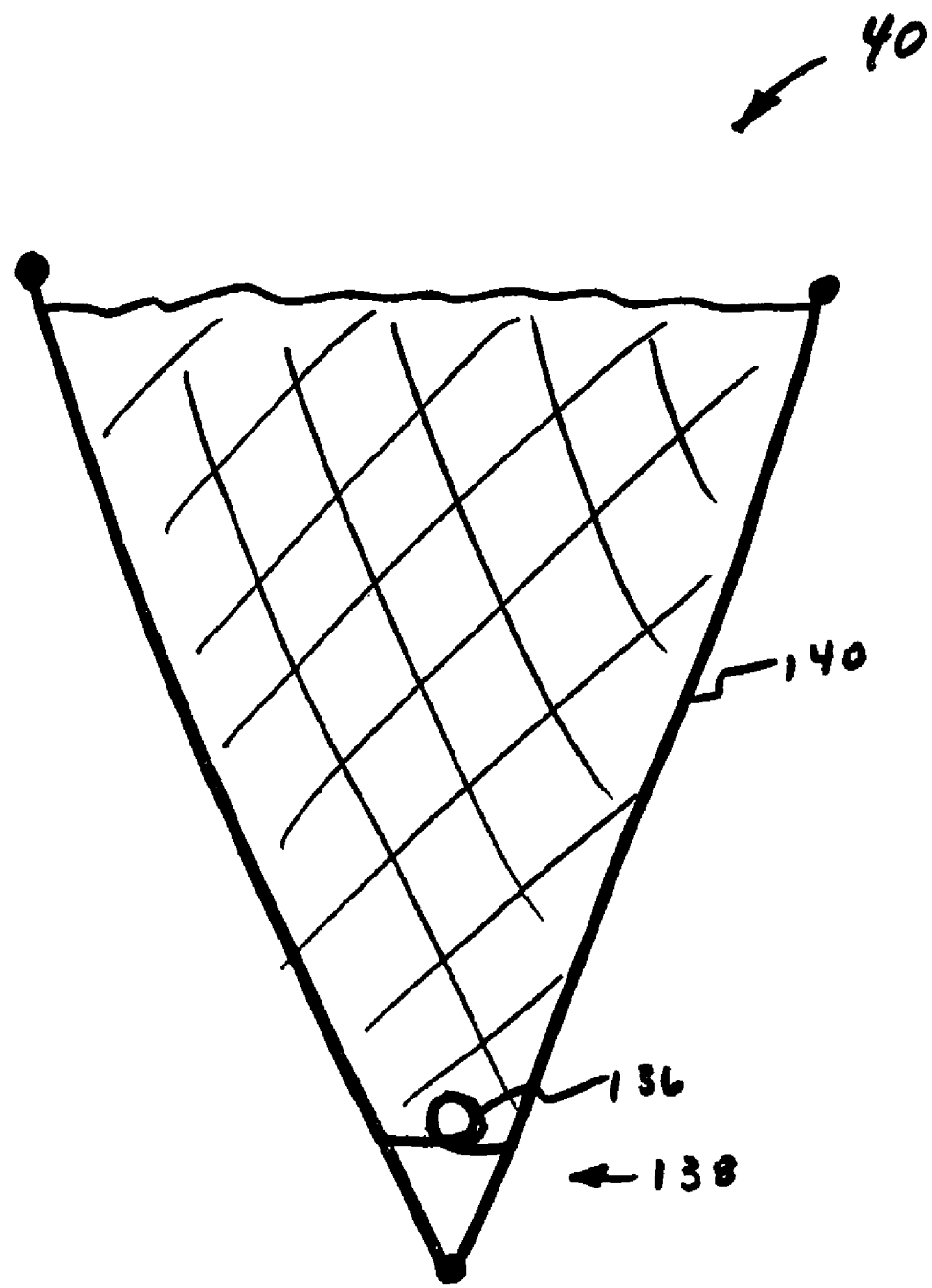
FIG. 23 illustrates an alternate embodiment of the implant in accordance with the present invention.
Figure 24:
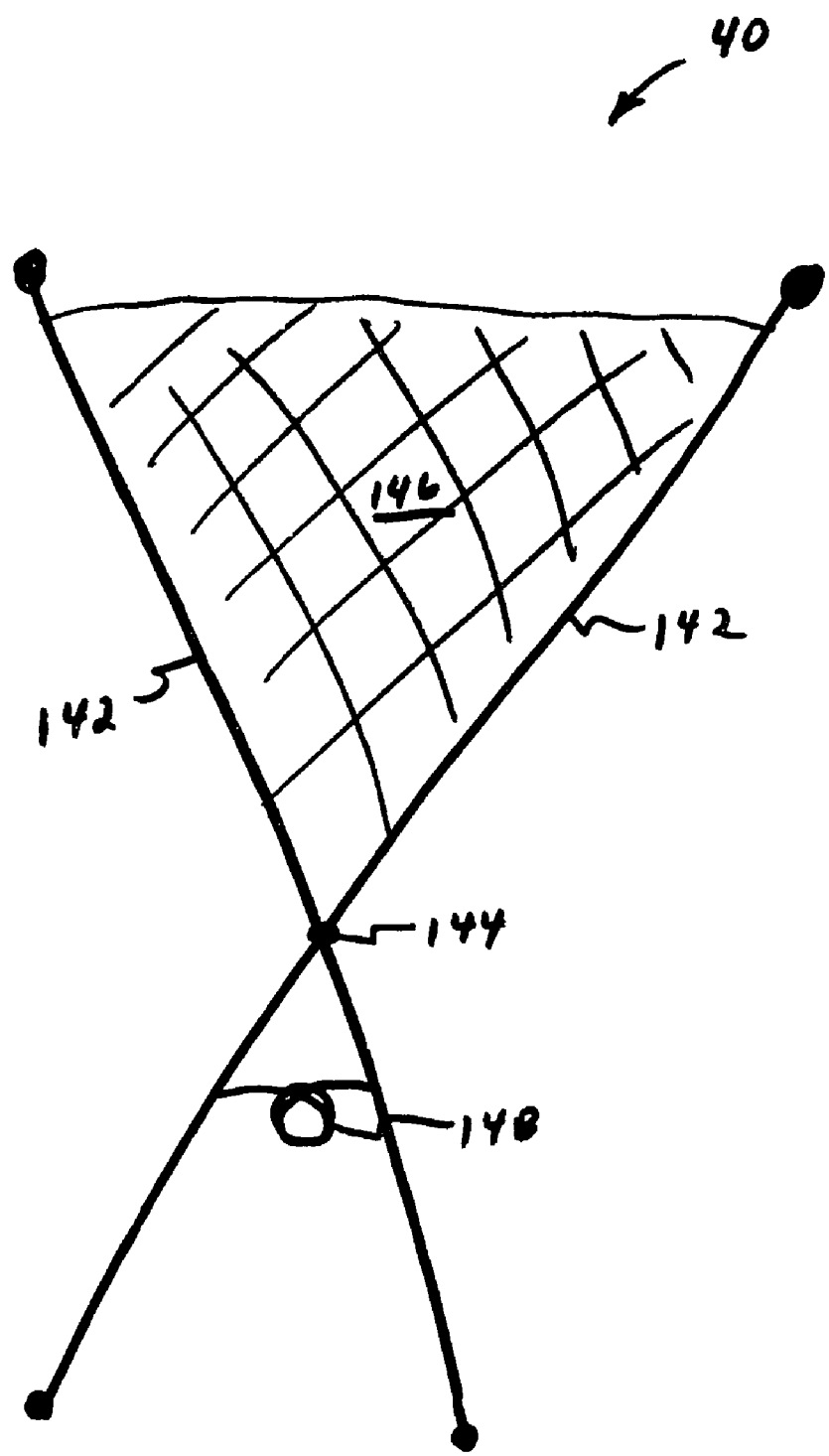
FIG. 24 illustrates another embodiment of the implant in accordance with the present invention.

In an alternate embodiment, shown in FIG. 23, a spring 136, located near the base 138 of the implant 40, forces the wire frame 140 of the device 40 into an expanded configuration after the device 40 is deployed from the catheter 96. In yet another embodiment, the wire frame 142 of the device 40 includes a pivot point 144 near its base. Referring to FIG. 24, in this configuration, the wire frame 142 forms an "X"-shaped device 40, with the mesh 146 attached to the upper-half of the "X" and the spring 148 attached to the opposite, lower half of the "X." As in the previous embodiment, after the device 40 is deployed from the catheter 96, the spring 148 forces the lower half of the frame 142 to expand, consequently forcing the upper half to also expand. This, in turn, causes the mesh portion 146 of the device 40 to evenly spread within the uterine cavity.

Figure 25:
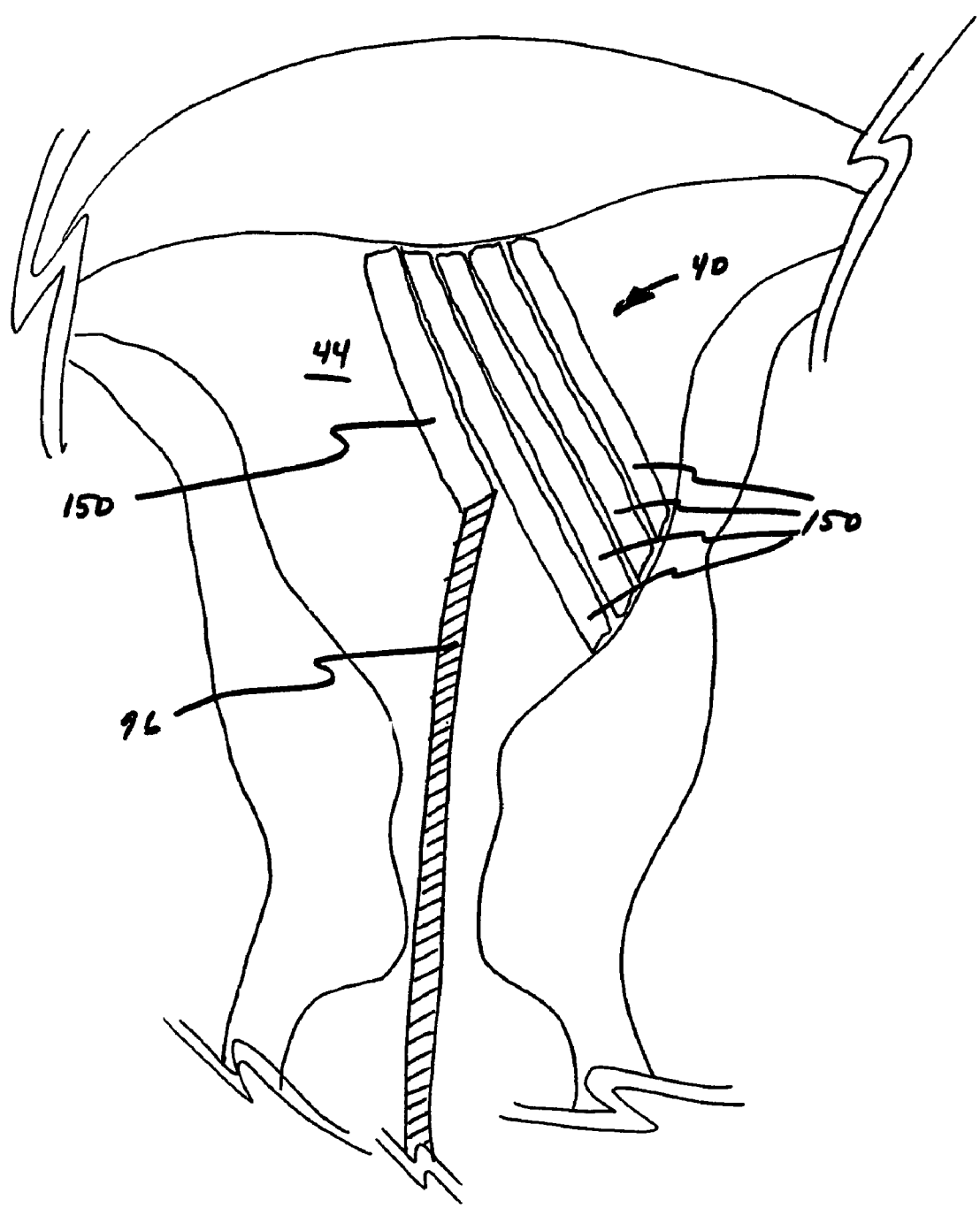
FIG. 25 illustrates an embodiment of a deployment device and implant in accordance with the present invention.

In an alternate embodiment, the device 40 is comprised of mesh strips 150 cut into small, thin rectangles, ovals or other various shapes. The mesh strips 150 are loaded into the cannula 96 and deployed by the physician in a manner similar to those described above. The configuration of the device 40 together with the deployment method allows for accurate placement of the device 40 within the uterine cavity 44, as shown in FIG. 25. In particular, the mesh strips 150 can be placed adjacent to each other, thereby creating a uniform covering. This method allows the physician to deploy the device 40 to specific areas or sites within the uterus (similar to the method by which carpeting is laid in a room or icing is piped onto a cake).

Figure 26:
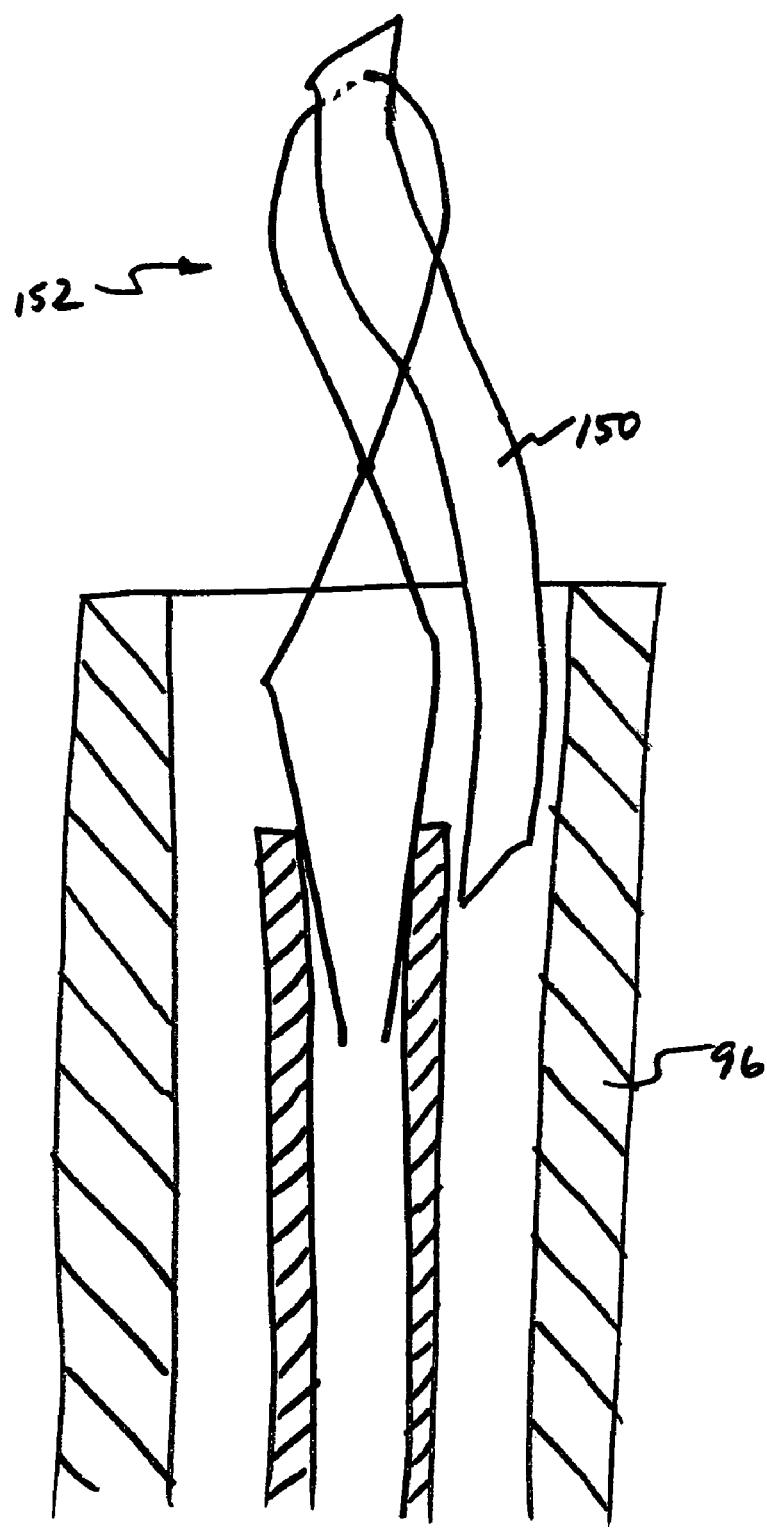
FIG. 26 shows an alternate embodiment of a deployment device and implant in accordance with the present invention.

In yet another embodiment, shown in FIG. 26, a tweezer-like device 152 is used to place the strips of mesh 150 into the uterine cavity. The physician manipulates the tweezer 152 to grab onto one end of a mesh strip 150. With the catheter 96 properly positioned transcervically within the patient's uterus, the tweezer 152, together with the mesh strip 150, are inserted into the catheter 96. The physician manipulates the tweezer 152 to accurately position the strip 150 onto the endometrium. The strip 150 is then released from the tweezer 152 and the process repeated until the uterine cavity is covered with strips of mesh 150. As described above, this method is similar to a carpeting-type approach.

Figure 27:
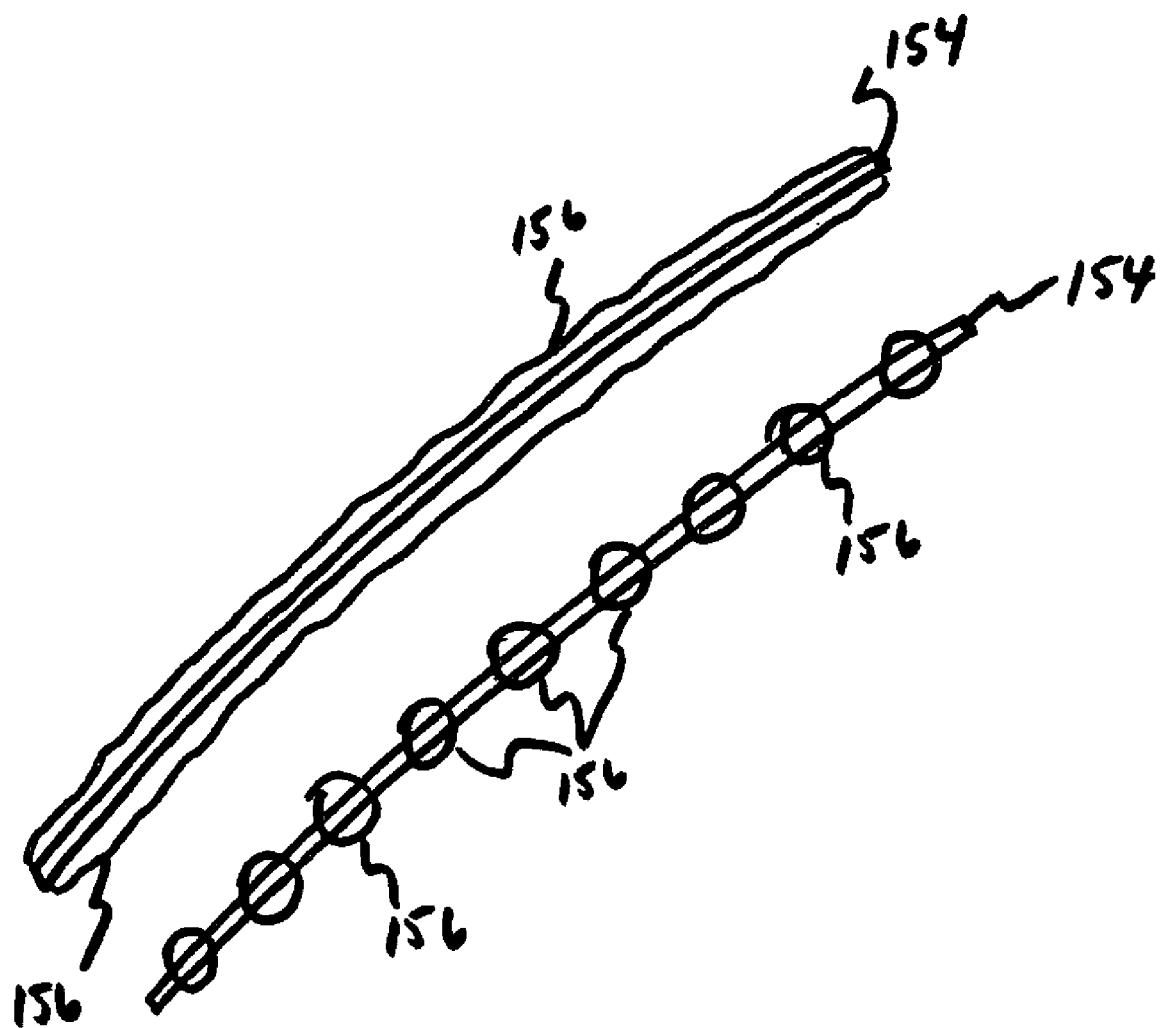
FIG. 27 illustrates an alternate embodiment of the implant in accordance with the present invention.

Alternatively, the mesh strips 150 of the carpeting technique can be configured as continuously deployable strips (not shown). In particular, the strips are loaded into the cannula 96 of the deployment tool such that as each strip is deployed, the next strip is automatically exposed or positioned for deployment. This technique is similar to the method by which Kleenex® is automatically dispensed from a tissue dispenser. In addition to mesh strips, the implant 40 can be configured as threads/monofilaments 154 loaded with an adhesion creating substance 156. The substance 156 may be a coating, beads or other components adhered to the threads, as shown in FIG. 27.

In yet another embodiment, the device 40 of the present invention is comprised of mesh particles. The mesh particles may be created by chopping or grinding the mesh material to a predetermined size. The mesh particles are then loaded into the cannula 96 and deployed as described above. This deployment method is similar to the manner by which insulation is blown into an attic or other open space. In an alternate embodiment, the mesh particles can be configured as atomized micro-particles, semi-rigid foam, suspended aggregate, particulates, powder or other similar forms, including combinations thereof.

Figure 28A:
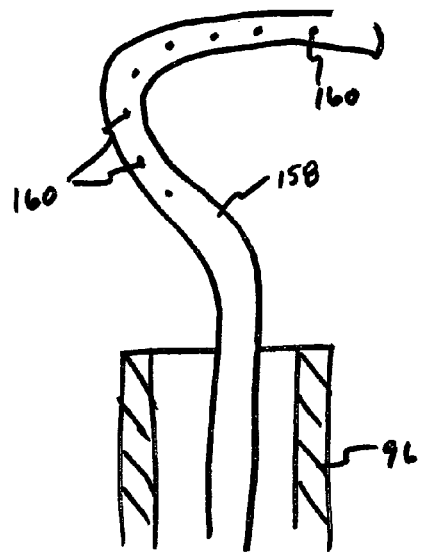
FIGS. 28A-28C illustrate an embodiment of a catheter used in accordance with the present invention.
Figure 28B:
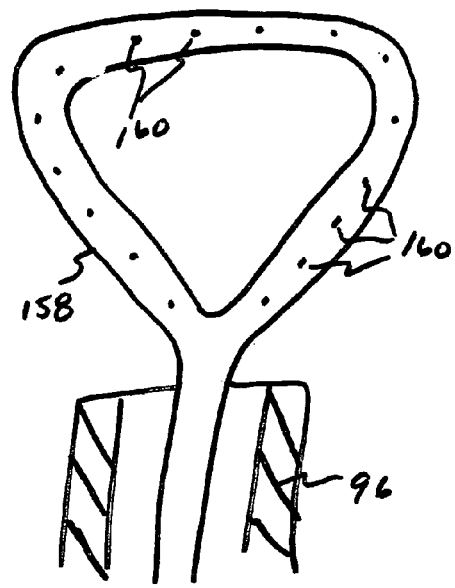
Figure 28C:
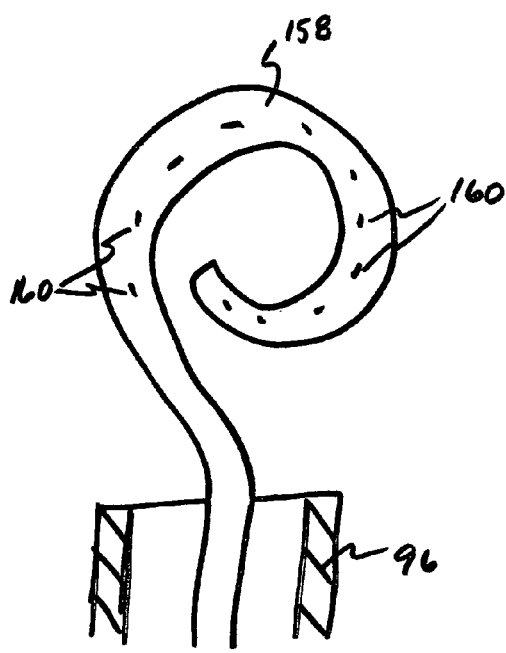

Alternatively, the mesh particles may be suspended in a liquid, gas, foam or other flowable substance that uniformly disperses the mesh particulate when injected by the cannula or catheter 96 into the uterus 42. Preferably, the flowable substance is biocompatible and capable of being absorbed by the body. When configured in a liquid or semi-liquid form, the device 40 is dispensed and spread within the uterus 42 using a syringe, instead of a stylet, and a fluid-dispensing catheter 96. As shown in FIGS. 28A-28C, the catheter includes a cannula or lumen 158 capable of dispersing fluid in the uterus 42 via one or more holes/ports located in the cannula 158. The dispensing cannula 158 may be configured in the form of a bend, curve, pig-tail, open-loop, closed-loop or other similar configuration. In addition, the cannula 158 may also be designed to advance beyond the distal end of the catheter 96 during the deployment procedure and retract into the catheter at the conclusion of the procedure. The curved, distal end of the cannula 158 may be flexible so that it straightens as it is retracted into the catheter 96. Further, a guide-wire (not shown) may also be formed within the cannula 158 to steer and/or guide the cannula 158 within the uterus 42 of the patient.

In one embodiment, the particular composition or material make-up of the flowable substance is such that its viscosity can be modified through thermal changes. The thermal changes may include those produced externally or generated by the patient's own body temperature. One example of a thermally-sensitive material is a polymer substance. However, it should be noted that other thermally-sensitive materials not specifically disclosed, but well known in the art, may also be used with the present invention.

Figure 29:
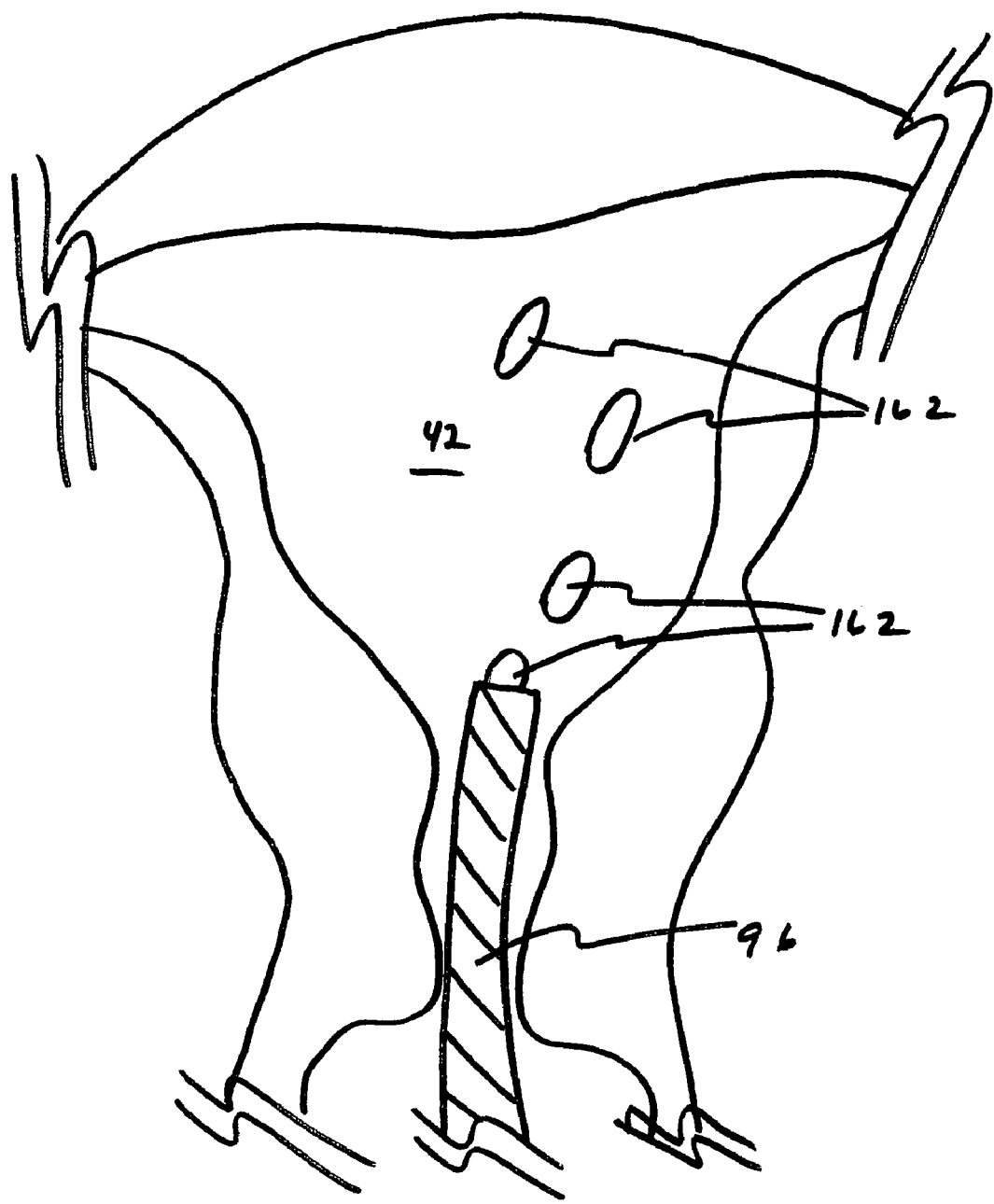
FIG. 29 shows another embodiment of the implant in accordance with the present invention.

In an alternate embodiment, the adhesion forming material is encapsulated in a hydrophillic membrane, elastomeric compound, a gelatin, or other similar dissolvable material. Referring to FIG. 29, one or more capsules 162 are placed in the uterus 42 of the patient using a catheter, cannula or other type of dispensing device 96. A stylet (not shown) may be used to push and position the capsule(s) 162 in the uterine cavity. Contact with the uterine tissue causes the membrane of the capsule 162 to dissolve and, thereby, deploy the encapsulated material. Alternatively, the capsule 162 could be irrigated with a separate solution dispensed from the catheter 96 to accelerate the dissolution process. The encapsulated material may be a self-expanding or self-spreading material, such as a liquid, gel, foam, shaped-foam or other similar material. The self-expanding material may be absorbed by the tissues during adhesion formation. Alternatively, the self-expanding material may be non-absorbable and, thereby, forms the scaffolding or structure for tissue in-growth and subsequent adhesion formation.

Figure 30A:
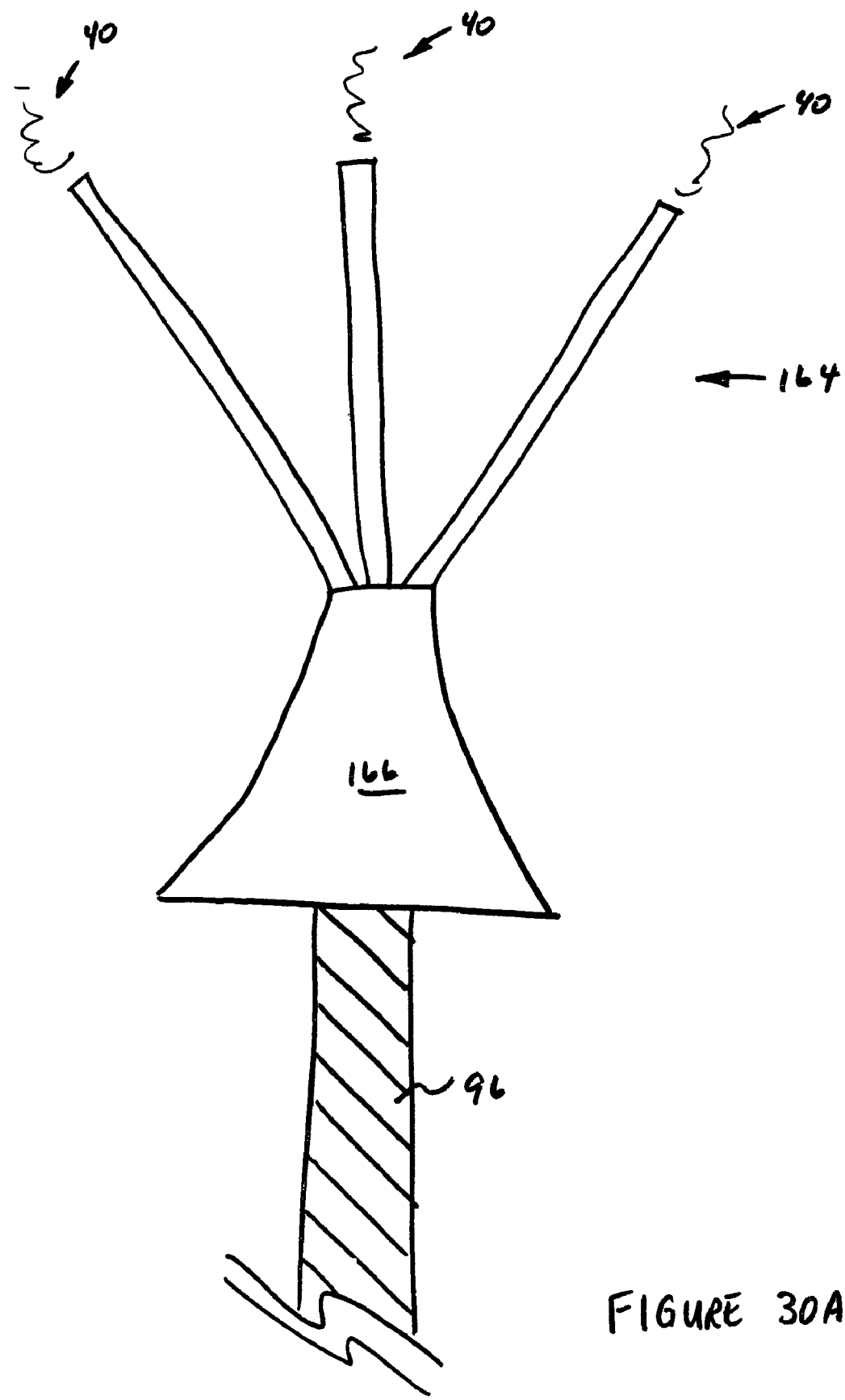
FIGS. 30A-30C illustrate an alternate embodiment of a deployment tool in accordance with the present invention.
Figure 30B:
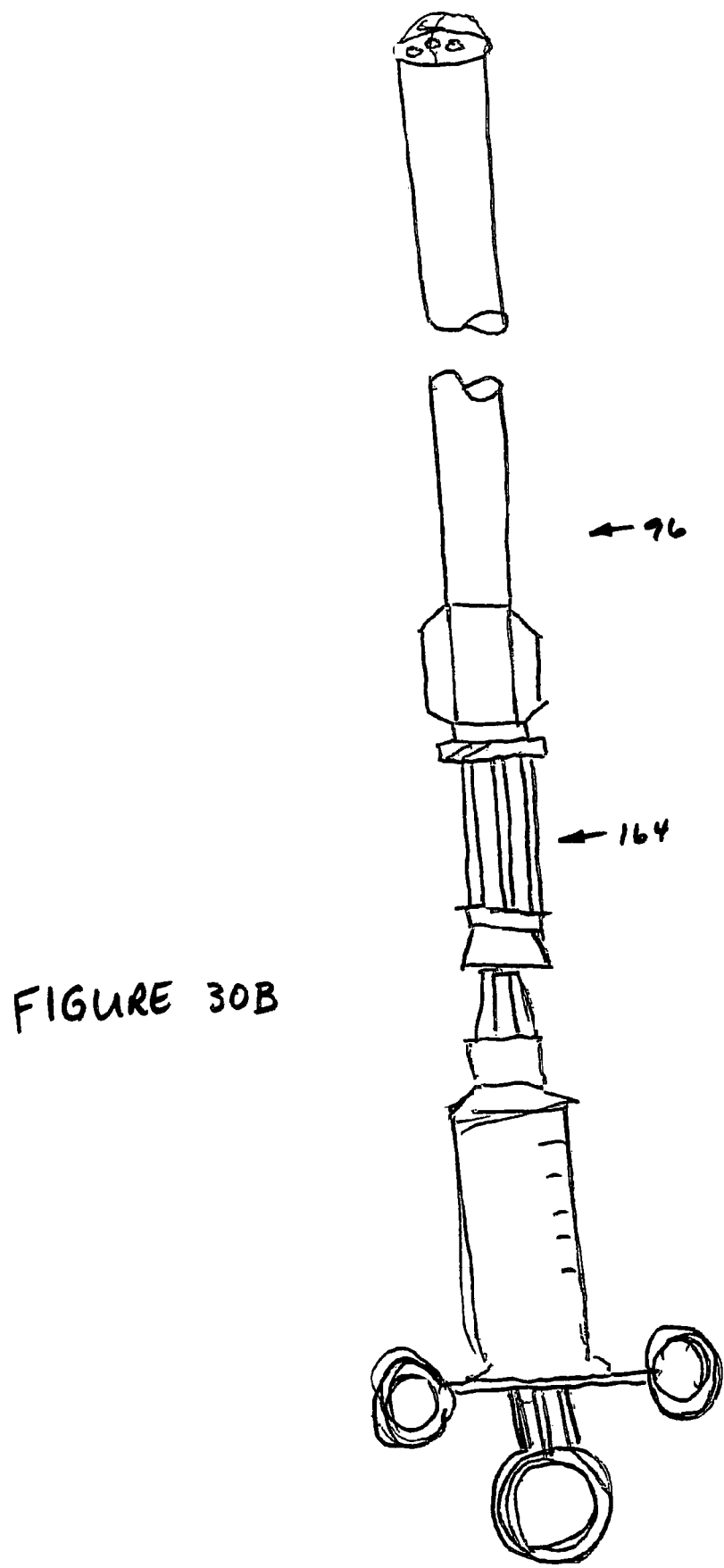
Figure 30C:
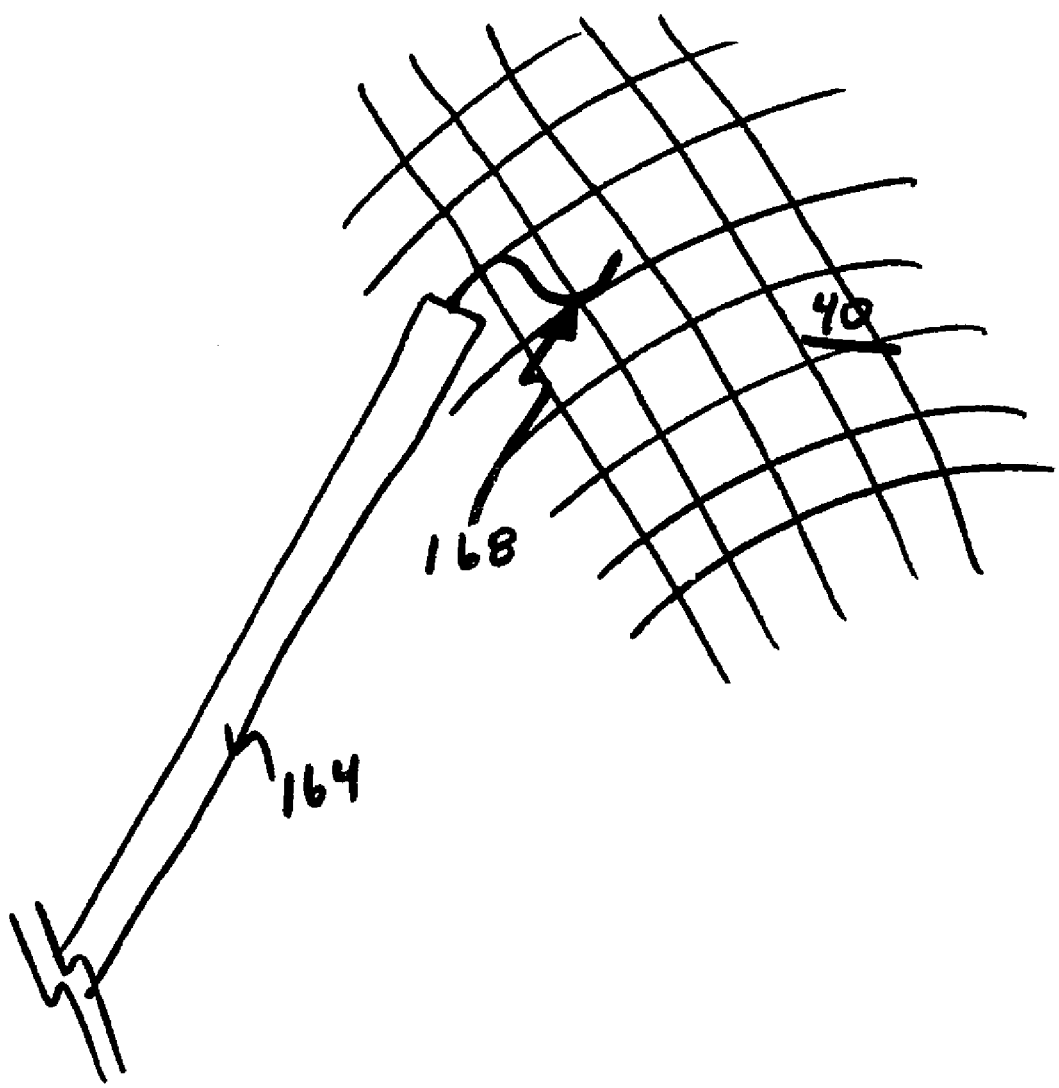

In an alternate embodiment, shown in FIGS. 30A and 30B, the deployment tool comprises a para-tube 164 housed within a catheter 96 and a funnel 166. The funnel 166 functions to dilate the cervix and split the para-tube 164 into a fan-shaped configuration as it is advanced through the funnel 166 and into the uterus 42 of the patient: The expanded structure of the para-tube 164 dispenses the fluid, gas or foam-type implant 40 throughout the uterine cavity. After the implant 40 is dispensed within the uterus 42, the para-tubes 164 are retracted back into the catheter 96 and the tool is removed from the patient. Referring to FIG. 30C, in another embodiment, hooks 168 located on the distal end of the para-tubes 164 can be used to catch or grab onto the mesh of the implant 40 and spread the device 40 within the cavity of the uterus 42. The retraction and removal methods are similar to those previously described.

After insertion of the device 40 is completed, a vacuum can be applied to the uterine cavity via the cervical canal. Alternatively, the implant or device 40 itself may also have a filtering component (compatible with the uterine tissue) integrated into the device 40 that permits the evacuation of air via a vacuum applied to the filtering component. As such, a mating device is attached to the cannula 96/filtering component and is used to create a seal on the cervix 50. Applying a light vacuum via the mating device produces the seal. The vacuum helps the surrounding uterine tissue make better contact with the inserted device 40 and, thereby, assists in luminal bridging or adhesion creation between the uterine surfaces. The length of time that the vacuum is applied to the uterine cavity is dependent upon the condition of the patient and the procedure being performed; however, vacuum is generally applied for a time period of several minutes.

A plug or cap, similar to those previously described, may be inserted into or placed over the cervix to also help contain the device 40. The cap prevents movement of the device 40 or migration of the material, especially when the material is in a liquid configuration. The cap may be made of a material that, over a period of time, is absorbed by the surrounding tissue. This configuration of the cap eliminates the need to remove the cap at a later time and/or during a secondary procedure.

Figure 31A:
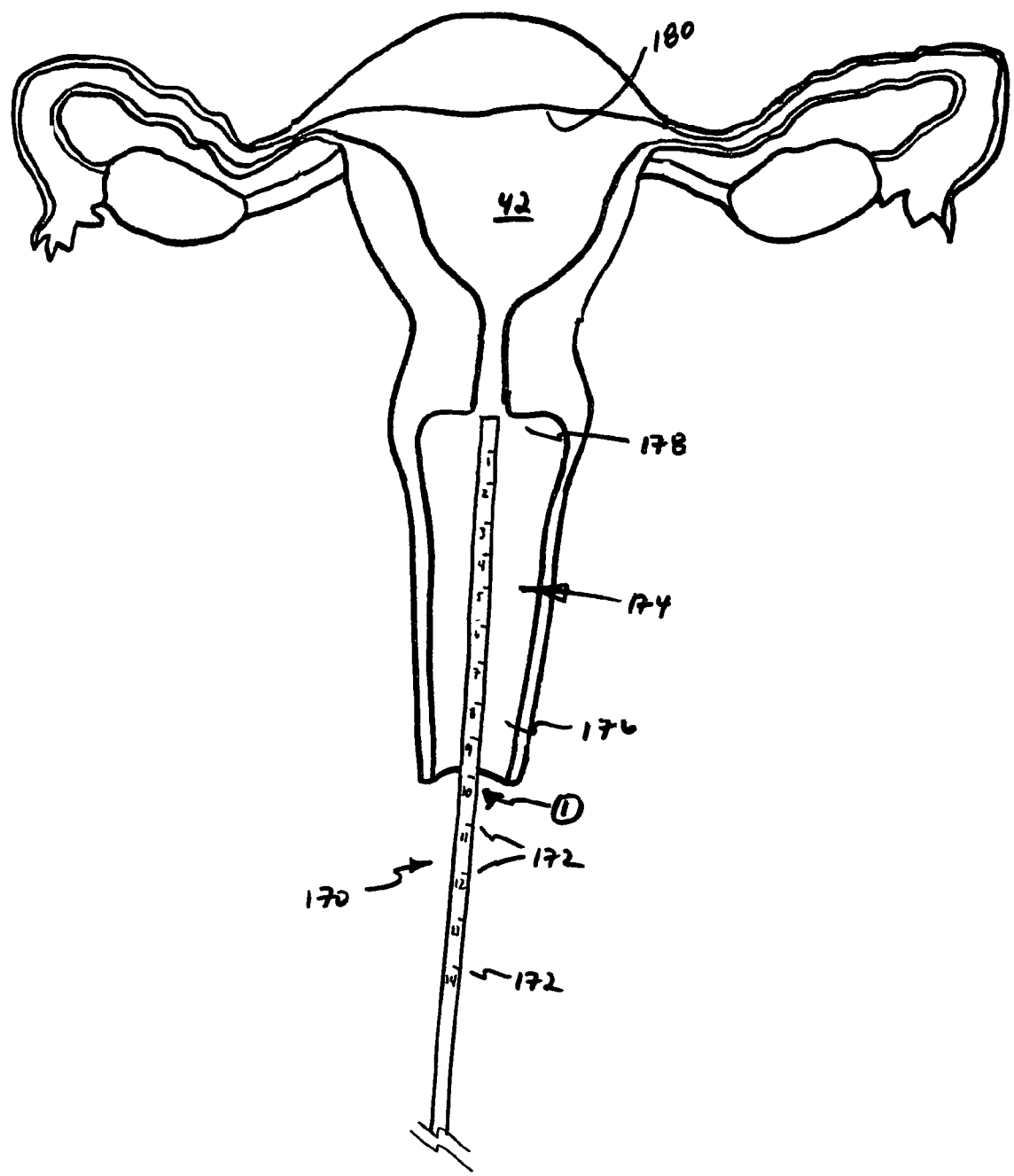
FIGS. 31A-31B illustrate an embodiment of a tool used in accordance with the present invention.
Figure 31B:
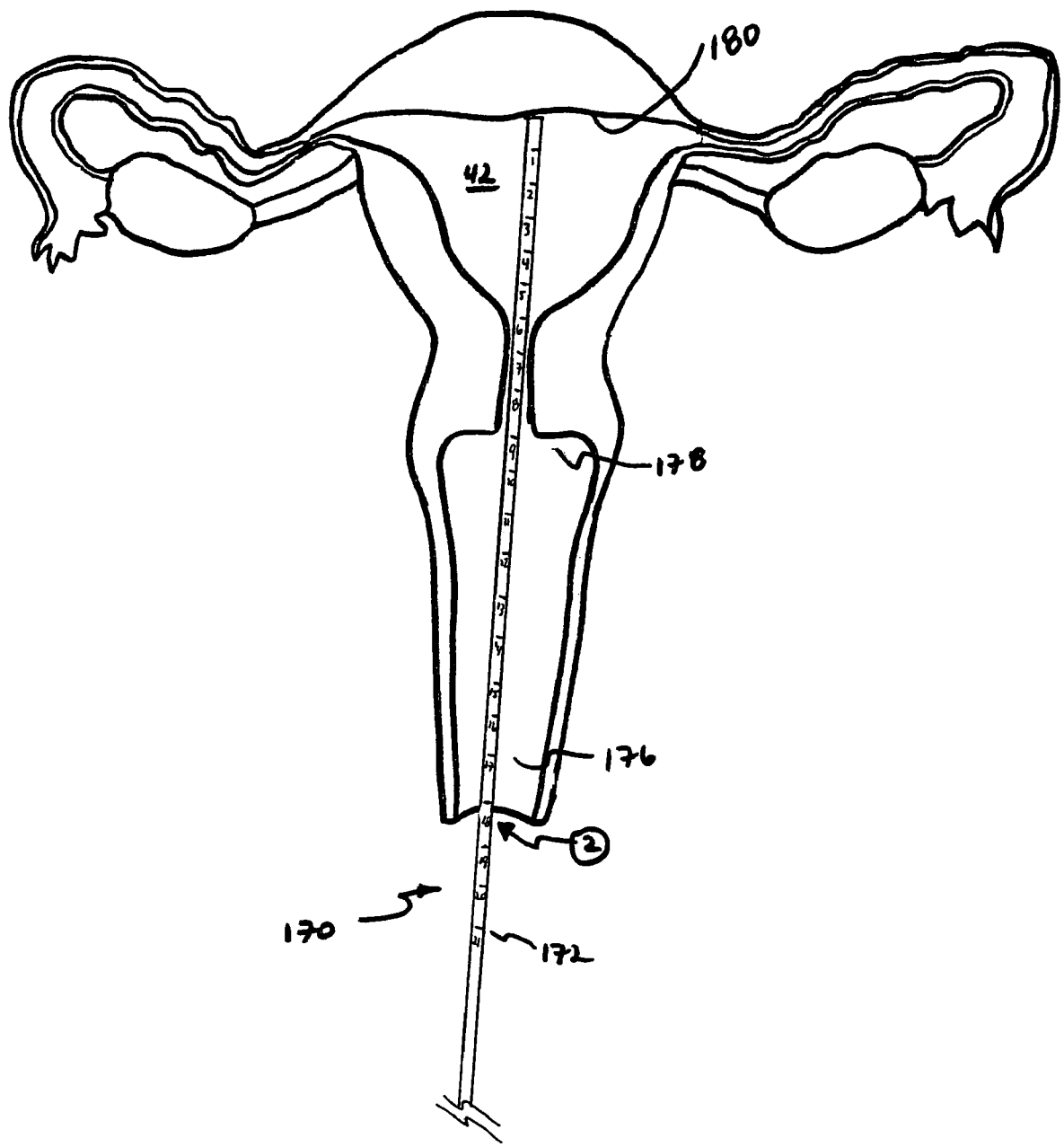

An additional tool or device may also be used in conjunction with the device of the present invention. Referring to FIGS. 31A and 31B, the tool comprises a cannula, catheter or lumen-based device 170 having graduated indicators or markings 172 along the length of the device 170. During use, the distal end 174 of the tool 170 is inserted into the vagina 176 of the patient. When the tip of the catheter 170 reaches the cervical opening 178, the catheter marking visible at the location of the vaginal opening (i.e. reference point 1) is noted by the physician/user. The catheter 170 is further inserted through the cervix and into the uterus 42 of the patient until it abuts the rear wall fundus 180 of the uterus 42. When the tip of the catheter 170 abuts the rear wall 180 of the uterus 42, the catheter marking visible at the vaginal opening (i.e. reference point 2) is also noted by the physician. As such, the physician would then use the two reference points to determine the length of the uterus 42 and/or fill volume of the uterine cavity.

In general, the markings on the device 170 allow the physician to determine the two points of reference within the filling range of the uterus 42. During use, the physician would begin to dispense the fluid-implant when the catheter 170 was at its maximum depth in the uterus 42. The physician would continue to dispense the fluid-implant and simultaneously retract the catheter 170 until the tip of the catheter 170 reached the minimal depth (indicated by reference point 2). In this configuration, the markings act as a guide to give the physician an understanding of where to fill. Further, the markings may also enable the physician to determine the shape of the uterine cavity and the amount of material to dispense (via depth measurements and, possibly, an associated algorithm or chart).

Marker Technology

In addition to reducing and/or eliminating menorrhagia, the device 40 of the present invention can also be used as a uterine marker. The marker provides the physician with the ability to visualize and quantify any endometrial growth or abnormality, such as endometrial hyperplasia and/or endometrial cancer. In this regard, the marker may be used as an absolute reference from which the physician may gage the difference of other features (growths or other irregularities). The marker of the present invention may also be used to assist the physician in determining the plane or location of view (e.g. determines the depth of the imaging plane) such that the cross-section or outside/inside diameters of the uterus may be determined and compared with subsequent diagnostic procedures. The marker may also be used by the physician when performing a non-invasive biopsy, using the marker as a landmark for guidance to the site under an imaging technique. Therefore, the marker acts as a landmark to assist the physician in determining visual or dimensional differences in the uterus.

In general, the marker component is biocompatible and stable when embedded or implanted over long periods of time (i.e. permanently) within tissue formed on the interior of the uterus 42. As such, the marker material should have good dimensional stability and allow for visualization when imaged using ultrasound, magnetic resonance imaging (MRI), computed tomography (CT), x-ray or other common imaging technique, including any combination of such techniques. The marker can be incorporated into the implant device 40, deployment device, and/or pretreatment device previously described, or can be provided as a stand-alone device.

Figure 32:
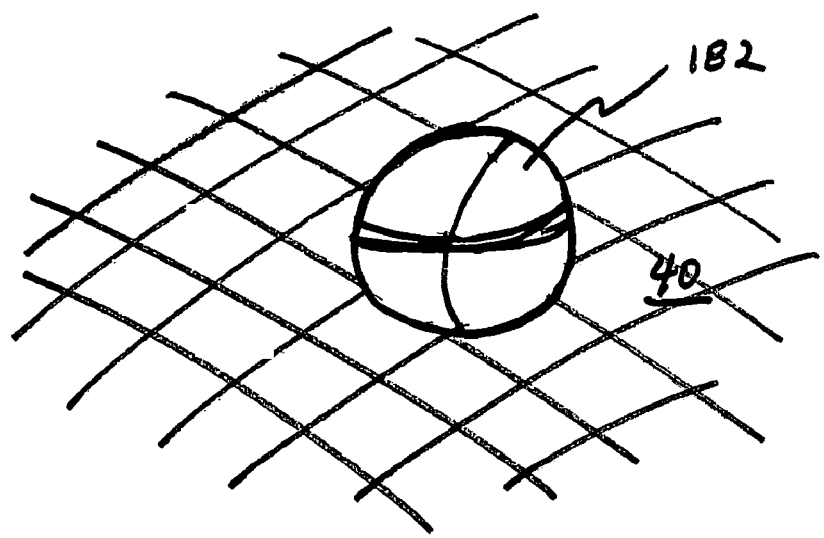
FIG. 32 shows an embodiment of a marker in accordance with the present invention.
Figure 33:
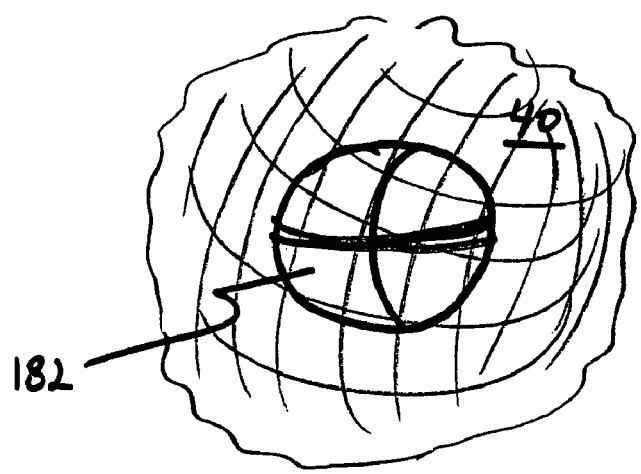
FIG. 33 shown an alternate embodiment of a marker in accordance with the present invention.

When combined with or within the implant 40, the marker allows the physician to determine placement of the implant 40 (i.e. coverage, position, etc.), both short term and long term, and track/assess changes in the surrounding tissue. In one embodiment, shown in FIG. 32, the mesh or other adhesion promoting substance of the device 40 is connected to the marker 182 (configured as a bead) to ensure that the marker 182 remains in a fixed, known location. Referring to FIG. 33, in another embodiment of the invention, the marker 182 is suspended in the adhesion promoting substance 40.

As referenced above, the marker may be used either as a stand-alone device (i.e. diagnostic tool) or in combination with other procedures or implants previously described. In general, the stand-alone marker design would be intended as a diagnostic tool and used on normal/healthy women for assisting in detection of potential abnormalities within the uterus (such as fibroids, cancer, or other abnormalities). The stand-alone marker device may vary in size from that of an IUD to a bead as small as 0.04 inch (0.1 cm) in diameter. In general, the marker device should be small enough to allow it to pass through the catheter or deployment device and be imaged via ultrasound or other means. Further, the size and/or shape of the marker device may also be adjustable to allow the marker to conform to the configuration of the uterus. Therefore, the size of the marker device may either be selected to correspond to one of a predetermined range of uterus sizes or adjusted at the time of insertion to conform to the patient's particular uterus size/shape.

In another embodiment of the invention, the marker may be a component that is used to hold the device/implant in place, thereby acting as an anchor point. The marker may be anchored to the walls or fundus of the uterus to maintain its position and minimize the possibility for expulsion. The marker may be delivered with a device, such as a catheter or other type of deployment device, that allows for attachment of the marker to the uterine walls. Alternatively, the marker could also be a feature of the implant 40 and delivered via an implant deployment tool/device.

The ideal marker allows for imaging to be performed at any angle and the marker to always be viewed at true length. An example of such a design is a marker with a spherical shape. Alternatively, a hollow, equilateral triangular shape or design may also be used. In this configuration, the viewing angle is in true position when all sides of the triangle are of equal length. However, numerous other shapes may also be used to image both two-dimensional and three-dimensional views. Examples of applicable marker shapes or designs include sphere, tube, donut, hollow sphere, curved object or any other geometric shape of a known size.

In addition, the marker may consist of a series of spaced spheres/markers to provide the physician with a multiple number of nodes or test sights to measure the thickness of the myometrium, endometrium, or other desired tissue or site. The multiple markers may be equally spaced or spaced at intervals that are critical points of measurement. Further, the multiple markers may be the same shape/size or different shapes/sizes to differentiate between the individual markers. The physician will be able to know which marker the measurements are taken at to create a repeatable measurement at each site that can be monitored during check-ups.

As previously described, the marker is externally imaged using any of the above-mentioned techniques. For example, the ultrasound and x-ray based imaging techniques rely on different material densities for detection and/or imaging. Accordingly, the marker should have a density that is different from the density of the surrounding tissue. The density difference allows for the imaging device to precisely indicate the location of the marker and its relative distance to various features within the uterus, myometrium, cervix, etc. As such, the greater the density difference, the greater the image intensity.

A very broad range of materials may be used for the marker, since any material that has a density different from water (i.e. tissue) would be acceptable. Examples of these materials include, but are not limited to, polypropylene, ethylene, titanium, urethane, nylon, GORE-TEX®, PTFE, Nitinol®, stainless steel, proteins, or any type of biological material that is stabile (not resorbed or absorbed by the body; i.e. bone, teeth, etc.). In addition, the marker may be configured as either a solid or hollow component.

Surface finish of the marker may also be an important feature for visibility/imaging and tissue growth into the marker. For example, a rough surface finish is more readily viewable under ultrasound due to the defraction/deflection of sound waves. In addition, a marker configured with surface barbs or undercuts not only securely affixes the marker to the uterine tissue but also may promote tissue in-growth. Thus, overall device structure and material composition may enhance both imaging and in-growth of surrounding tissue into the marker.

Although only one marker is required, multiple markers may also be used. In particular, multiple markers may have the added benefit of allowing for more exact measurement or better visualization, depending on the placement of the marker to the area of interest.

In another embodiment of the invention, the marker may be made of a combination of materials to allow for multiple imaging modes. For example, the marker material may be a polymeric substance with metallics suspended in the resin. This configuration gives the marker combined polymeric and metallic characteristics which allow imaging of the marker in numerous formats. Alternatively, the marker may also be a hollow member that is filled with a liquid (for example, a drug) or gas capable of permeating the hollow member. The hollow member is then imaged to determine the amount of drug released and, thereby, act as a marker. In an alternate embodiment, after all of the liquid is diffused, the hollow member can be refilled using a syringe. This refilling technique would be similar to those used with subcutaneous access devices used in the IV drug dispensing industry.

In another embodiment of the invention, the marker comprises one or more coatings applied to the implant/device 40. Examples of such a device include a dyed mesh or coated ball. In addition, the coating may be dissolvable, thereby permitting the coated device to be initially imaged using one type of imaging technique and, after the coating is completely dissolved, imaged using an alternate, long-term imaging technique. One example of this type of marker configuration is a polymer bead coated with radiopaque ink that is water-soluble. The bead is initially imaged using x-ray fluoroscopy. After the ink is dissolved (generally within one to three days), the bead may be subsequently imaged using ultrasound. Further, the ink may be designed to dissolve due to the in-growth or formation of tissue on the marker. This would enable the physician to accurately determine when the adhesion has been sufficiently formed, since the ink/dye would be completely dissolved when the marker is fully surrounded with connective tissue (i.e. adhesions).

In an alternate embodiment, the marker may be a biological material that is reactive to any or specific cancerous cells and/or tissues. The reaction would cause the biological material to change its properties (such as density), making it imagable with an ultrasonic device or other imaging mechanism. Alternatively, the biological material may be a substance coated on the exterior portion of the marker that prevents liquid/moisture penetration. When the biological material contacts specific tissues/cells, the resulting reaction causes the protective coating to become porous. As the porosity increases, imaging contrast decreases. Thus, when the disease (specific tissues/cells) is in an advanced state, the marker is barely, if at all, imagable. In another embodiment, as the porosity increases, body fluids/liquid/moisture penetrate into the marker device, causing the physical structure of the marker to change. For example, the structure may be distorted, deformed, uniformly expanded in overall size, uniformly reduced in size, randomly expanded in size or randomly reduced in size. The degree of structural change may be used to indicate how advanced the disease state is.

Alternatively, the biological material may also cause a specific reaction when cancerous cells are encountered. For example, the reaction may create a response that promotes secretions through the cervix. The secretions could then be detected during patient examination or diagnosis using an appropriate swab or assay test.

Figure 34:
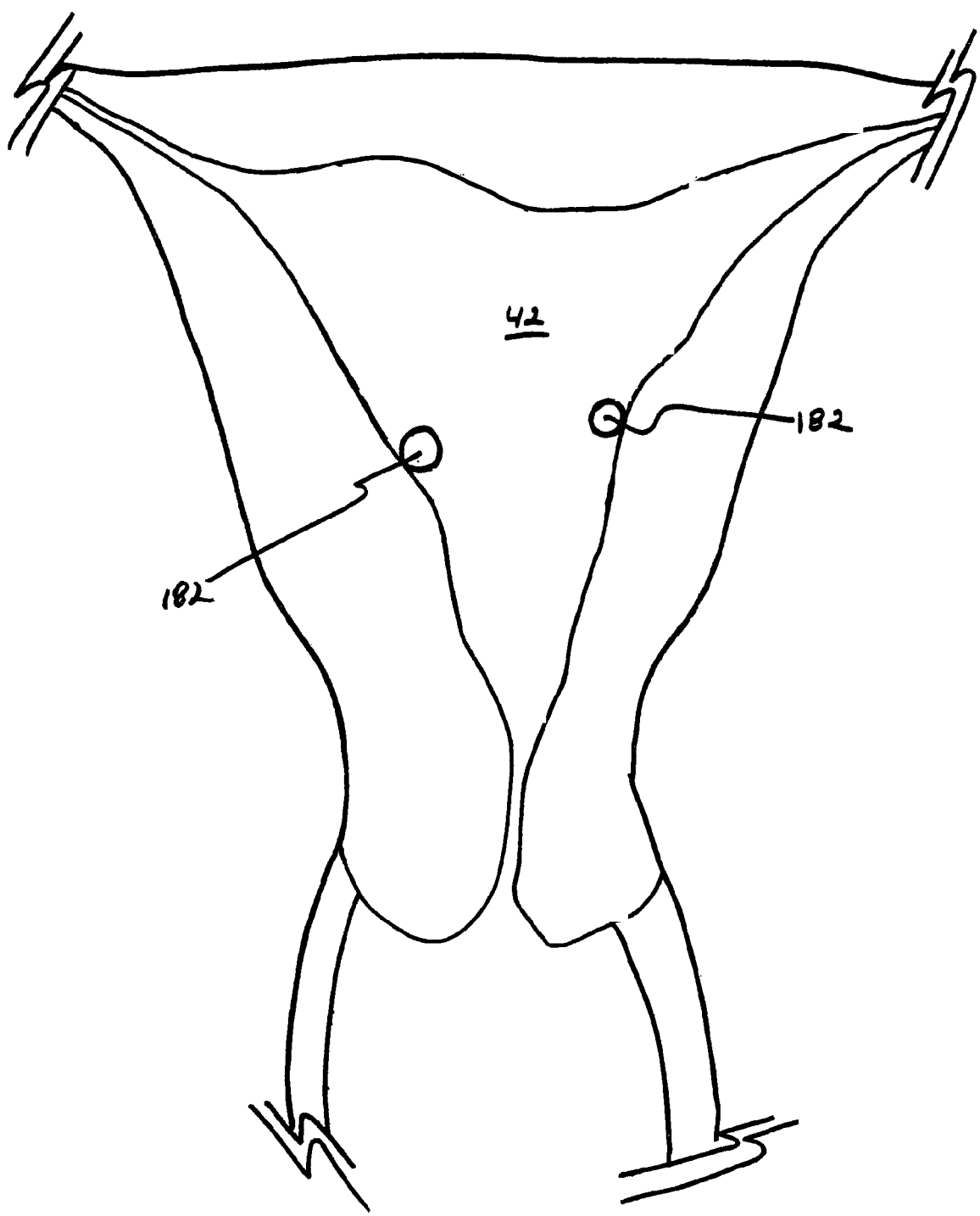
FIG. 34 illustrates a perspective view of an implanted marker in accordance with an embodiment of the present invention.

With the above parameters in mind, one preferred example of a uterine marker 182 is shown in FIG. 34, in conjunction with the uterus 42. With this one preferred embodiment, the uterine marker 182 consists of two marker components that are secured to the uterine walls at known locations. In this configuration, the uterine marker 182 can be formed into the delivery material of the implant/device 40 previously described. Alternatively, the uterine marker 182 can be deployed independently. Regardless, once in place, the uterine marker 182 provides the ability to externally image and, therefore, monitor one or more specific uterine locations and characteristics, for example the thickness of the endometrial tissue. The uterine marker 182 effectively provides a "baseline" of endometrial tissue thickness. This baseline value can be compared to subsequent readings to evaluate and quantify any changes in the endometrial tissue. For example, with the one preferred embodiment, the marker components can be initially imaged and a distance between the two components determined (i.e. calculated) and stored. At a later date, a new distance value can be determined by re-imaging the uterus 42, including the uterine markers 182. When a change in distance is found, an early identification of potential abnormalities is given, such as the formation of cancerous tissue.

Another example of a uterine marker comprises a bead formed of imagable material and secured to the endometrial tissue. The bead has a known diameter or thickness that is viewable by the imaging device. Additionally, the imaging equipment also provides an indication of the endometrial tissue level, typically in the form of different image densities (e.g. endometrial tissue appears lighter in contrast than a remainder of the uterine walls). By providing the bead with a known thickness, a relationship between the observed endometrial tissue thickness and the actual bead diameter/thickness can be made and noted. Subsequent observations/relationships can be noted and compared to this baseline measurement. Any changes can provide a preliminary indication of uterine abnormalities. Additional examples of the uterine marker include markers comprising three or more components (such as a T-shaped device) to provide an additional spatial orientation of the uterus.

Regardless of the exact form, the uterine marker greatly aids in the early detection of uterine cancer or other abnormalities, and offers a major benefit not available with conventional diagnostic techniques or procedures. With the uterine marker, any physician can easily and quickly evaluate the patient and image and measure the uterine marker locations and related attributes (such as distances between marker components) using conventional imaging equipment.

Other Applications

The above disclosed technology may also be used in the veterinary science field for treatment of similar disease states within animals. The use of the implant may be particularly beneficial to breeders, especially in treatment of large animals such as horses. Also, this implant system may have application in the treatment of similar disease states in primates or may be used to study the biology of intrauterine adhesions and its tissue morphology.

In addition to providing an effective means of treating uterine disorders, the device and method of use of the present invention effectively reduce pain, infections and post operative hospital stays. Further, the various treatment methods also improve the quality of life for patients.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of changing a gynecological condition of a female comprising:
   evaluating the condition of a uterus of said female;
   introducing a presterilized implant into said uterus with a delivery tool;
   contacting said implant with uterine tissue so as to induce a tissue response in said uterus;
   detaching said implant from said delivery tool;
   maintaining contact between said implant and said uterine tissue for at least until walls of said uterus adhere together and cause a changed gynecological condition in said female, wherein the contact between said implant and said uterine tissue is maintained at least until menorrhagia has been substantially eliminated in said female.

2. A method according to claim 1, wherein the contact between said implant and said uterine tissue is maintained at least until adhesions are formed in said uterus.

3. A method according to claim 1, wherein the contact between said implant and said uterine tissue is further maintained at least until contraception in said uterus is achieved.

4. A method according to claim 1, wherein said presterilized implant is coated with an adhesion inducing substance.

5. A method according to claim 1, wherein said presterilized implant is coated with a biologic coating prior to introducing said implant into said uterus.

6. A method according to claim 1, wherein said presterilized implant is formulated at least in part from polyester prior to its introduction into said uterus.

7. A method according to claim 1, wherein said presterilized implant is introduced through a delivery tool that comprises a catheter.

8. An implant for changing the gynecological state of a female comprising:
   a self-contained presterilized substance disconnectable from a delivery tool;
   said self-contained substance configured for causing a tissue response in uterine tissue; and,
   said self-contained substance sized and shaped for sufficiently contacting uterine tissue such that uterine walls of said uterine tissue adhere together and thereby cause a gynecological change in said female, wherein said self-contained presterilized substance includes a frame, at least a portion of which is covered by a mesh material.

9. An implant according to claim 8, wherein said self-contained presterilized substance is substantially covered by said mesh material.

10. An implant according to claim 8, wherein said mesh material is a polyester material.

11. An implant according to claim 8, wherein said self-contained presterilized substance is coated with an adhesion inducing substance.

12. An implant according to claim 8, wherein said mesh material is comprised substantially of polyester.

13. An implant according to claim 12, wherein said frame includes a plurality of linear extensions, at least two of such extensions sized and shaped to extend across a uterine wall.

14. An implant according to claim 13, wherein said at least two extensions are movable between a collapsible and a deployed position.

15. An implant according to claim 8, wherein said substance is sized and shaped so as to eliminate menorrhagia.

16. An implant according to claim 8, wherein said substance is sized and shaped so as to further cause contraception in said uterus.

17. A method of changing a gynecological condition of a female comprising:
   evaluating the condition of a uterus of said female;
   introducing a presterilized implant into said uterus;
   contacting said implant with uterine tissue so as to induce a tissue response in said uterus;
   maintaining contact between said implant and said uterine tissue at least until adhesions are formed in said uterus, said adhesions causing a changed gynecological condition in said female, wherein the changed gynecological condition is substantial elimination of menorrhagia.

18. A method according to claim 17, wherein the changed gynecological condition also includes contraception.

19. A method according to claim 17, wherein formation of said adhesions includes causing walls of said uterus to adhere together.

20. A method according to claim 17, wherein said presterilized implant is coated with an adhesion inducing substance.

21. A method according to claim 17, wherein said presterilized implant is coated with a biologic coating prior to introducing said implant into said uterus.

22. A method according to claim 17, wherein said presterilized implant is formulated at least in part from polyester prior to its introduction into said uterus.

23. A method according to claim 17, wherein said presterilized implant is introduced through a catheter.

24. A method of changing a gynecological condition of a female comprising:
   evaluating the condition of a uterus of said female;
   introducing a presterilized implant into said uterus;
   contacting said implant with uterine tissue so as to induce a tissue response in said uterus;
   maintaining contact between said implant and said uterine tissue at least until walls of said uterus adhere together, said adhering of said walls causing a changed gynecological condition in said female, wherein the changed gynecological condition includes the substantial elimination of menorrhagia.

25. A method according to claim 24, wherein the adhering of said walls includes the formation of adhesions in said uterus.

26. A method according to claim 24, wherein the changed gynecological condition further includes contraception.

27. A method according to claim 24, wherein said presterilized implant is coated with an adhesion inducing substance.

28. A method according to claim 24, wherein said presterilized implant is coated with a biologic coating prior to introducing said implant into said uterus.

29. A method according to claim 28, wherein said presterilized implant is formulated at least in part from polyester prior to its introduction into said uterus.

30. A method according to claim 28, wherein said presterilized implant is introduced through a catheter.

31. A method of changing a gynecological condition of a female comprising:
   evaluating the condition of a uterus of said female;
   formulating a presterilized implant at least in part from polyester;
   introducing said presterilized implant into said uterus;
   contacting said implant with uterine tissue so as to induce a tissue response in said uterus;
   maintaining contact between said implant and said uterine tissue for at least until walls of said uterus adhere together and cause a changed gynecological condition in said female, wherein the contact between said implant and said uterine tissue is maintained at least until menorrhagia has been substantially eliminated in said female.

32. A method according to claim 31, wherein the contact between said implant and said uterine tissue is further maintained at least until adhesions are formed in said uterus.

33. A method according to claim 31, wherein the contact between said implant and said uterine tissue is further maintained at least until contraception in said uterus is achieved.

34. A method according to claim 31, wherein said presterilized implant is coated with an adhesion inducing substance.

35. A method according to claim 31, wherein said presterilized implant is coated with a biologic coating prior to introducing said implant into said uterus.

36. A method according to claim 31, wherein said presterilized implant is introduced through a catheter.

37. An implant for changing the gynecological state of a female comprising:
   a presterilized substance in the form of a mesh material;
   said substance configured for causing a tissue response in uterine tissue; and,
   said substance sized and shaped for sufficiently contacting uterine tissue such that walls of said uterine tissue adhere together and therby cause a gynecological change in said female., wherein said presterilized substance includes a frame, at least a portion of which is covered by said mesh material.

38. An implant according to claim 37, wherein said mesh material is a polyester mesh material.

39. An implant according to claim 37, wherein said presterilized substance is coated with an adhesion inducing substance.

40. An implant according to claim 37, wherein said mesh material is comprised substantially of polyester.

41. An implant according to claim 37, wherein said frame includes a plurality of linear extensions, at least two of such extensions sized and shaped to extend across a uterine wall.

42. An implant according to claim 41, wherein said at least two extensions are movable between a collapsible and a deployed position.

43. An implant according to claim 37, wherein said presterilized substance is sized and shaped so as to further cause the elimination of menorrhagia.

44. An implant according to claim 37, wherein said presterilized substance is sized and shaped so as to cause contraception in said uterus.

45. An implant for changing the gynecological state of a female comprising:
   a presterilized substance comprised of a frame at least partially covered by a polyester mesh material;
   said substance configured for causing a tissue response in uterine tissue; and,
   said substance sized and shaped for sufficiently contacting uterine tissue such that menorrhagia is eliminated in said female, wherein said presterilized substance is coated with an adhesion including substance.

46. An implant according to claim 45, wherein said frame includes a plurality of linear extensions, at least two of such extensions sized and shaped to extend across a uterine wall.

47. An implant according to claim 46, wherein said at least two extensions are movable between a collapsible and a deployed position.

48. An implant according to claim 45, wherein said substance is sized and shaped so as to further cause contraception in said uterus.

49. An implant for changing the gynecological state of a female comprising:
   a presterilized substance having a frame, at least a portion of which is covered by a mesh material.;
   said substance configured for causing a tissue response in uterine tissue; and,
   said substance sized and shaped for sufficiently contacting uterine tissue such that menorrhagia is eliminated in said female, wherein said presterilized substance is coated with an adhesion inducing substance.

50. An implant according to claim 49, wherein said mesh material is a polyester material.

51. An implant according to claim 49, wherein said frame includes a plurality of linear extensions, at least two of such extensions sized and shaped to extend across a uterine wall.

52. An implant according to claim 51, wherein said at least two extensions are movable between a collapsible and a deployed position.

53. An implant according to claim 49, wherein said substance is sized and shaped so as to further cause contraception in said uterus.

* * * * *